United States Patent [19]
Rich et al.

[11] Patent Number: 5,948,693
[45] Date of Patent: Sep. 7, 1999

[54] SOLID PHASE SYNTHESIS OF IMMUNOSUPPRESSIVE AGENTS

[75] Inventors: Daniel H. Rich; Prakash Raman; Yvonne M. Angell, all of Madison, Wis.

[73] Assignee: Wisconsin Alumni Research Foundation, Madison, Wis.

[21] Appl. No.: 08/837,137

[22] Filed: Apr. 14, 1997

Related U.S. Application Data

[63] Continuation-in-part of application No. 08/299,504, Sep. 1, 1994, Pat. No. 5,639,852.
[51] Int. Cl.⁶ .......................... G01N 33/543; A61K 38/12
[52] U.S. Cl. .......................... 436/518; 436/523; 530/317; 530/328; 530/333; 530/334; 530/335
[58] Field of Search ..................................... 530/300, 317, 530/333–338, 350; 436/518–525

[56] References Cited

U.S. PATENT DOCUMENTS

| | | |
|---|---|---|
| 4,384,996 | 5/1983 | Bollinger et al. . |
| 4,771,122 | 9/1988 | Seebach . |
| 4,814,323 | 3/1989 | Andrieu et al. . |
| 5,284,826 | 2/1994 | Eberle . |
| 5,510,240 | 4/1996 | Lam et al. ............................. 435/7.1 |

FOREIGN PATENT DOCUMENTS 0 484 281 A2   6/1992   European Pat. Off. .

OTHER PUBLICATIONS

Campbell, *Biology* 3rd Edition, Campbell, Benjamin Cummings Publishing Company, Inc., Redwood City, VA, (1993), pp. 850–872.
Lanier, L.L., Distribution and Function of Lymphocyte Surface Antigens, *Ann. N.Y. Acad. Sci.*, (1993), 677:86–93.
Mizel et al., Characterization of Lymphocyte Activating Factor )LAF) Produced by Macrophage Cell Line, *J. Immunol.* (1978), 120:1504–1508.
Shaw et al., Effects of Costimulator on Immune Responses In Vitro, *J. Immunol.* (1978), 120:1974–1980.
Teh et al., Direct Evidence for a Two–Signal Mechanism of Cytotoxic T–Lymphocyte Activation, *Nature* (1980), 285:163–165.
Shaw et al., Cellular Origins of Co–stimulator (IL2) and Its Activity in Cytotoxic T Lymphocyte Responses, *J. Immunol.* (1980), 124:2231–2239.
Chouaib, Tumor Necrosis Factor α: a Costimulator for Cytotoxic Cell Differentiation, *Nouv. Rev. Fr. Hematol.* (1991), 33:471–475.
Jenkins et al., CD28 Delivers a Costimulatory Signal Involved in Antigen–Specific IL–2 Production By Human T–Cells, *J. Immunol.* (1991), 147:2461–2466.
Fraser et al., Regulation of T–cell Lymphokine Gene Transciption by the Accessory Molecule CD28, *Mol. Cell. Biol.* (1992), 10:4357–4363.
Koulova et al., The CD28 Ligand B7/BB1 Provides Costimulatory Signa for Alloactivation of CD4+ TCells, J. Exp. Med. (1991), 173:759–762.

Gross et al., Identification and Distribution of the Costimulatory receptor CD28 in the Mouse, *J. Immunol.* (1992), 149:380–388.
Larsen et al., Functional Expression of the Costimulatory Molecule B7/BB1, on Murine Dendritic Cell Populations, *J. Exp. Med.* (1992), 176:1215–1220.
Kendrew (ed.), *The Encyclopedia of Molecular Biology*, Blackwell Science Ltd. (1994), pp. 29–31.
Kay, J.E., Inhibitory Effects of Cyclosporin A on Lymphocyte Activation, *Cyclosporin, Mode of Action and Clinical Application* (1989), Kluwer Academic Publishers, Dordrecht, The Netherlands, (A.W. Thompson, ed.), pp. 1–19.
Borel, Cyclosporine: Historical Perspectives, *Cyclosporin A*, Elsevier Biomedical Press, Amsterdam, The Netherlands, (D.J.G. White, ed.) (1982), pp. 5–15, 19–33.
Tam et al., *Peptides, Structure and Function*, (C.M. Deber et al. eds.), (1985) Pierce Chemical Co., Rockford, IL pp. 423–425.
Urban et al., *Int. J. Peptide Protein Res.* (1996), 47:182.
Carpino, L.A., 1–Hydroxy–7–azabenzotriazole. An Efficient Peptide Coupling Additive, *J. Am. Chem. Soc.* (1993), 115:4397–4398.
Pugh et al., *Int. J. Peptide Res.* (1992), 40:208.
Yamashiro et al., The Use of Trifluoroethanol For Imporved Coupling in Solid–Phase Peptide Synthesis, *Tetrahedron Lett.* (1976), 18:1469–1472.
Narita et al., The Solubility of Peptide Intermediates in Organic Solvents. Solubilizing Potential of Hexafluoro–2–propanol, *Bull. Chem. Soc. Jpn* (1988), 61:281–284.
Hu et al., *J. Med. Chem.* (1995), 38:4164.
Kates et al., A Novel, Convenient, Three–Dimensional Orthogonal Strategy for Solid–Phase Synthesis of Cyclic Peptides, *Tetrahedron Lett.* (1993), 34:1549–1552.
Kates et al., *Anal. Biochem.* (1993), 212:303.
Wenger, R.M., Total Syntehsis of 'Cyclosporin A' and 'Cyclosporin H,' Two Fungal Metabolites Isolated from the Species *Tolypocladium Inflatum* GAMS, *Helv. Chim. Acta.* (1984), 67:501–524.
Colucci et al., Synthesis of D–Lysine–Cyclosporine A. Further Characterization of BOP–C1 in the 2–7 Hexapeptide Fragment Synthesis, J. Org. Chem. (1990), 55:2895–2903.
Bartz et al., Proc. Natl. Acad. Sci., USA (1995), 92:5381.

(List continued on next page.)

*Primary Examiner*—Ponnathapura Achutamurthy
*Attorney, Agent, or Firm*—DeWitt Ross & Stevens S.C.

[57] ABSTRACT

The present invention relates generally to cyclosporin analogs, and more paritcularly to methods for the solid-phase synthesis and on-resin cyclization of cyclosporin analogs. Methods are described for the on-resin cyclization of sterically hindered compounds synthesized through solid phase synthesis techniques. The methods utilize solvent, temperature, and washing conditions that allow the efficient on-resin cyclization of compounds like analogs of cyclosporin A.

31 Claims, 18 Drawing Sheets

OTHER PUBLICATIONS

Gallop et al., Applications of Combinatorial Technologies to Drug Discovery. 1. Background and Peptide Combinatorial Libraries, *J. Med. Chem.* (1994), 37:1233–1248.

Tung et al., BOP–Cl Mediated Synthesis of the Cyclosporine A 8–11 Tetrapeptide Fragment, *J. Org. Chem.* (1986), 51:3350–3354.

Coste et al., Oxybenzotriazole Free Peptide Coupling Reagents for n–Methylated Amino Acids, *Tetrahedron Lett.* (1991), 32:1967–1970.

Gross, The Peptides: Analysis, Synthesis, Biology, Academic Press, Inc., New York (1979), 1:332.

Schöllkopf, U., Recent Applications of α–Metalated Isocyanides in Organic Synthesis, *Angew, Chem. Int. Ed.* (1977), 16:339–422.

Evans and Weber, *J. Am. Chem. Soc.* (1994), 108:6757.

Gordon et al., Applications of Combinatorial Technologies to Drug Discovery. 2. Combinatorial Organic Synthesis, Library Screening Strategies, and Future Directions, *J. Med. Chem.* (1994), 37:1385–1399.

Sheppard et al., *Int. J. Peptide Protein Res.* (1982), 29:451.

Zalipsky et al., Peptides, Structure and Function, (C.M. Deber et al. eds.), Pierce Chemical Co., Rockford, IL (1985), pp. 257–260.

Fields et al., *J. Biol. Chem.* (1993), 268:14153.

Angell et al., Solid–Phase Synthesis of Cyclosporin Peptides, *J. Am. Chem. Soc.* (1995), 117:7279–7280.

Kazmierski et al., Asymmetric Syntehsis of Topgraphically Constrained Amino Acids: Synthesis of the Optically Pure Isomers of α,β–Dimethyl–Phenylalanine and α,β–Dimethyl–1,2,3,4–Tetrahyroisoquinoline–3–Carboxylic Acid, *Tetrahedron Letters* (1991), 32:41:5769–5772.

Ko et al., Solid–Phase Total Synthesis of Cyclosporine Analogues, Helv. Chim. Acta (1997), 80:695–705.

Spanevello et al: Tetrahedron Letters, vol. 32, pp. 4675–4678, 1991.

McMurray: Tetrahedron Letters, vol. 32, pp. 7679–7682, 1992.

Trzeciak et al: Tetrahedron Letters, vol. 32, pp. 4557–4560, 1992.

[MeLeu(3-OH)$^1$]-CsA: $R_1=R_2=CH_2CH(CH_3)_2$

[MeLeu(3-OH)$^1$,MeAla$^{4,6}$]-CsA: $R_1=R_2=CH_3$

D-Ala-MeLeu-MeLeu-MeVal-MeBmt-Abu-Sar-MeLeu-Val-MeLeu-Ala
  8     9     10     11    1    2    3    4    5    6    7

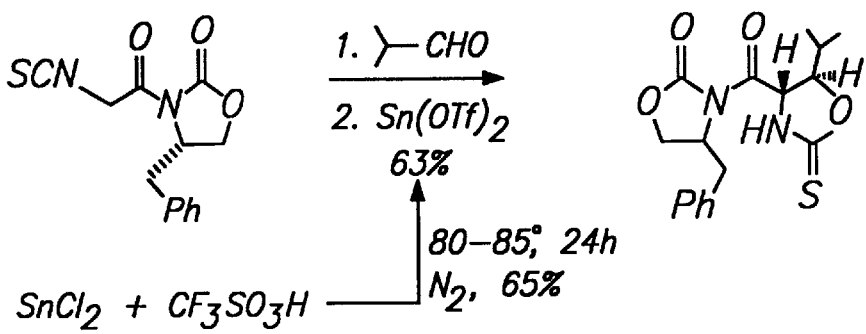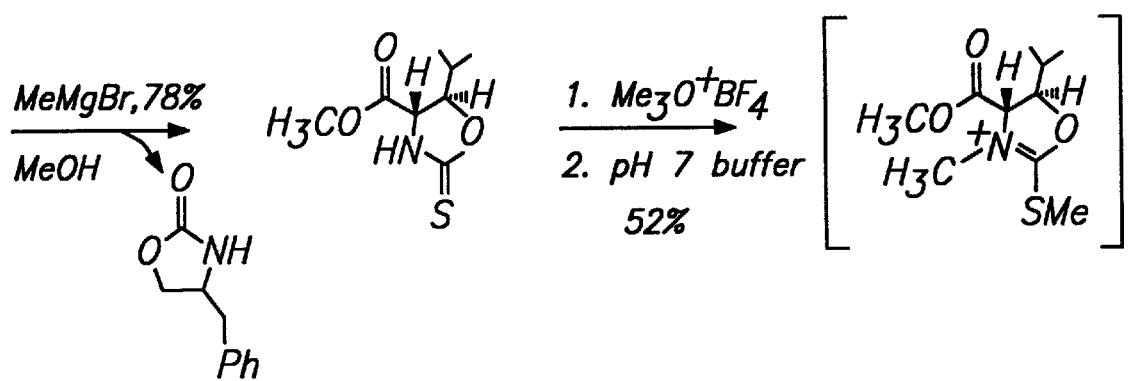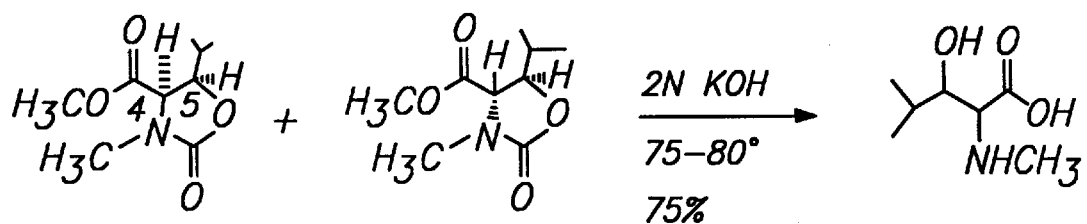
FIG. 6

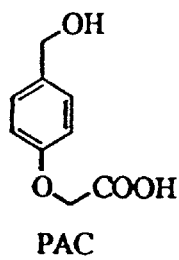
PAC
(TFA/H2O, 95:5)
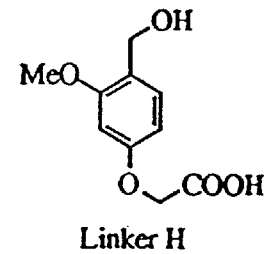
Linker H
(TFA/H2O/CH2Cl2, 10:1:89, -20°C)
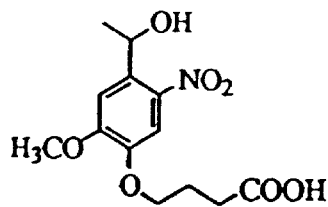
Photolabile Linker
( hv, 350nm, CH2Cl2/MeOH, 9:1)
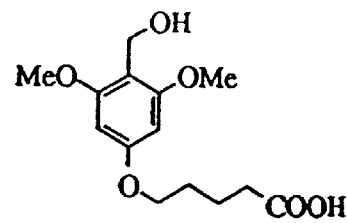
HAL
(TFA/H2O/CH2Cl2, 2:0.2:97.8, -20°C)
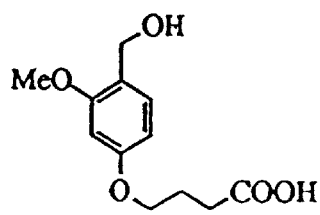
HMPB
(TFA/H2O/CH2Cl2, 1:0.1:98.9)
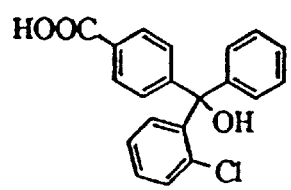
Trityl Linker
(AcOH/MeOH/CH2Cl2, 5:1:4)
FIG. 18

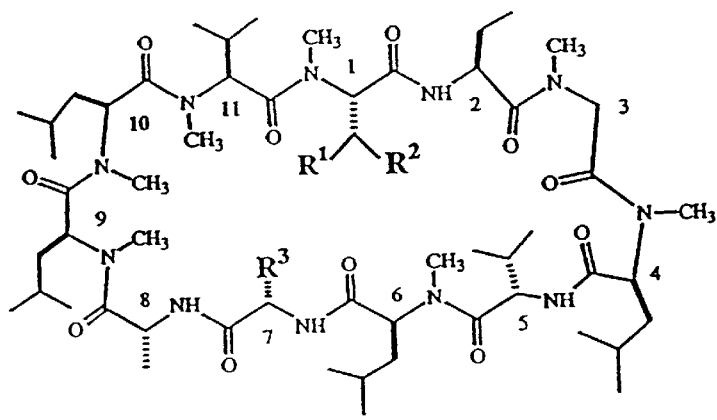

(SEQ ID NO:1) 1: CsA, $R^1$ = OH; $R^2$ = CH(CH$_3$)CH$_2$CH=CHCH$_3$; $R^3$ = CH$_3$
(SEQ ID NO:36) 2: [MeLeu$^1$]CsA, $R^1$ = H; $R^2$ = isopropyl; $R^3$ = CH$_3$
(SEQ ID NO:28) 3: [MeLeu$^1$, Asp$^7$]CsA, $R^1$ = H; $R^2$ = isopropyl; $R^3$ = CH$_2$COOH
(SEQ ID NO:31) 4: [MeLeu$^1$, Asp(OBn)$^7$]CsA, $R^1$ = H; $R^2$ = isopropyl; $R^3$ = CH$_2$COOBn
(SEQ ID NO:32) 5: [MeSer$^1$]CsA, $R^1$ = OH; $R^2$ = H; $R^3$ = CH$_3$
(SEQ ID NO:33) 6: [MeThr$^1$]CsA, $R^1$ = OH; $R^2$ = CH$_3$; $R^3$ = CH$_3$
(SEQ ID NO:34) 7: [MeSer(OBn)$^1$]CsA : $R^1$ = OBN; $R^2$ = H; $R^3$ = CH$_3$
(SEQ ID NO:35) 8: [MeThr(OBn)$^1$]CsA : $R^1$ = OBn; $R^2$ = CH$_3$; $R^3$ = CH$_3$

FIG. 19

[MeLeu¹, Asp⁷]CsA, 3

Key : (a) Sequential Deprotection/Coupling;
(b) Pd(Ph₃)₄, AcOH, NMM, CHCl₃; (c) 2%
DBU / NMP; (d) BOP, HOBt, DIEA, NMP,
3 days; (e) TFA / H₂O / CH₂Cl₂ (10 : 1 : 89)
at -20°C for 4 hrs.

SOLID PHASE SYNTHESIS OF IMMUNOSUPPRESSIVE AGENTS

The present application is a continuation-in-part of U.S. patent application Ser. No. 08/299,504, filed Sep. 1, 1994, now U.S. Pat. No. 5,639,852.

This invention was made with United States government support awarded by NIH Grant Nos. AR32007 and GM50013. The United States has certain rights in this invention.

FIELD OF THE INVENTION

The present invention relates generally to cyclosporin analogs and more particularly to methods for the solid-phase synthesis and on-resin cyclization of cyclosporin analogs.

BACKGROUND OF THE INVENTION

Recent advances in molecular immunology have allowed researchers to obtain a detailed view of the cellular and molecular events which take place during the human immune response to pathogenic infection. In addition to determining the roles of the various lymphocytes in the immune response, researchers have also made some progress in mapping out their biochemical interactions, including those that involve macromolecules which may act as chemical signals to coordinate lymphocyte actions and functions.

The modern view of immunology has the T-cell as a key player in the body's specific defense mechanism. Two particular classes of T-cells, the helper T-cell ($T_H$) and the cytotoxic T-cell ($T_C$), play important roles in the both the humoral and the cell-mediated immune response. In contrast, B-lymphocytes are exclusively involved in the humoral immune response.

The humoral response is usually directed against free circulating pathogens or their antigens. Antigen-Presenting cells (APCs), such as macrophages, express fragments of digested antigens on their outer membranes often in combination with Class II MHC (Major Histo-Compatibility) proteins. Recognition of these Class II MHCs and foreign antigens trigger $T_H$ cells to proliferate. This, in turn, triggers B-cells to secrete antibodies which eventually neutralize the pathogens.

The cell-mediated response involves participation by both $T_H$ and $T_C$ cells. In this case, a cell of the body infected by the pathogen displays pathogen antigens in combination with Class I MHC proteins and thereby stimulates $T_H$ cells to activate $T_C$ cells which lyse the infected cell. (See, Biology (3rd. ed.) Campbell, Benjamin Cummings Publishing Company, Inc. [1993]).

Because of the critical role played by the T-cells in the body's defense systems, the destruction of certain T-cell populations by the AIDS virus, effectively robs the body of its ability to defend itself. AIDS therapies have therefore focused on ways to prevent T-cell destruction and/or regenerate T-cell function. Such efforts have thus far been hampered by a lack of complete understanding of T-cell biochemistry including the elaboration of soluble mediators, ie., cytokines.

There have been numerous studies of both biochemical mediators and cellular interactions which cause the stimulation and thereby proliferation of the body's T-cells. Much of the work has centered on discovering the identity of both the chemical signals and the membrane receptors which are directly responsible. (See, Lanier "Distribution and Function of Lymphocyte Surface Antigens" Ann. N.Y. Acad. Sci., 677:86 [1993]).

It is generally agreed that T-cell activation requires more than just binding of the T-cell receptors (TCRs) to specific antigen/MHC protein combinations. (See *Biology* (3rd. ed.) Campbell, Benjamin Cummings Publishing Company, Inc. [1993]). In particular, there has been much research on the existence of additional molecular binding events, in effect a "costimulatory" signal. These costimulatory signals, although not antigen-specific, have been shown to be critical for many stages of T-cell development, activation, and proliferation. (See, Mizel "Characterization of Lymphocyte Activating Factor (LAF) Produced by Macrophage Cell Line" J. Immunol., 120:1504 [1978]).

Recent immunological research has focused on two types of costimulatory signals. The first class of costimulatory signals are macromolecules which freely diffuse through the intercellular milieu, where they bind to receptors on the exterior membrane of the T-cell, causing the desired metabolic changes. These free costimulators are themselves typically secreted by other lymphocytes. Shaw et al. were among the first to describe a factor, designating it by the term "costimulator." The molecule behaved like a nonspecific second signal to induce the proliferation of T-cells, following the first signal which is an antigen. (See, "Effects of Costimulator on Immune Responses IN VITRO," J. Immunol. 120:1974 [1978]). Teh et al. describe the use of the same "Costimulator" in a model system to activate cytotoxic T-cells, which were initially stimulated by antigen. (See, "Direct Evidence for a Two-Signal Mechanism of Cytotoxic T-Lymphocyte Activation," Nature 285:163 [1980]). This was also corroborated by Shaw et al. (See, "Cellular Origins of Co-stimulator (IL2) and Its Activity in Cytotoxic T Lymphocyte Responses," J. Immunol., 124:2231 [1980]).

"Costimulators" and other related compounds are generally peptides referred to under the general category of "interleukins." It is currently uncertain whether compounds outside the Interleukin family can elicit T-cell metabolic changes as well. A relatively recent article by Chouaib describes the use of purified tumor necrosis factor (TNF) in the costimulation of cytotoxic cell differentiation. (See, "Tumor Necrosis Factor α: a Costimulator for Cytotoxic Cell Differentiation," Nouv. Rev. Fr. Hematol., 33:471 [1991]). However, this compound only works in combination with interleukin-2, which has the ability to stimulate T-cells without the participation of another nonspecific molecule.

A second class of costimulatory signals under investigation are membrane bound ligands that are typically found on other APCs, which bind to receptor proteins on the T-cell surface. In particular, there has been considerable research focused on the CD28 receptor present on the outer membrane of T-cells. (See, Jenkins et al. "CD28 Delivers a Costimulatory Signal Involved in Antigen-Specific IL-2 Production By Human T Cells," J. Immunol., 147:2461 [1991]; and Fraser et al. "Regulation of T-cell Lymphokine Gene Transcription by the Accessory Molecule CD28," Mol. Cell. Biol., 10:4357 [1992]). This receptor and its activation ligand present on B-lymphocytes, "B7/BB1," may play a pivotal role in T-cell activation through regulation of their cytokine gene transcription. (See, Koulova et al. "The CD28 Ligand B7/BB1 Provides Costimulatory Signal for Alloactivation of CD4+ TCells," J. Exp. Med., 173:759 [1991]; Gross et al. "Identification and Distribution of the Costimulatory receptor CD28 in the Mouse," J. Immunol., 149:380 [1992]; and Larsen et al. "Functional Expression of the Costimulatory Molecule B7/BB1, on Murine Dendritic Cell Populations," J. Exp. Med., 176:1215 [1992]).

Although purified B7/BB1 may be a viable T-cell stimulator, it is a complex protein of high molecular weight, that can only be produced in large quantities through recombinant DNA techniques. It is clear that a more simple costimulator that can be chemically synthesized would find use in the art.

SUMMARY OF THE INVENTION

The present invention relates to the synthesis of cyclosporin derivatives to be used as agents for increasing human white blood cell activity and proliferation. In one embodiment, the present invention relates to modified cyclosporin derivatives which have the property of both being non-immunosuppressive and being immunostimulatory agents (i.e., agents useful for increasing lymphocyte proliferation and activity in vitro).

In one embodiment, the present invention contemplates an immunostimulatory analog of the cyclosporin as shown in FIG. 1. In a preferred embodiment, the present invention contemplates the analog having the structure shown in FIG. 3.

It is not intended that the solid phase synthesis be limited to any particular solid particle. In one embodiment, the particle is insoluble in all the solvents which are used and has a stable physical form which permits ready filtration. It also contains a functional group to which the first protected amino acid can be firmly linked by a covalent bond. Many polymers and modes of attachment are possible. Among the possible polymers, the present invention contemplates cellulose, polyvinyl alcohol, polymethacrylate and sulfonated polystyrene. The preferred polymer is methylbenzhydrylamine (MBHA) polystyrene resin.

The present invention contemplates a method of stimulating immune cells, comprising contacting the immune cells in vitro with an immunostimulatory analog of the cyclosporin of FIG. 1. In one embodiment, the method further comprises the step of pretreating the immune cells with a mitogen (e.g., PHA). It is not intended that the present invention be limited by the nature of the immune cells. In one embodiment, the immune cells are lymphocytes.

The present invention provides methods for coupling amino acid residues during solid phase synthesis. In one embodiment, the present invention provides a method for coupling amino acid residues during solid phase synthesis, comprising: providing in any order, a solid support, a linker, wherein the linker is anchored to the solid support to produce a solid support-bound linker, at least one amino acid residue, wherein the amino acid residue is bound to the solid support-bound linker to produce a bound amino acid residue, an unbound amino acid residue, and a solvent system comprising a polar aprotic solvent; and reacting the bound amino acid residue with the unbound amino acid residue in the presence of the solvent system thereby coupling the bound amino acid residue with the unbound amino acid residue.

In one embodiment of the method, the solid support comprises a spacer. In a preferred embodiment, the spacer is polyethylene glycol. It is contemplated that the spacer comprise any appropriate compound present within or on the structure of the solid support. It is further contemplated that the solid support be comprised of various materials, including but not limited to resins.

In an alternative embodiment of the method the linker is a mild-acid labile linker. In yet another embodiment, the linker is a photolabile linker.

In one embodiment of the method the reacting is conducted at a temperature above approximately 20° C. In a preferred embodiment, the temperature is in the range of about 40° C. to about 70° C. In an alternative preferred embodiment, the temperature is less than the boiling point of the aprotic solvent.

In another embodiment of the method, the polar aprotic solvent is selected from the group consisting of N-methyl pyrrolidinone, dimethylacetamide, dimethylformamide, tetramethylurea, and dimethyl sulfoxide. In a preferred embodiment, the solvent system further comprises a chaotropic agent, including but not limited to the group consisting of potassium thiocyanate, lithium perchlorate, lithium bromide, and lithium chloride.

The present invention also provides methods for cyclizing peptides on a solid support. In one embodiment, the present invention provides a method of cyclizing a peptide on a solid support, comprising: providing a peptide, wherein the peptide is linked to a solid support through an allyl-modified amino acid residue, an orthogonal deprotection agent, and a cyclizing reaction solution comprising benzotriazolyl-N-oxy-tris(dimethylamino)phosphonium hexafluorophosphate; deprotecting the allyl-modified amino acid residue with the orthogonal deprotection agent to produce a modified peptide intermediate; and reacting the peptide intermediate with the cyclizing reaction solution, thereby cyclizing the modified peptide intermediate to produce a cyclized peptide on a solid support.

In one preferred embodiment, the peptide comprises an eleven amino acid residue modified peptide. In another preferred embodiment, the eleven amino acid peptide residue is cyclosporin or a cyclosporin analog.

In one embodiment, the orthogonal deprotection agent is $Pd(PPh_3)_4$. In an alternative embodiment, the cyclizing reaction solution further comprises 1-hydroxybenzotriazole and diisopropylethylamine. In a preferred embodiment the 1-hydroxybenzotriazole and diisopropylethylamine are in an equivalent ratio of approximately 1:1.2.

In another embodiment, the solid support comprises polystyrene. In an alternative embodiment, the allyl-modified amino acid residue of the modified peptide is linked to the solid support through a linker. In one preferred embodiment, the linker is a mild-acid labile linker. In an alternatively preferred embodiment, the linker is a photolabile linker.

The present invention also provides alternative methods for cyclizing peptides on solid supports. In one embodiment, the present invention provides a method of cyclizing a peptide on a solid support, comprising: providing a peptide comprising an analog of cyclosporin, wherein the peptide is linked to a solid support through an allyl-modified amino acid residue, an orthogonal deprotection agent, and a cyclizing reaction solution comprising benzotriazolyl-N-oxy-tris (dimethylamino)phosphonium hexaflurophosphate; deprotecting the allyl-modified amino acid residue with the orthogonal deprotection agent to produce a modified peptide intermediate; and reacting the peptide intermediate with the cyclizing reaction solution, thereby cyclizing the modified peptide intermediate to produce an analog of cyclosporin on a solid support. In one preferred embodiment, the peptide is an eleven amino acid residue modified peptide.

In an alternative embodiment, the orthogonal deprotection agent is $Pd(PPh_3)_4$. In another embodiment, the cyclizing solution further comprises 1-hydroxybenzotriazole and diisopropylethylamine. In a particularly preferred embodiment the 1-hydroxybenzotriazole and diisopropylethylamine are in an equivalent ratio of approximately 1:1.2.

In one preferred embodiment, the solid support comprises polystyrene. In alternative preferred embodiments, the allyl-modified amino acid residue of the modified peptide is linked to the solid support through a linker. In one preferred embodiment, the linker is a mild-acid labile linker. In an alternative preferred embodiment, the linker is a photolabile linker.

DESCRIPTION OF THE DRAWINGS

FIG. 6 depicts the synthesis of (2S,3R)-3-Hydroxy-N-methylleucine by the Evans method.

FIG. 18 depicts the chemical structures of several of the linkers contemplated for use with the present invention.

FIG. 19 indicates the chemical structure of some of the CsA analogs that may be generated using the on-resin cyclization procedures of the present invention.

DESCRIPTION OF THE INVENTION

Figure 1:
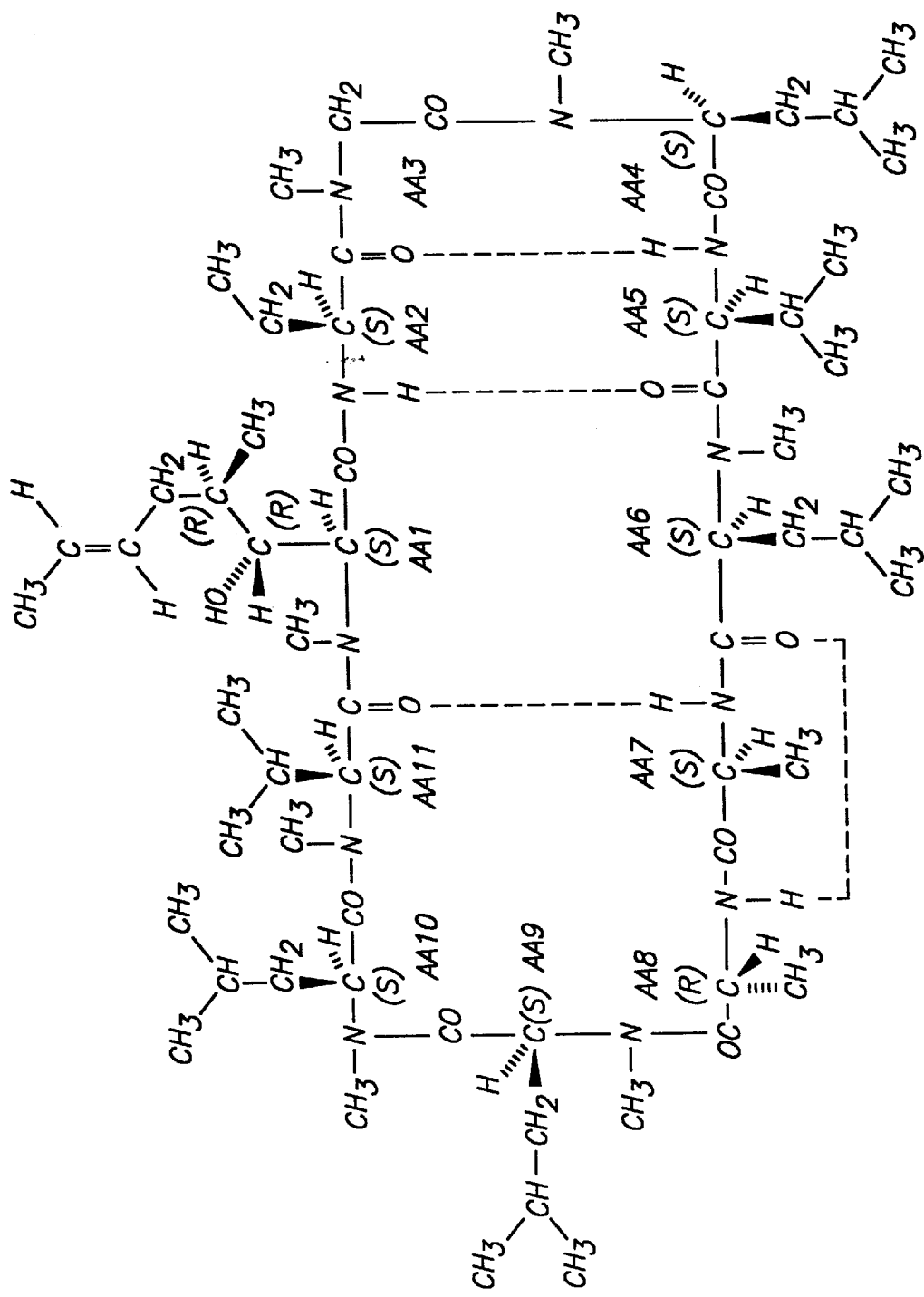
FIG. 1 is a structure of unmodified Cyclosporin A.
Figure 2:
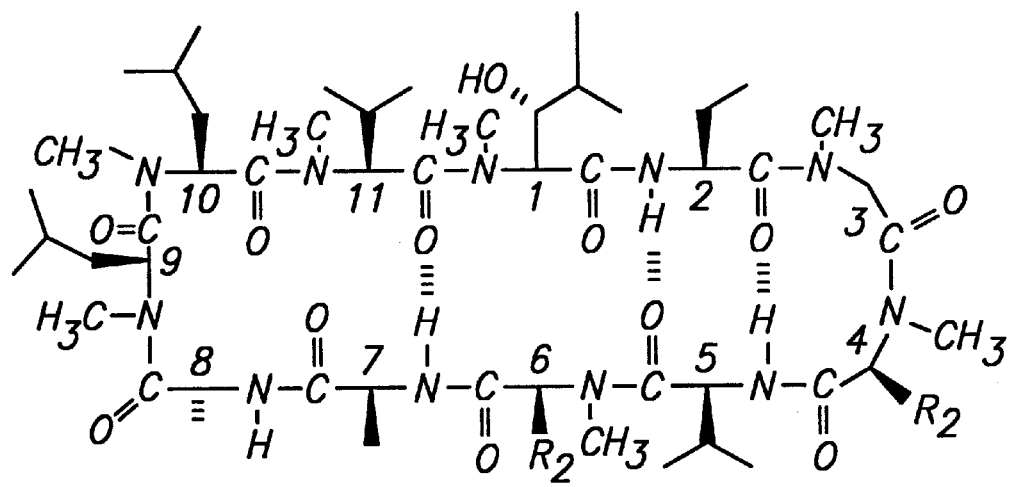
FIG. 2 depicts the structure of a previously modified Cyclosporin of the prior art.

The present invention relates to cyclosporin derivatives to be used as agents for increasing human white blood cell activity and proliferation. To facilitate understanding of the invention, a number of terms are defined below.

The terms "chaotropic agent," "chaotropic compound," and the like refer to the property of certain substances, generally containing ions (e.g., SCN$^-$ and ClO$_4$), to disrupt the structure of water. As a result, chaotropic agents promote the solubility of nonpolar substances in polar solvents (e.g., water), the unfolding of proteins, etc. Chaotropic agents contemplated by the present invention include, but are not limited to, potassium thiocyanate, lithium perchlorate, lithium bromide, and lithium chloride.

The term "solid support" refers broadly to supports used in the solid phase synthesis of, for example, peptides, nucleic acids, oligonucleotides, and small organic molecules. Solid supports include, but are not limited to, polymer resins (e.g., polyethylene glycol and polystyrene), gels (e.g., polyethylene glycol gels), polyacrylamide/polyethylene glycol copolymer resins (e.g., RAPP polymer resin, NOVASYN® PEG A [Calbiochem-Novabiochem]), controlled pore glass supports (e.g., the CPG supports commercially available from Millipore), as well as silica beads and silicon wafers. In preferred embodiments, the solid supports of the present invention are copolymers of polystyrene and polyethylene glycol; the polyethylene glycol component of the copolymer is considered to be a "spacer."

The term "spacer" refers to a material in a solid support that serves to separate the sites of attachment (e.g., those sites on the support where a growing peptide can adhere) of the solid support. The use of solid supports with spacers provides favorable conditions for solvent permeation, thereby facilitating coupling efficiencies for the synthesis of difficult peptide sequences. Preferred embodiments of the present invention utilize copolymers of polyethylene glycol and polystyrene, the polyethylene glycol (PEG) serving as the spacer.

The term "linker" refers to an anchoring group that serves to anchor or tether a growing target molecule to a solid support (e.g., polystyrene resin-PEG) during solid phase synthesis. Desirable characteristics of linkers may include, for example, lability to particular acid or base conditions. The linker is sometimes the point of cleavage following synthesis; as such, chemical groups on the linker can become functional groups of the cleaved target molecule.

The terms "mild acid labile linker" and "photolabile linker" refer broadly to linkers that do not require high concentrations of acid (e.g., TFA) to effect cleavage from a solid support of, for example, a peptide product following solid phase synthesis (See e.g., FIG. 18). Because cleavage results from the use of mild acid (i.e., with mild acid labile linkers) or certain wavelengths of light (e.g., 350 nm) (i.e., with photolabile linkers), the use of these linkers allows for the non-destructive cleavage of peptides from the solid support under appropriate conditions. The mild acid-labile linkers contemplated by the present invention include, but are not limited to, 4-(4-hydroxymethyl-3-methoxyphenoxy)-butyric acid (HMPB), 4-hydroxymethylphenoxyacetic acid (PAC), 4-hydroxymethyl-3-methoxyphenoxyacetic acid (Linker H), HAL, and trityl linker.

The terms "carboxamide terminus," "carboxamide termini," and the like refer to an end of a target molecule, synthesized by solid phase techniques and containing an —NHCO—group, that was covalently attached to a solid support (through, e.g., a linker) prior to cleavage.

The term "solvent" refers to a liquid compound that is used to dissolve solids, liquids, or gases without reacting with them (unless desired) to bring the reaction components into close chemical proximity. Generally speaking, in a solution consisting of several components, the component present in excess is deemed to be the solvent.

The term "polar aprotic solvent" refers broadly to polar solvents lacking acidic hydrogens. Examples of polar aprotic solvents include, but are not limited to, N-methyl pyrrolidinone (NMP), dimethylacetamide (DMA), dimethylformamide (DMF), tetramethylurea, and dimethyl sulfoxide (DMSO); in preferred embodiments, the polar aprotic solvent is NMP.

The term "solvent system" refers to a solution comprising a solvent and at least one other component; for example, a solvent system may comprise tetrahydrofuran, acetic acid, and water. The term "aqueous solvent system" refers to a solvent system comprising at least 3 parts (i.e., 3 parts of 100 parts of a reaction mixture on a volume basis) water, more preferably greater than 5 parts water, and preferably less than 30 parts water.

The term "amino acid residue" refers broadly to the amino acids commonly found in proteins (both L and D optical isomers) (See e.g, *The Encyclopedia of Molecular Biology*, (Blackwell Science Ltd., Kendrew, ed.) pp. 29–31 [1994]), non-natural amino acids (e.g, Sar [sarcosine] and Abu [α-aminobutyric acid]), and amino acids that have been modified through, for example, the addition of an alkyl group (e.g, MeVal). Cyclosporin (CsA) analogs may be generated by producing peptides with amino acid substitutions (compared to CsA itself) based on, for example, similarity or dissimilarity in polarity, charge, solubility, hydrophobicity, hydrophilicity, and/or the amphipathic nature of the residues.

The term "orthogonal deprotection agent" refers to a deprotection agent that removes one protecting group from an amino acid residue containing two (or more) independent classes of protecting groups removable by differing chemical mechanisms. To illustrate, an amino acid residue may have its carboxyl-terminus protected by an allyl group, whereas its amino terminus is protected by Fmoc; an orthogonal deprotection agent may remove the allyl group, leaving the Fmoc group intact.

The term "allyl group" refers to $CH_2=CH-CH_2-$ or a derivative thereof (e.g., allyl chloride). The term "allyl-modified amino acid residue" refers to an amino acid residue wherein one of its finctional groups (e.g, the carboxy terminus of aspartic acid) is covalently linked to an allyl group.

The term "cyclizing reaction solution" refers to a solution which is capable of effecting cyclization of a peptide to produce an analog of CsA. The present invention contemplates on-resin cyclization of linear precursors of CsA analogs using various solutions, including, but not limited to BOP/HOBt/DIEA in DMF. In preferred embodiments, on-resin cyclization is performed with BOP (5 eq)/HOBt (5 eq)/DIEA (10 eq) in DMF for 72 hours. In alternative preferred embodiments, the cyclization reaction solution comprises PyAOP/HOAt/DIEA. It is contemplated that peptides of varying lengths will be produced using the methods of the present invention. In preferred embodiments, the peptide is a modified peptide of eleven amino acid residues.

A cyclosporin "derivative" or "analog" has the findamental structure of Cyclosporin A (CsA), namely a cyclic undecapeptide, with amino acid substitutions at particular positions. In accordance with the present invention, a member from the class of novel cyclosporin derivatives is to be mixed with lymphocytes along with one or more antigens. In one embodiment, the member is a cyclosporin derivative modified in either the 1, 4, or 6 position or any combination thereof, by chemical, enzymatic, or biological means.

An analog is "immunostimulatory" if it causes immune cells (e.g., lymphocytes) to be stimulated (e.g., as measured by proliferation). A "costimulatory" is therefore immunostimulatory.

The description of the present invention involves: (I) Properties of Unmodified Cyclosporin (Prior Art); (II) Properties of Previously Modified Cyclosporin Analogs (Prior Art); (III) Properties of Modified Cyclosporin Analogs of the Present Invention; (IV) Synthesis of Novel Cyclosporin Analogs; (V) Solid Phase Synthesis Methods for the Generation of Compounds Containing Sterically Hindered Amino Acid Residues; (VI) On-Resin Cyclization of Sterically Hindered Compounds; and (VII) Solid Phase Synthesis for the Generation of Combinatorial Libraries.

I. Properties of Unmodified Cyclosporin

Cyclosporin A (CsA) was first discovered in 1970 by researchers at Sandoz Inc. as a metabolite of two strains of fingi (*Tolypocladium inflatum* and *Cylindrocarpon lucidum*). Its strong in vivo immunosuppressive effects were first discovered in trials using mice which led to successful clinical trials, and it is now routinely used to suppress the immune response for patients scheduled to undergo procedures such as organ transplantation. One of the attractive properties of cyclosporin A is that, unlike other previous immunosuppressive drugs, it does not show a general inhibition of cell proliferation. Only lymphocytes are inhibited, and the drug is not cytotoxic to those lymphocytes.

A strongly hydrophobic undecapeptide (See FIG. 1), CsA suppresses both humoral and cell-mediated immunity. It is generally believed that CsA inhibits a relatively early step of lymphocyte proliferation, before the initiation of DNA synthesis, and does not inhibit the cytotoxicity or response of T or B cells which have been already primed to interleukin-2 (IL-2). The precise mode of action of CsA has not been fully elucidated as of present but it is agreed upon that: 1) CsA binds mainly to cyclophilin, an abundant cytoplasmic protein, in the cell; 2) CsA affects internal cell $Ca^{2+}$ sensitivity; and 3) a combination of these properties as well as other unknown steps may lead to reduced production of interleukins and other cytokines in the cell, which would lead to decreased lymphocyte activation and proliferation. (See, *Cyclosporin, Mode of action and Clinical Application*, Thomson: Kluwer Academic Publishers, 1989; *Cyclosporine, Biological Activity and Clinical Applications*, Kahan: Elsevier Biomedical Press, 1982; and *Cyclosporin A*, White: Grune & Stratton, 1984).

In addition to its clear and tested utility as an immunosuppressive agent, it was recently discovered by Andrieu (see U.S. Pat. No. 4,814,323, herein incorporated by reference), that CsA possesses potential utility as an anti-AIDS agent (ie., it has been shown to reduce the replication of the HIV virus).

II. Properties of Previously Modified Cyclosporin Analogs

There have also been numerous studies of the biological and medicinal effects of modified cyclosporin derivatives. Many of these cyclosporin derivatives have be shown to possess novel properties and have in fact been patented. The convention for cyclosporin analog nomenclature includes listing any modified amino acids and their positions relative to unmodified cyclosporin A. For example, an analog of cyclosporin possessing Serine in place of the normal Valine as the fifth amino acid would have the name $(Ser^5)$-CsA.

Some CsA analogs have been previously synthesized. The biological activity of these analogs ranges from immunosuppressive properties equal to that of unmodified CsA to having reduced or even no immunosuppressive activity. Another novel class of CsA derivatives was disclosed by the present inventor in 1986. (See, Rich, D., Dhaon, M., Dunlap, B. and Miller, S., J. Med. Chem., 29:978 [1986]). These CsA analogs all contained modified amino acids in the 1 position. In addition there have been several patented CsA derivatives developed by Sandoz, including (Allylgly$^2$)-CsA, ([D]-Ser$^8$)-CsA, and (O-(2-hydroxyethyl)(D)Ser$^8$)-CsA which possess strong immunosuppressive, anti-inflammatory, and anti-parasitic activity. (See, U.S. Pat. Nos. 4,384,996, 4,771,122 and 5,284,826).

Recently, however, there has been added emphasis on discovering CsA analogs that possess little or no immunosuppressive activity. The utility of these compounds would be as anti-AIDS, rather than immunosuppressive agents. As discussed above, a recently issued patent described the use of unmodified CsA to combat the spread of the HIV virus. Clearly, it would be preferable to use a compound to treat AIDS that could inactivate the HIV virus, while not suppressing the immune system, as CsA does. Such reasoning has led researchers to investigate CsA analogs with both such properties. A Sandoz European Patent (#0484281A2, herein incorporated by reference), discloses CsA derivatives which are reported to be active against HIV replication, but lack immunosuppressive activity.

III. Properties of Cyclosporin Analogs of the Present Invention

Figure 3:
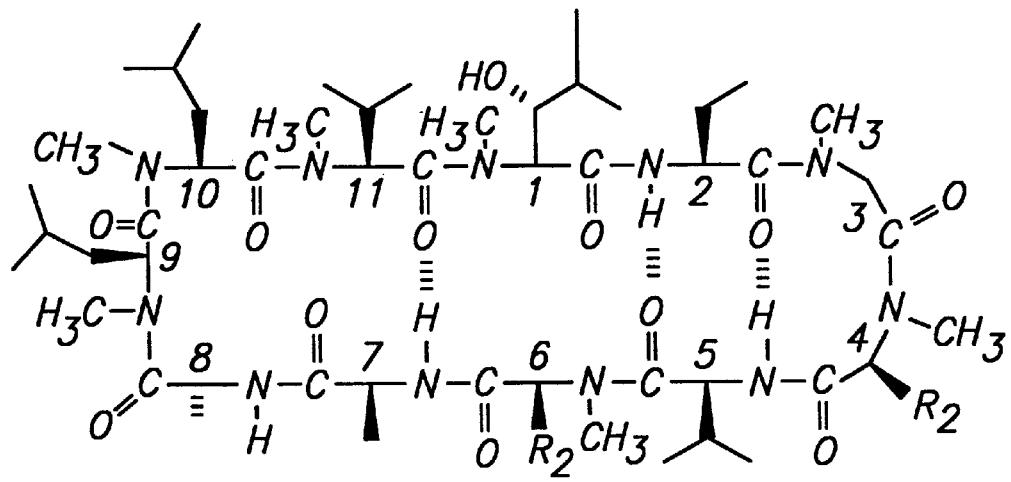
FIG. 3 depicts the structure of a preferred Cyclosporin analog of the present invention.

During the course of preparing novel CsA analogs, it was discovered that immunostimulatory analogs of CsA could also be synthesized. In particular, the [MeLeu(3-OH)$^1$, MeAla$^{4,6}$]CsA (FIG. 3) and the [(D)-MeVal$^{11}$, MeLeu(3-OH)$^1$]CsA analogs augmented the mitogen induced in vitro DNA synthesis response of human peripheral blood monocytes (PBMCs) at all the concentrations tested (e.g., 0.001 μg/mL to 10 μg/mL). Tables 5 and 6 below provide these data.

This novel property has not been previously described for any cyclosporin analog. As CsA is known primarily as an immunosuppressive agent, finding a derivative of CsA that possessed the opposite effect was totally unexpected.

IV. Synthesis of Cylosporin Analogs of the Present Invention

The present invention relates to the synthesis of CsA analogs with amino acid substitutions at either the 1, 4, and/or 6 positions, or any combination thereof. These analogs were tested based on two criteria: 1) their ability to act as immunostimulatory agents; and 2) their ability to inhibit cytopathic effect due to infection by the HIV virus. It was found that two analogs, (D-MeVal$^{11}$, L-MeLeu(3-OH)$^1$)-CsA and (MeLeu(3-OH)$^1$, MeAla$^{4,6}$)-CsA, were able to finction as immunostimulatory agents, as demonstrated by their ability to augment the PHA-induced DNA synthetic response of PBMCs. In addition, the latter analog was able to inhibit cytopathic effect resulting from infection by the HIV virus, indicating its potential utility as an anti-AIDS therapeutic.

This preferred analog of the present invention was synthesized according to the following general procedure:

First, the novel amino acid L-MeLeu(3-OH) was synthesized (as described infra) and subsequently condensed with acetone into a modified form.

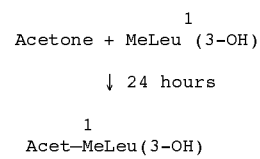

Second, a methylalanine amino acid (MeAla), N-protected by a t-butoxycarbonyl group (Boc), was reacted with an alanine amino acid (Ala), C-protected by a benzyl ester group (OBzl), along with (bis(2-oxo-3-oxazolidinyl) phosphonic chloride) (BOP-Cl) and diisopropylethylamine (DIEA) to form an N and C-protected MeAla-Ala dipeptide.

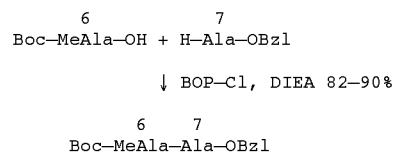

Third, the N- and C-protected MeAla-Ala dipeptide was N-deprotected by reaction with trifluoroacetic acid (TFA).

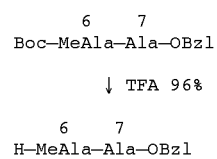

Fourth, the C-protected MeAla-Ala dipeptide was reacted with a valine amino acid (Val), N-protected by Boc, along with BOP-Cl and DIEA to form an N and C-protected Val-MeAla-Ala tripeptide.

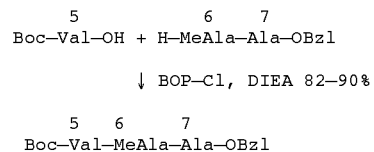

Fifth, the N and C-protected Val-MeAla-Ala tripeptide was N-deprotected by reaction with TFA.

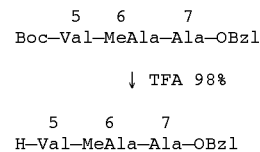

Sixth, the C-protected Val-MeAla-Ala tripeptide was reacted with a MeAla amino acid, N-protected by Boc, along with BOP-Cl and DIEA to form an N and C-protected MeAla-Val-MeAla-Ala tetrapeptide (SEQ ID:NO 3).

STEP 6

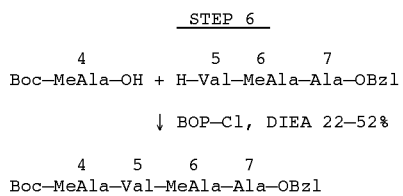

Seventh, the N and C-protected MeAla-Val-MeAla-Ala tetrapeptide (SEQ ID:NO 3) was N-deprotected by reaction with TFA.

STEP 7

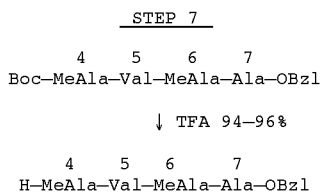

Eighth, the C-protected MeAla-Val-MeAla-Ala tetrapeptide (SEQ ID:NO 3) was reacted with an α-aminobutyric acid-sarcosine dipeptide (Abu-Sar), N-protected by Boc, along with BOP-Cl and DIEA to form an N and C-protected Abu-Sar-MeAla-Val-MeAla-Ala hexapeptide (SEQ ID:NO 4).

STEP 8

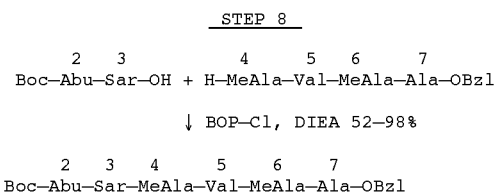

Ninth, the N and C-protected Abu-Sar-MeAla-Val-MeAla-Ala hexapeptide (SEQ ID:NO 4) was N-deprotected by reaction with TFA.

STEP 9

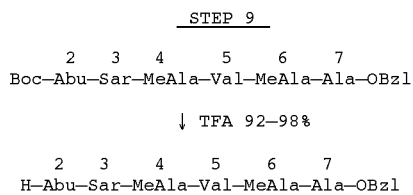

Tenth, the C-protected Abu-Sar-MeAla-Val-MeAla-Ala hexapeptide (SEQ ID:NO 4) was reacted with the modified MeLeu(3-OH) amino acid of the first step along with 1-hydroxybenzotriazole (HOBt), N-methyl morpholine (NMM, and dicyclohexyl carbodiimide (DCC) to form an N and C-protected MeLeu(3-OH)-Abu-Sar-MeAla-Val-MeAla-Ala heptapeptide (SEQ ID:NO 5).

STEP 10

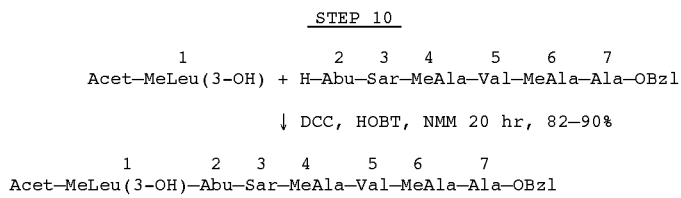

Eleventh, the N- and C-protected heptapeptide (SEQ ID:NO 5) was N-deprotected by reaction with aqueous hydrochloric acid and methanol.

STEP 11

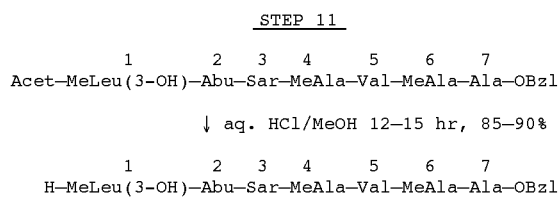

Twelfth, a methylvaline amino acid (MeVal), C-protected by a Boc group was reacted with a methylleucine amino acid (MeLeu), N-protected by a Cbz group, along with BOP-Cl and DIEA to form an N- and C-protected MeLeu-MeVal dipeptide.

STEP 12

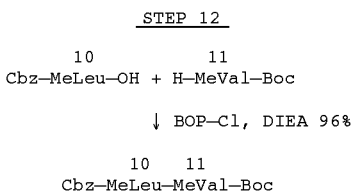

Thirteenth, the N- and C-protected dipeptide was N-deprotected by catalytic hydrogenation.

STEP 13

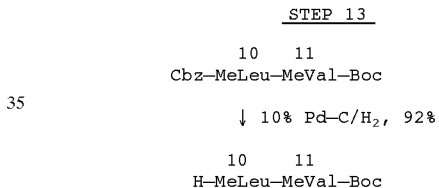

Fourteenth, the C-protected dipeptide was reacted with a methylleucine amino acid (MeLeu), N-protected by a Cbz group, along with BOP-Cl and DIEA to form an N- and C-protected MeLeu-MeLeu-MeVal tripeptide.

Step 14

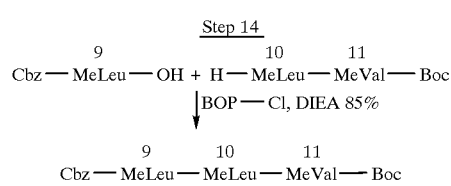

Fifteenth, the N- and C-protected tripeptide was N-deprotected by catalytic hydrogenation.

Step 15

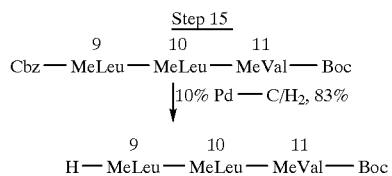

Sixteenth, the C-protected tripeptide was reacted with a D-alanine amino acid, N-protected by an Fmoc group, along with BOP-Cl and DIEA to form an N- and C-protected D-Ala-MeLeu-MeLeu-MeVal tetrapeptide (SEQ ID:NO 2).

Step 16

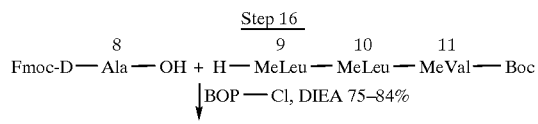

-continued

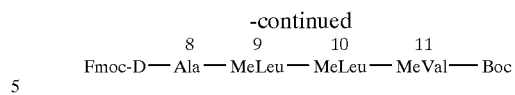

Seventeenth, the N- and C-protected tetrapeptide (SEQ ID:NO 2) was C-deprotected by reaction with trifluoroacetic acid.

Step 17

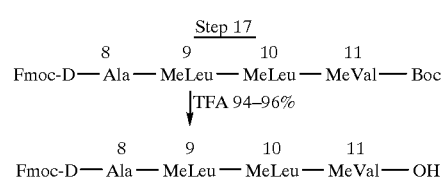

Eighteenth, the C-protected heptapeptide (SEQ ID:NO 5) from the eleventh step was reacted with the (D)-alanine-methylleucine-methylleucine-methylvaline tetrapeptide (SEQ ID:NO 2) (D-Ala-MeLeu-MeLeu-MeVal) from the seventeenth step, N-protected by 9-fluorenylmethoxycarbonyl (Fmoc), along with BOP-Cl and NMM to form an N and C-protected D-Ala-MeLeu-MeLeu-MeVal-MeLeu(3-OH)-Abu-Sar-MeAla-Val-MeAla-Ala undecapeptide (SEQ ID:NO 6).

Step 18

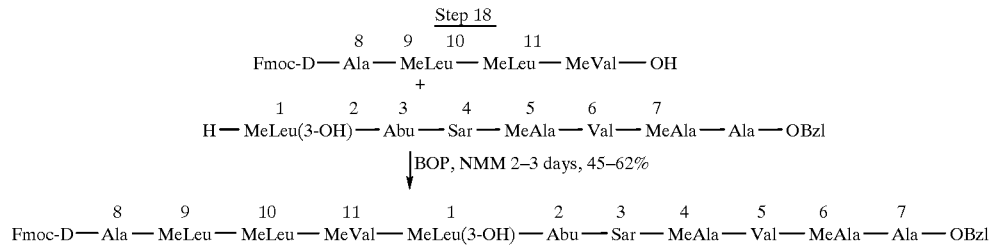

Nineteenth, the N- and C-protected D-Ala-MeLeu-MeLeu-MeVal-MeLeu(3-OH)-Abu-Sar-MeAla-Val-MeAla-Ala undecapeptide (SEQ ID:NO 6) was cyclized by reaction with aqueous sodium hydroxide, ethanol, 4-dimethylaminopyridine (DMAP) and propyl-phosphonic anhydride (Pr-PO$_2$)$_3$ to form the cyclosporin analog (SEQ ID:NO 21).

Step 19

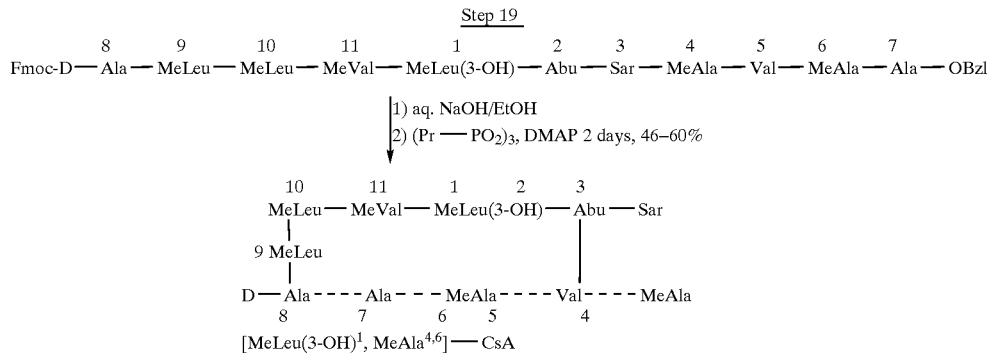

V. Solid Phase Synthesis Methods for the Generation of Compounds Containing Sterically Hindered Amino Acid Residues Previously, the solid phase synthesis of CsA and CsA analogs has been hampered because conventional solid phase synthesis procedures often result in incomplete couplings. Though a precise understanding of the underlying mechanism is not required in order to practice the present invention, difficult couplings on solid supports are sequence-dependent and have been ascribed to interchain interactions and/or poor solvation, resulting in limited accessibility to the amino group of the growing peptide chain (J. P. Tam et al., in *Peptides, Structure and Function*, C. M. Deber et al. (eds), Pierce Chemical Co., Rockford, Ill., pp. 423–425 [1985]). The present invention contemplates unique methods for the solid phase synthesis of CsA analogs and other compounds containing sterically hindered amino acid residues. These methods allow, e.g., for the efficient coupling of the seven sterically hindered N-methyl amino acids of CsA (See FIG. 1).

As described further below, the present invention contemplates the utilization of particular solid supports, linkers, and reaction conditions to overcome the coupling problem. The methods are particularly contemplated for facilitating the coupling of the amino acid residue that will form the 11-position (e.g., MeVal) of a CsA analog to the 1-position (e.g., MeLeu) of that analog (see, e.g., FIG. 14). It is to be understood that while the methods of the present invention are disclosed in the context of the synthesis of cyclosporin analogs, the methods may be used to facilitate couplings of sterically-hindered N-alkyl amino acids (e.g., N-methyl amino acids) during solid phase synthesis of other peptides and molecules.

Solid Supports

The methods of the present invention preferably utilize a solid support comprising a resin containing "spacers" separating each site of attachment to the support. The use of resins with spacers provides more favorable conditions for solvent permeation (compared to, e.g., cross-linked microporous styrene beads and polyamide resins), thereby facilitating coupling efficiencies for the synthesis of difficult peptide sequences.

The preferred solid supports of the present invention include polyethylene glycol-polystyrene supports (PEG-PS). A number of PEG-PS supports are commercially available, including PEG-PS (PerSeptive Biosystems), TENTAGEL S® (Advanced Chemtech), and NOVASYN TG® (Calbiochem-Novabiochem). The present invention is not limited to PEG-PS resins; for example, the present invention contemplates the use of other resins comprising spacers that afford efficient coupling efficiencies.

Linkers

Peptides containing N-methyl amino acid residues are susceptible to hydrolysis when exposed to high concentration of acid (See, J. Urban et al., Int. J. Peptide Protein Res., 47:182 [1996]). Therefore, linkers which require a high concentration of TFA for peptide cleavage from the solid support are not preferred for the synthesis of CsA analogs or other peptides containing N-methyl amino acids.

To circumvent the hydrolysis problem, the present invention contemplates the use of mild acid-labile linkers and photolabile linkers to provide for the non-destructive cleavage of such peptides from the solid support. FIG. 18 depicts the chemical structures of several of the linkers contemplated for use with the present invention; the preferred conditions for cleavage from the solid support are set forth below each linker. The mild acid-labile linkers include, but are not limited to 4-(4-hydroxymethyl-3-methoxyphenoxy)-butyric acid (HMPB), 4-hydroxymethyl-3-methoxyphenoxyacetic acid (Linker H), HAL, and trityl linker. The most preferred linkers are Linker H, HAL, the photolabile linker, 4-hydroxymethylphenoxyacetic acid (PAC), and HMPB (See, FIG. 18).

Optimized Coupling Conditions

Several conditions are contemplated by the present invention for optimizing the coupling of sterically hindered amino acid residues to a solid support-bound peptide (these conditions may also be employed for coupling of unhindered amino acid residues). It should be noted that each of the conditions is not required in order to practice the methods of the present invention. However, as described in detail below, the coupling reactions of preferred embodiments of the present invention utilize both polar aprotic solvents and elevated temperatures.

First, the present invention contemplates the use of polar aprotic solvents (i.e., polar solvents lacking acidic hydrogens). Examples of polar aprotic solvents include, but are not limited to, N-methyl pyrrolidinone (NMP), dimethylacetamide (DMA), dimethylformamide (DMF), tetramethylurea, and dimethyl sulfoxide (DMSO) (See L. A. Carpino, J. Am. Chem. Soc., 115:4397 [1993]). A preferred polar aprotic solvent is NMP.

Second, the present invention contemplates the use of elevated temperatures. In preferred embodiments, coupling reactions are performed at temperatures ranging from about 40° C. to about 70° C., and more preferably from about 50° C. to about 70° C. Generally speaking, it is most preferred not to use temperatures exceeding the boiling point of the particular solvent being used (J. P. Tam et al., in *Peptides, Structure and Function*, C. M. Deber et al (Eds), Pierce Chemical Co.; Rockford, Ill., pp. 423–425 [1985]).

In some embodiments of the present invention, other reaction conditions are also employed. The addition of chaotropic reagents during coupling reactions aides in preventing the formation of deletion sequences. For example, during the syntheses of cyclosporin analogs, the inventors obtained amounts of a cyclic decapeptide in which the MeVal[11] residue of CsA was missing; the cyclic decapeptide was generated even though capping of unreacted amines with N-acetyl imidazole was performed at each step. Although the practice of the present invention does not require a precise understanding of why the deletion sequences were formed, it is believed that the 1-position amine group was reversibly blocked during capping with N-acetyl imidazole, but emerged to couple at later steps. Again, though the precise mechanism is not required in order to practice the present invention, the effect is presumably due to interchain interactions.

The addition of chaotropic reagents during coupling reactions allows for the efficient and complete capping of any unreacted amine, thus preventing the formation of deletion sequences. Chaotropic agents are believed to act by promoting the solubility of nonpolar substances in, for example, polar solvents. Chaotropic agents contemplated by the present invention include, but are not limited to, potassium thiocyanate (KSCN), lithium perchlorate, lithium bromide, and lithium chloride (See K. C. Pugh et al., Int. J. Peptide Res. 40:208 (1992]).

In addition, the present invention contemplates the use of mixed solvents (i.e., addition of another solvent to the main aprotic solvent) to facilitate difficult couplings. For example, 2,2,2-trifluorethanol (TFE), which swells the peptide-resin, (D. Yamashiro et al., Tetrahedron Lett. 18:1469 [1976]) and HFIP (hexafluoroisopropanol) (M. Narita et al., Bull. Chem. Soc. Jpn, 61:281 [1988]) or 2-pyrrolidinone, may be employed in addition to NMP.

As described in detail in the Experimental section, in some embodiments of the present invention, successful total synthesis of CsA analogs was achieved by the use of DIPCDI/HOAt as the coupling agent, NMP as a polar aprotic solvent, 60° C. reaction conditions, and the use of the chaotropic agent KSCN at the refractory coupling step (i.e., the addition of Fmoc-MeVal$^{11}$).

VI. On-Resin Cyclization of Stericaly Hindered Compounds

Previously, chemical synthesis of the immunosuppressive drug Cyclosporin A [CsA, cyclo(-MeBmt$^1$-Abu$^2$-Sar$^3$-MeLeu$^4$-Val$^5$-MeLeu$^6$-Ala$^7$-D-Ala$^8$-MeLeu$^9$- MeLeu$^{10}$-MeVal$^{11}$) where MeBmt=(4R)4-[(2'E)-butenyl]4, N diethyl-(L)-threonine]; (SEQ ID NO:1) has been achieved only in solution. The present invention contemplates the synthesis of analogs of CsA using only solid phase methods; that is, the methods are unique in that they allow "on-resin cyclization" of the CsA analogs.

According to the methods of the present invention, an amino acid to be incorporated into the CsA analog is coupled to a solid support-bound linker; the preferred supports and linkers are described above. The present invention contemplates anchoring to the solid support, through an appropriate linker, the amino acid residue that will correspond to various positions of the analog (e.g., seven-position or the three-position (i.e., Ala$^7$ or Sar$^3$) of the CsA analog). Thus, for example, onresin cyclization will be effected through 7→8 coupling or through 3→4 coupling.

In preferred embodiments, the amino acid is coupled to the linker through a suitably functionalized amino acid side-chain (e.g., the side chains of aspartic acid or glutamic acid). In this embodiment, the carboxylic acid group is protected as the ester, which is removed prior to on-resin cyclization. However, the amide backbone may be linked to the resin prior to on-resin cyclization. For side chain attachment to the resin, amino acids with functional groups such as carboxylic acid (e.g., aspartic acid, and glutamic acid), hydroxyl groups (e.g., serine, threonine, and tyrosine), thiols (e.g., cysteine), or amino groups (e.g., lysine and ornithine), can be linked to the resin.

For example, because Ala$^7$ of CsA can be replaced by other amino acids without eliminating either binding to cyclophilin or immunosuppressive activity (M.-K Hu et al., J. Med. Chem 38:4164 [1995]), Ala$^7$ may be replaced by Fmoc/O-allyl-protected aspartic acid to provide a point for attachment of the CsA analog to the resin. Of note, the 8-position of CsA analogs (D-Ala in "native" CsA) is associated with much of their utility. For example, the 8-position is critical for binding of many substituents, thus, substituents are frequently attached to that position. Thus, generally speaking, it is important in many cases for the 8-position to have adequate exposure during, for example, screening of combinatorial libraries.

The present invention contemplates the use of the Fmoc/Allyl orthogonal protection methods previously utilized for on-resin cyclization of other peptides (See, e.g., S. A. Kates et al., Tetrahedron Lett. 34:1549 [1993]; S. A. Kates et al., Anal. Biochem. 212:303 [1993]) (see Example 8). Briefly, an amino acid residue (possessing an Fmoc-protected N-amino group and an allyl-protected C-carboxyl group) is anchored via its side chain to a solid support. After removal of the Fmoc protecting group, the peptide is extended in the C-to-N direction using Fmoc-protected amino acids. Standard coupling conditions (e.g., excess DIPCDI/HOAt in DMF) may be used for all couplings prior to Fmoc-MeVal$^{11}$; however, as set forth above, the difficult coupling of Fmoc-MeVal$^{11}$ to the one-position residue is effected using a polar aprotic solvent (e.g., NMP) and elevated temperatures. Although the amino acids in positions 8–11 may be added using standard coupling conditions, the coupling conditions involving a polar aprotic solventlelevated temperature may afford more consistent results (see Example 8).

Prior to cyclization, orthogonal deprotection (using, e.g., Pd(PPh$_3$)$_4$, or any Pd species capable of removing the allyl ester group, and which can be solublized and separated from the resin) liberates the C-carboxyl group of the side chain-anchored amino acid residue, and the Fmoc group is cleaved (e.g., using standard cleavage conditions like DBU:piperidine:DMF) from the N-amino residue at the end of the linear peptide to allow for condensation with the C-carboxyl group of the side chain anchored residue. In preferred embodiments, Pd(PPH$_3$)$_4$ is used, as it can be solublized in the AcOH/NMM/CHCl$_3$ mixture, facilitating its easy separation from the resin by filtration.

Initial attempts at on-resin cyclization of linear precursors of CsA analogs using the standard protocol for cyclization of CsA analogs in solution (i.e., propyl phosphonic anhydride ((PrPO$_2$)$_3$, 1.5 eq]/DMAP (5 eq) for 72 hours; See R. M. Wenger, Helv. Chim. Acta 67:502 [1984]; W. J. Colucci et al., J. Org. Chem. 55:2895 [1990]) were unsuccessful. As a result, the present inventors developed new methods for the on-resin cyclization reaction. Specifically, the present invention contemplates on-resin cyclization of linear precursors of CsA analogs using BOP/HOBt/DIEA in DMF. In preferred embodiments, on-resin cyclization is effected with BOP (5 eq)/HOBt (5 eq)/DIEA (10 eq) in DMF for 72 hours. It is contemplated that other reagents, including but not limited to PyAOP/HOAt/DIEA in NMP will be used, in ratios ranging from 2 to 6 equivalents.

As set forth in detail in the Experimental section, the methods of the present invention have been employed in the synthesis and on-resin cyclization of [MeLeu$^1$, Asp$^7$]CsA (SEQ ID NO:28)(i.e., MeLeu$^1$-Abu$^2$-Sar$^3$-MeLeu$^4$-Val$^5$-MeLeu$^6$-Ala$^7$-D-Asp$^8$-MeLeu$^9$-MeLeu$^{10}$-MeVal$^{11}$, wherein "MeLeu" is N-methylleucine). It should be emphasized that the methods of the present invention are not limited to the generation of particular analogs of CsA; the methods may be used in the cyclization of any analog of CsA. FIG. 19 indicates the chemical structure of some of the CsA analogs that may be generated using the on-resin cyclization procedures of the present invention. Moreover, the present invention also contemplates the use of the methods to perform on-resin cyclization of other compounds (e.g., other peptides and small organic molecules). In preferred embodiments, the methods are utilized to synthesize peptides.

Though neither limited by the number of amino acid residues nor the characteristics thereof (e.g., whether the amino acid residues are natural or modified), preferred embodiments of the present invention contemplate cyclization of peptides containing 4–20 amino acids, and more preferably 4–13 amino acids.

The total synthesis of cyclosporin analogs by solid phase methods has accelerated the production of CsA analogs from months using solution phase techniques to merely a matter of days. The ability to perform on-resin cyclization of compounds like CsA analogs has tremendous utility in that it will expedite efforts to synthesize those compounds in a combinatorial fashion and facilitate the screening of resin-bound CsA analogs for new activities (See e.g., S. P. Bartz et al., Proc. Natl. Acad. Sci. USA, 92:5381 [1995]). When one considers that there are conservatively approximately $10^{12}$ possible amino acid combinations for CsA analogs (ie., if only natural amino acid residues and residues with the same optical activity are used), the need for on-resin screening is clear.

VII. Solid Phase Synthesis for Generation of Combinatorial Libraries

Combinatorial chemistry has become a powerful tool for drug discovery in the pharmaceutical and biotechnology industries. Generally speaking, combinatorial chemistry is defined as the repetitive and systematic covalent attachment of different structural moieties to one another to produce numerous distinct molecular entities or target molecules (i.e., combinatorial libraries); desired target molecules include peptides, oligonucleotides, and small organic molecules. Frequently, combinatorial chemistry is utilized to generate a group of structurally related analogs which can then be evaluated to establish structure-activity relationships (SAR) and to optimize biological potency. (See, e.g., M. A. Gallop et al., J. Med. Chem., 37:1233–1248 [1994]).

Solid supports (e.g., polystyrene resin beads and silica chips) and, concomitantly, solid phase synthesis techniques are routinely utilized in generating and screening combinatorial libraries. Indeed, the use of automated, high throughput techniques allows for the practical and efficient screening of hundreds of thousands of distinct compounds directed to a specific drug target. Unfortunately, it is difficult, if not impossible, to generate certain compounds through traditional solid phase synthesis methods because of, for example, the secondary and/or tertiary structure of those compounds. Instead, the synthesis of these compounds must either take place i) in solution in its entirety, or ii) initially through solid phase synthesis methods and subsequently in solution.

In contrast to the presently used methods, the invention provides methods for the efficient synthesis of compounds (e.g., cyclosporin) using solid phase synthesis techniques. It is further contemplated that the method will provide means for the screening of compounds while they are still tethered to the support.

Experimental

The following examples serve to illustrate certain preferred embodiments and aspects of the present invention and are not to be construed as limiting the scope thereof.

In the experimental disclosure which follows, the following abbreviations apply: equiv (equivalents); N (normal); M (Molar); mM (millimolar); μM (micromolar); g (grams); mg (milligrams); μg (micrograms); kg (kilograms); L (liters); mL (milliliters); μL (microliters); cm (centimeters); mm (millimeters); μm (micrometers); nm (nanometers); min. (minutes); h and hr (hours); s and sec. (seconds); Cbz (carbobenzyloxycarbonyl); MeBmt ([(4R)-N-methyl-4-butenyl-4-methyl-L-threonine]; Abu (α-aminobutyric acid); MeLeu(3-OH) (3-hydroxy-N-methylleucine); Sar (sarcosine); MeAla (N-methylalanine); Gly (glycine); Ala (alanine); Val (valine); Leu (leucine); Ile (isoleucine); Met (methionine); Pro (proline); Phe (phenylalanine); Trp (tryptophan); Ser (serine); Thr (threonine); Cys (cysteine); Tyr (tyrosine); Asp (asparagine); Gln (glutamine); Asp (aspartic acid); Glu (glutamic acid); Lys (lysine); Arg (arginine); His (histidine); Fmoc (9-fluorenylmethoxycarbonyl); HOBt (1-hydroxybenzotriazole); BOP-Cl (bis(2-oxo-3-oxazolidinyl) phosphonic chloride); NMM (N-methyl morpholine); PyAOP (7-azabenzotriazole-1-yl oxytris (pyrodidino) phosphonium hexafluorophosphate); DCU (dicyclourea); DIEA (diisopropylethylamine); DCC (dicyclohexyl carbodiimide); DMAP (4-dimethylaminopyridine); (Pr-PO2)$_3$ (propyl-phosphonic anhydride); TFA (trifluoroacetic acid); OBzl and OBn (benzyl ester); Cbz (carbobenzyloxy); PyBroP (bromotripyrrolidino-phosphonium hexafluorophosphate); EtOAc (ethyl acetate); DIPCDI (diisopropylcarbodiimide); HATU (O-(7-azabenzotriazol-1-yl)-1,1,2,2,-tetramethyluronium hexafluorophosphate); NMR (Nuclear Magnetic Resonance Spectroscopy); FABMS (Fast Atom Bombardment Mass Spectrometry); hsp70 (Heat Shock Protein); MeVal (N-methylvaline); Boc (t-butoxycarbonyl); DMF (dimethylformamide); THF (tetrahydrofuran); HFIP (hexafluoroisopropanol); MeLeu (N-methylleucine); MeOH (methanol); PHA (phytohemagglutinin); BOP (benzotriazolyl-N-oxy-tris(dimethylamino)phosphonium hexafluorophosphate); NMP (N-methyl pyrrolidinone); DMA (N,N-dimethylacetamide); DMSO (dimethyl sulfoxide); KSCN (potassium thiocyanate); HOAc (acetic acid); EtOH (ethanol); Et$_3$N (triethylamine); CH$_2$Cl$_2$ (dichloromethane); CDCl$_3$ (deuterated form of chloroform; PS (polystyrene); PEG (polyethylene glycol); HOAt (hydroxyazabenzotriazole); GC/MS (gas chromatography/ mass spectroscopic analysis); HRFAB-MS (high resolution fast atom bombardment mass spectroscopy); RP-HPLC (reversed phase-high pressure liquid chromatography); LSIMS (liquid secondary ion mass spectrometry); TLC (thin layer chromatography); Advanced ChemTech (Louisville, Ky.); Aldrich (Aldrich Chemical Company, Milwaukee, Wis.); Calbiochem-Novabiochem (San Diego, Calif.); Millipore (Bedford, Mass.), PerSeptive Biosystems (Framingham, Mass.); Amersham (Amersham Life Science, Inc., Arlington Heights, Ill.); Novagen (Novagen, Inc., Madison, Wis.); Sandoz (Sandoz, Inc., East Hanover, N.J.); Sigma (Sigma Chemical Co., St. Louis, Mo.).

EXAMPLE 1

Synthesis of CsA Analogs

Figure 4:
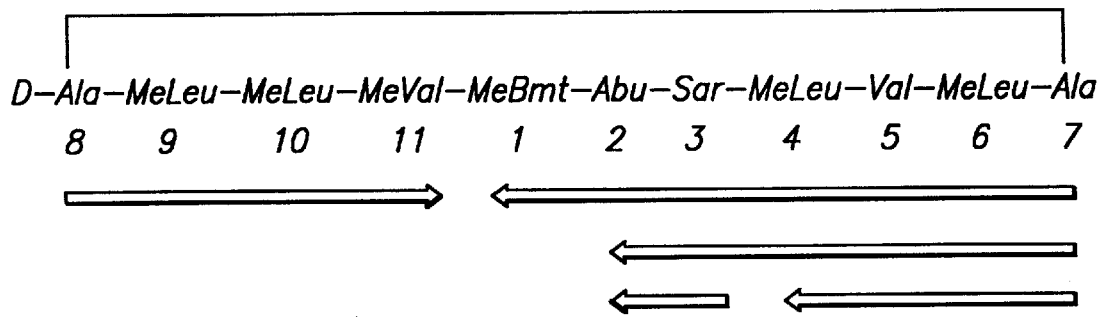
FIG. 4 is a schematic outlining a synthetic strategy used to synthesize Cyclosporin analogs (SEQ ID NO:1).

The total synthesis of CsA was first reported by Wenger (Helv. Chim. Acta 67:501 [1984], supra). The strategy followed a route in which CsA was built up in the direction of the arrows in FIG. 4 (SEQ ID:NO 1). The point of cyclization was chosen at the peptide bond between the Ala$^7$ and (D)-Ala$^8$ for the following two reasons: 1) both amino acids do not have an N-methyl group, presenting an easier bond formation, as compared to N-methyl amino acids; and 2) intramolecular H-bonds might be present in the linear undecapeptide, stabilizing the linear undecapeptide in a folded conformation and thus facilitate ring closure. For the synthesis of the linear undecapeptide, a technique of fragment coupling between the tetrapeptide (residues 8–11) (SEQ ID:NO 2) and the heptapeptide (residues 1–7) (SEQ ID.NO 10) was chosen. The heptapeptide fragment (SEQ ID:NO 10) was prepared by a fragment coupling of the dipeptide (residues 2–3) and the tetrapeptide (residues 4–7) (SEQ ID:NO 22), followed by introduction of the amino acid MeBmt at the end of the synthesis (note that in the preferred analog this amino acid was replaced by the novel amino acid MeLeu(3-OH)). This sequence had two obvious advantages: 1) fragment coupling onto the sarcosine (residue 3) prevented the possibility of racemization; and 2) the number of steps after the introduction of the precious 1-position amino acid was minimized. The undecapeptide could be cyclized to CsA after removal of N- and C-terminal protecting groups.

Figure 10:
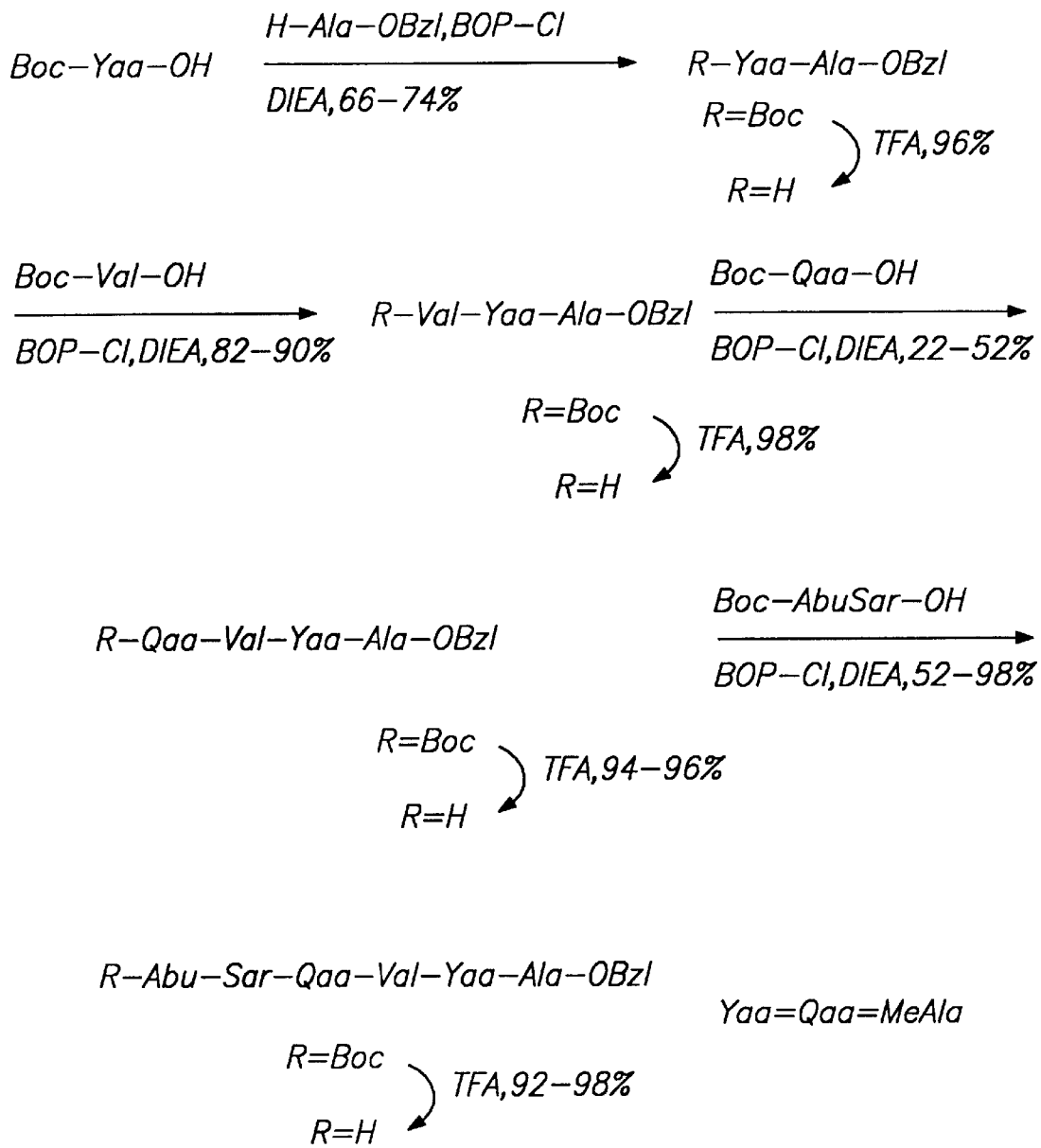
FIG. 10 depicts a method of synthesizing CsA 2–7 analogous fragments (SEQ ID NOS:3, and 4).

The synthesis of (MeLeu(3-OH)$^1$)CsA analogs modified at residues 3–8 was carried out as originally described. (See, Colucci, W. J., Tung, R. D., Petri, J. A. and Rich, D. H., J. Org. Chem. 55:2895 [1990]). The CsA 2–7 tetrapeptides were constructed starting from H-Ala-OBzl and adding the appropriate amino acids in a step-by-step series of coupling-deprotection procedures (FIG. 10) (SEQ ID:NOS 3, 4). After deprotection of N-terminal Boc group, the resultant tetrapeptides were condensed with Boc-AbuSar-OH using the BOP-Cl/DIEA method to provide the hexapeptides. After removal of the N-Boc group with TFA, the corresponding amino-hexapeptides were obtained and quickly used for further reactions. The optical rotations and yields of the peptide fragrnents for BOP-Cl mediated couplings and Ndeprotections are summarized in Tables 1 and 2 (SEQ ID:NOS 3, 22–26).

TABLE 1

BOP—Cl Coupling of N-Protected Amino Acids With Segments of the 2–7 Peptides

| Compound | Product Sequence | $[\alpha]_D$(CHCl$_3$) | Yield (%) |
|---|---|---|---|
| 1 | BocMeLeu—AlaOBzl | −67.0° (1.0) | 74 |
| 2 | BocMeAla—AlaOBzl | −65.2° (1.5) | 66 |
| 3 | BocVal—MeLeuAlaOBzl | −97.2° (1.0) | 76 |
| 4 | BocVal—MeAlaOBzl | −86.0° (1.7) | 90 |
| 5 | BocMeLeu—ValMeLeuAlaOBzl (SEQ ID NO:22) | −126.7° (1.0) | 95 |
| 6 | BocMeLeu—VMeAlaOBzl (SEQ ID NO:23) | −136.0° (0.82) | 24 |
| 7 | BocMeAla—ValMeAlaAlaOBzl (SEQ ID NO:3) | −116.0° (0.9) | 22 |
| 8 | BocAbuSar—MeLeuValMeLeuAlaOBzl (SEQ ID NO:24) | −128.1° (1.0) | 56 |
| 9 | BocAbuSar—MeLeuValMeAlaAlaOBzl (SEQ ID NO:25) | −124.8° (0.5) | 92 |
| 10 | BocAbuSar—MeAlaValMeAlaAlaOBzl (SEQ ID NO:26) | −128.0° (0.7) | 98 |

The line (—) indicates site of new peptide bond formed from acid-amine coupling.

TABLE 2

Optical Rotation and Yields of Aminopeptide Fragments

| Compound | Product Sequence | $[\alpha]_D$(c,CHCl$_3$) | Yield (%) |
|---|---|---|---|
| 1 | H—MeLeuAlaOBzl | −44.5° (1.0) | 96 |
| 2 | H—MeAlaAlaOBzl | −24.8° (0.66) | 96 |
| 3 | H—ValMeLeuAlaOBzl | −102.0° (1.0) | 98 |
| 4 | H—ValMeAlaAlaOBzl | −45.4° (1.2) | 98 |
| 5 | H—MeLeuValMeLeuAlaOBzl (SEQ ID NO:22) | −130.9° (1.0) | 99 |
| 6 | H—MeLeuValMeAlaAlaOBzl (SEQ ID NO:23) | −101.0° (1.1) | 94 |
| 7 | H—MeAlaValMeAlaAlaOBzl (SEQ ID NO:3) | −112.0° (0.95) | 96 |
| 8 | H—AbuSarMeLeuValMeLeuAlaOBzl (SEQ ID NO:24) | −108.9° (1.27) | 92 |
| 9 | H—AbuSarMeLeuValMeAlaAlaOBzl (SEQ ID NO:25) | −126.7° (0.12) | 96 |
| 10 | H—AbuSarMeAlaValMeAlaAlaOBzl (SEQ ID NO:26) | −102.2° (0.9) | 98 |

Figure 9:
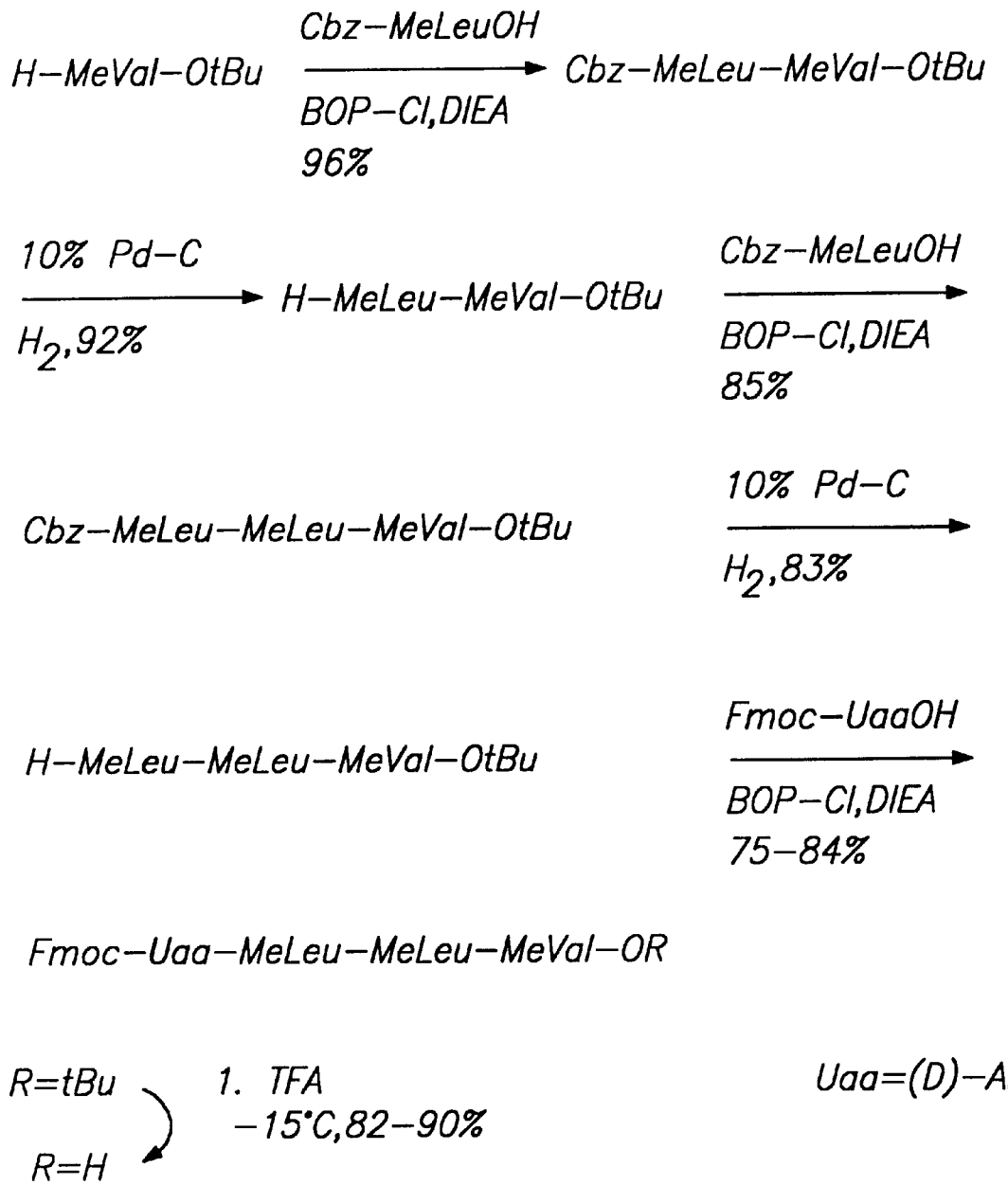
FIG. 9 depicts a method of synthesizing (MeLeu(3-OH)$^1$)CsA (SEQ ID NO:2).
Figure 11:
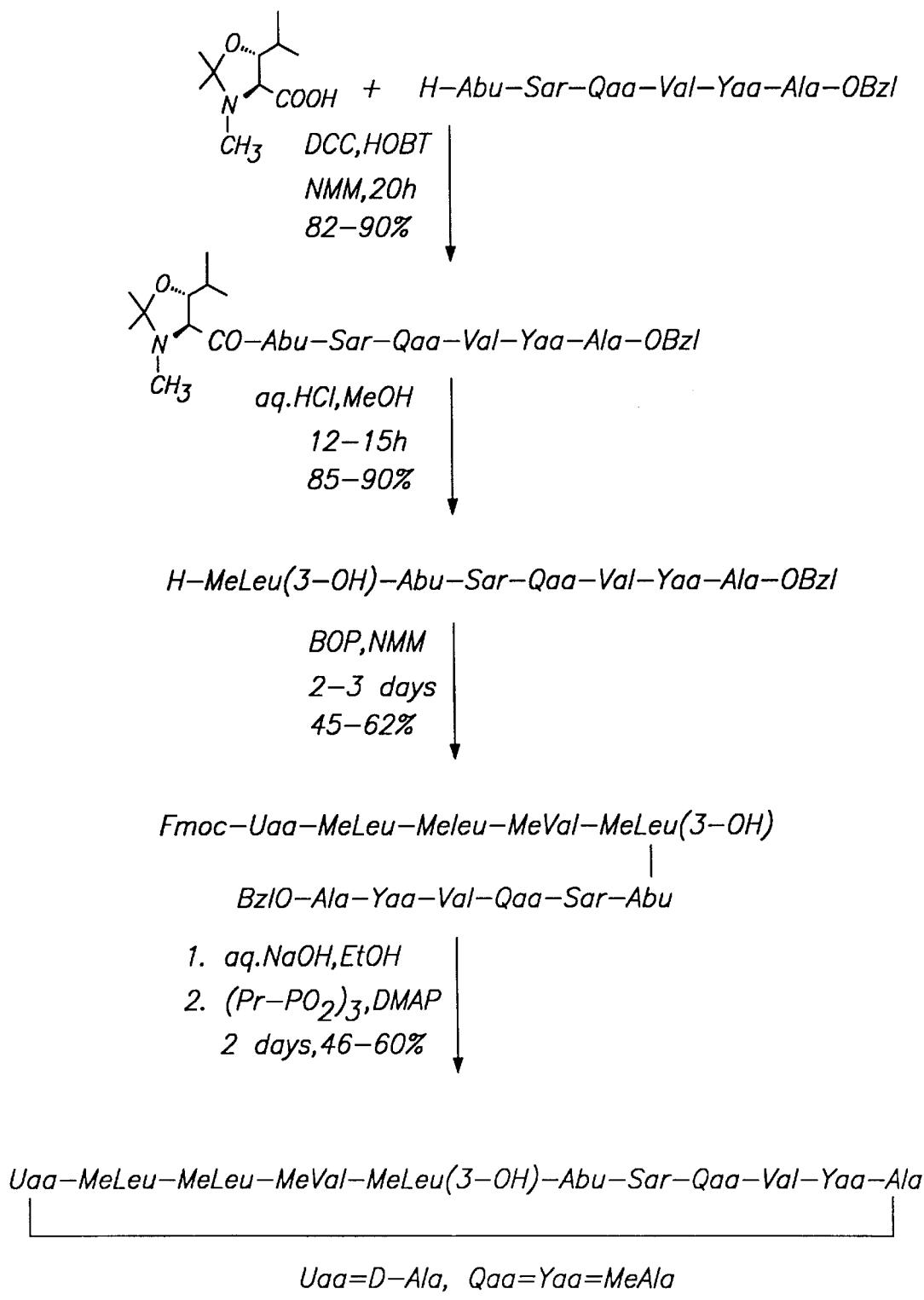
FIG. 11 depicts a method of synthesizing CsA 8–11 analogous fragments (SEQ ID NOS:4–7).

The available hexapeptides were then acylated with the acetonide-protected MeLeu(3-OH) using DCC/HOBt method to give desired protected heptapeptides (82–90%), as shown in FIG. 9 (SEQ ID:NO 2). These heptapeptides appear as two major conformers in CDCl$_3$ by NMR due to the N-methyl amide conformers. Removal of the acetonide protecting group of the heptapeptides was performed using 1M HCl in methanol for 15 hours. The resultant amino-heptapeptides were purified by flash chromatography (85–90%). The CsA 8–11 tetrapeptides were constructed starting from H-MeVal-Boc and adding the appropriate amino acids step-by-step in a series of coupling-deprotection procedures (FIG. 11) (SEQ ID:NOS 5–7). Tung et al., (Tung et al., J. Org. Chem., 51:3350 [1986]) provide a more detailed procedure. For the coupling of the CsA 8–11 tetrapeptides and heptapeptides, Castro's BOP-Cl reagent and N-methyl morpholine were employed to achieve these linkages. The resultant undecapeptides were obtained usually in relatively low yields, 45–62%, as compared to the 73% reported by Wenger in the case of CsA synthesis. (See, Wenger, R. M. Helv. Chim. Acta 67:501 [1984]).

Figure 12:
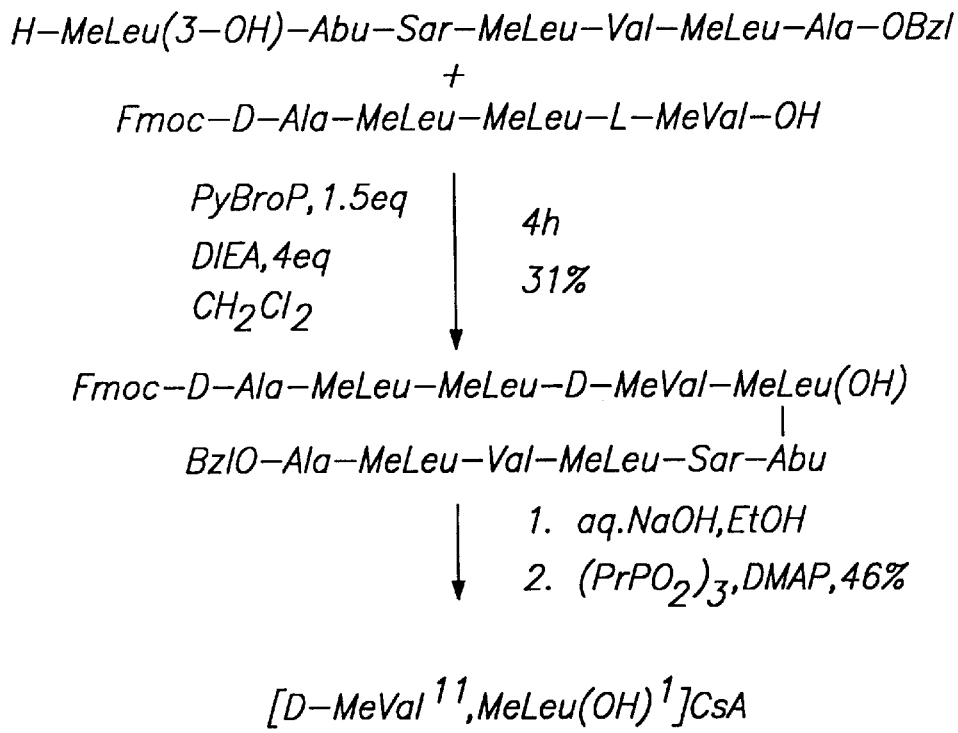
FIG. 12 depicts the PyBroP Mediated 4+7 coupling reaction (SEQ ID NOS:2, 8, and 9).

Recently, a type of pyrrolidinophosphonium complexes abbreviated as PyBroP (bromotripyrrolidino-phosphonium hexafluorophosphate), PyCloP, and PyBoP were reported as coupling reagents for peptide synthesis. (See, Coste, J., Frerot, E., Joulin, P. and Castro, B., Tetrahedron Lett. 32:1967 [1991]). According to Castro's report, N-methyl amino acids could be coupled efficiently by using PyBroP/DIEA. Because of the low yield for the 4+7 coupling for the synthesis of undecapeptides, PyBroP (1.5 equiv) was used in the attempted coupling of the tetrapeptide (1.5 equiv) and the heptapeptide in the presence of DIEA (4 equiv), as shown in FIG. 12.

As expected, PyBroP did drive the coupling reaction to completion in 4 hours. However, PyBroP also gave multiple spots by TLC and did not improve the yield of product (only 32%). The unexpected result was that the epimerized undecapeptide (with (D)-configuration at residue MeVal) was obtained as the major product. Racemization was presumably due to the formation of hydrobromide during the activation of the carboxylic group of tetrapeptide with PyBroP, which could cause C-terminal residue [MeVal$^{11}$] to epimerize. (*The Peptides: Analysis, Synthesis, Biology* (Vol. 1) Academic Press, Inc. [1979]).

Figure 13:
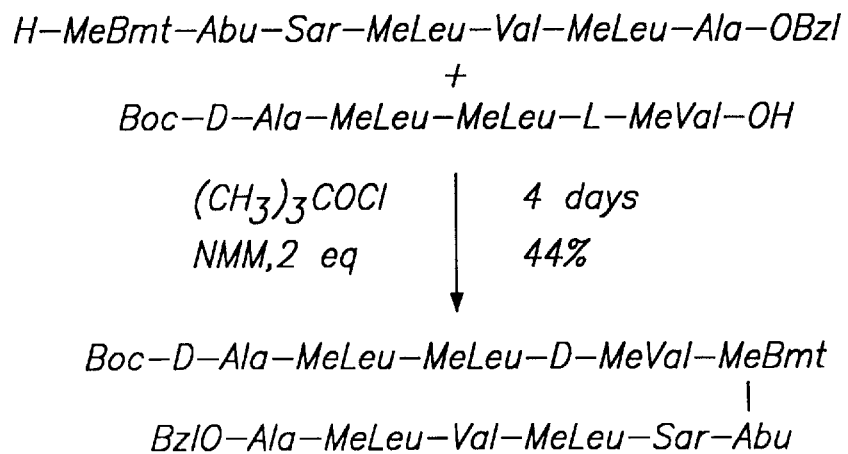
FIG. 13 depicts inverted conversion in 4+7 coupling as reported by Wenger (Helv. Chim Acta 67:501 [1984]) (SEQ ID NOS:2, 10, and 11).

A similar result has been reported by Wenger (discussed supra) (see FIG. 13), in which the mixed pivalic anhydride method (using pivaloyl chloride/N-methylmorpholine), gave the configuration-inverted (at MeVal) undecapeptide (SEQ ID:NO 11) Boc-(D)-Ala-MeLeu-MeLeu-(D)-MeVal-MeBmt-Abu-Sar-MeLeu-Val-MeLeu-Ala-OBzl when coupling the tetrapeptide (SEQ ID:NO 2) Boc-(D)-Ala-MeLeu-MeLeu-L-MeVal-OH with the corresponding heptapeptide. In both cases, epimerization may be due to high halide concentrations in the reaction media.

Although it took 3 days to complete the coupling reaction, the BOP-Cl reagent is still preferable for the 4+7 fragment coupling in the synthesis of CsA analogs, since racemization of MeVal is minimized. In order to complete the final cyclization, the N-Fmoc and C-Bzl protecting groups of the undecapeptides were removed simultaneously by reaction with 0.2N of aqueous NaOH in ethanol for 5–12 hours. (See FIG. 11). After workup, the crude, fully-deprotected undecapeptides (SEQ ID:NOS 5–7) were cyclized, using propylphosphonic anhydride (1.5 equiv) and DMAP (6 equiv), in a dilute solution (~2×10$^{-4}$M) for 2 days to give CsA analogs in 37–60% yields.

The physical properties of these CsA analogs and their linear undecapeptide intermediates are summarized in Table 3.

TABLE 3

Physical properties of CsA analogs and their linear undecapeptide intermediates

| Compound | Structure[b] | R$_f$ (%)[a] | [α]$_D$(c,CHCl$_3$) | Yield (%) |
|---|---|---|---|---|
| 1 | [MeL(OH)$^1$] | 0.53(50) | −102.1° (0.73) | 62 |
| 2 | [MeL(OH)$^1$,MeA$^6$] | 0.49(50) | −122.0° (0.2) | 56 |
| 3 | [MeL(OH)$^1$,MeA$^{4,6}$] | 0.67(60) | −146.7° (0.02) | 34 |
| 4 | [MeL(OH)$^1$,D—Lys(Boc)$^8$] | 0.31(50) | −133.1° (1.9) | 62 |
| 5 | [MeL(OH)$^1$,D—MeVal$^{11}$] | 0.71(40) | −103.2° (2.5) | 32 |
| 6 | [MeL(OH)$^1$] | 0.49(50) | −200.0° (0.04) | 41 |
| 7 | [MeL(OH)$^1$,MeA$^6$] | 0.34(40) | −215.0° (0.2) | 56 |
| 8 | [MeL(OH)$^1$,MeA$^{4,6}$] | 0.53(60) | −247.5° (0.05) | 69 |
| 9 | [MeL(OH)$^1$,d-Lys(Boc)$^8$] | 0.47(50) | −182.5° (0.04) | 74 |
| 10 | [MeL(OH)$^1$,D—MeVal$^{11}$] | 0.54(50) | −162.5° (0.04) | 46 |

[a]TLC (% acetone/hexane).
[b]Abbreviated symbol: A = Ala; L = Leu.

EXAMPLE 2

General Synthetic Procedures

General Procedure A:

Synthesis of β-Hydroy-N methylleucine (MeLeu(OH))

Figure 5:
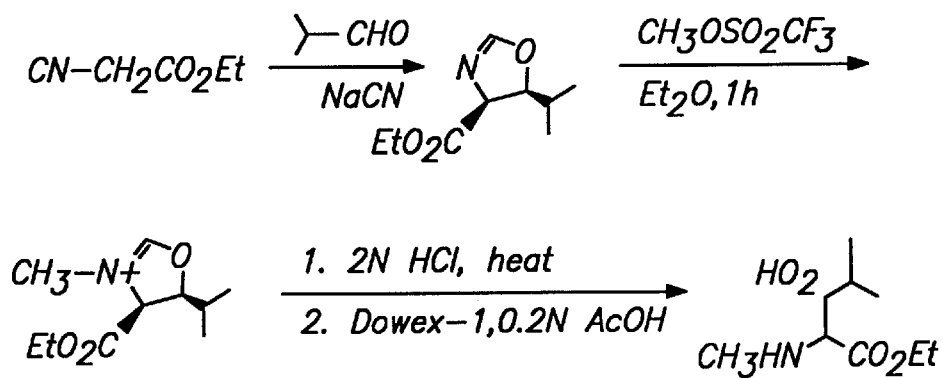
FIG. 5 depicts the synthesis of (±)-threo-β-hydroxy-N-methylleucine.

A synthesis scheme for MeLeu(3-OH) has been reported (See, Rich, D. H., Dhaon, M. K, Dunlap, B. and Miller, S. P. F, J. Med. Chem., 29:978 [1986]) in which the procedure developed by Schöllkopf [see U. Angew. Chem. Int. Ed., 16:339 [1977]) for the synthesis of β-hydroxy amino acids was employed (FIG. 5). The reaction of isocyanoacetate with isobutyraldehyde in the presence of NaCN gave the thermodynamically stable trans-oxazoline as the major product. The trans-oxazoline was treated with methyl triflate at room temperature to give the N-methyl imidate. Hydrolysis of the N-methyl imidate with dilute HCl followed by ion-exchange chromatography of the amino acid gave (±)-threo-β-hydroxy-N-methylleucine.

Figure 7A:
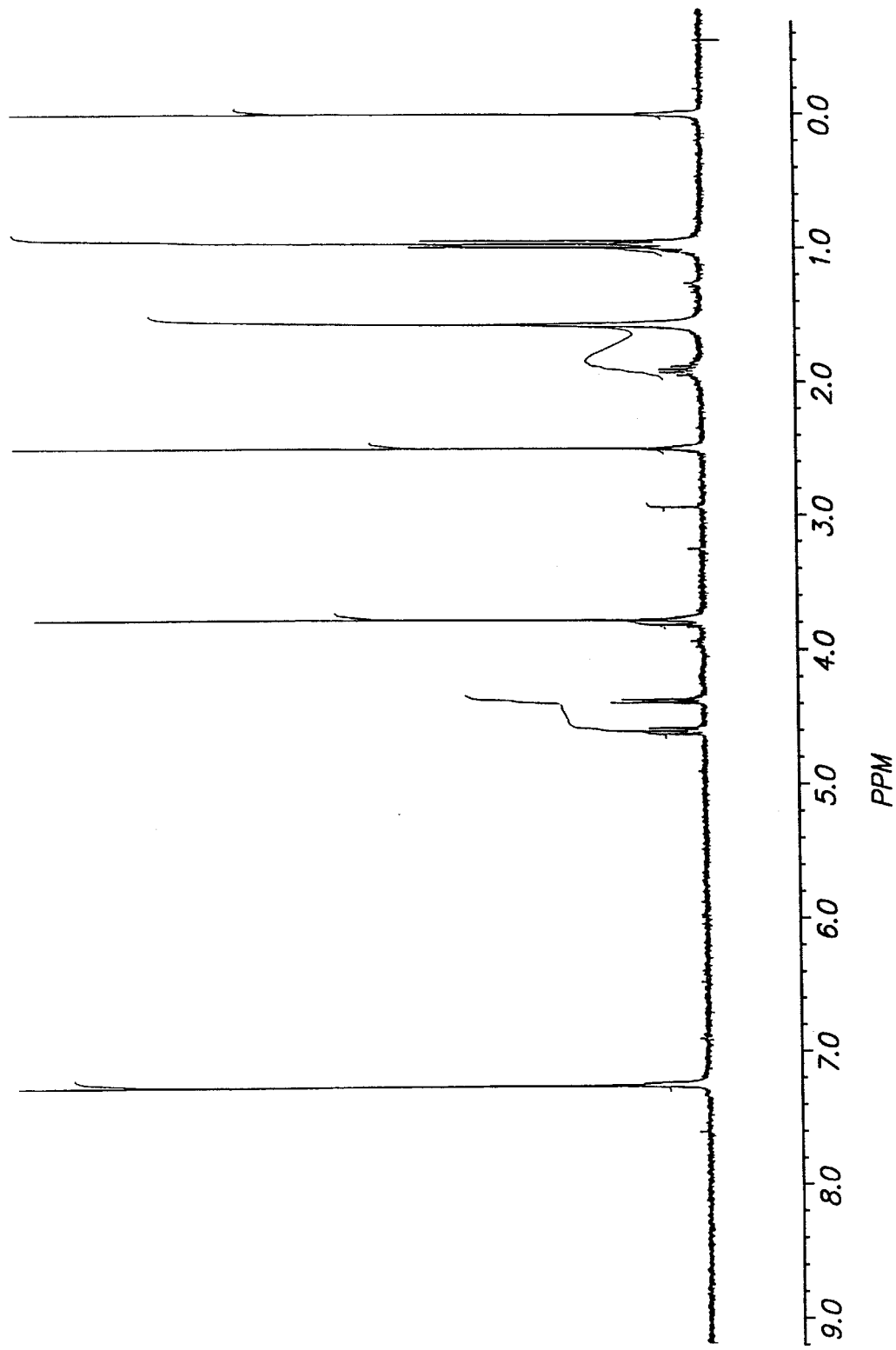
FIG. 7A depicts the $^1$H NMR spectra of one of the oxazolidinone epimers.
Figure 7B:
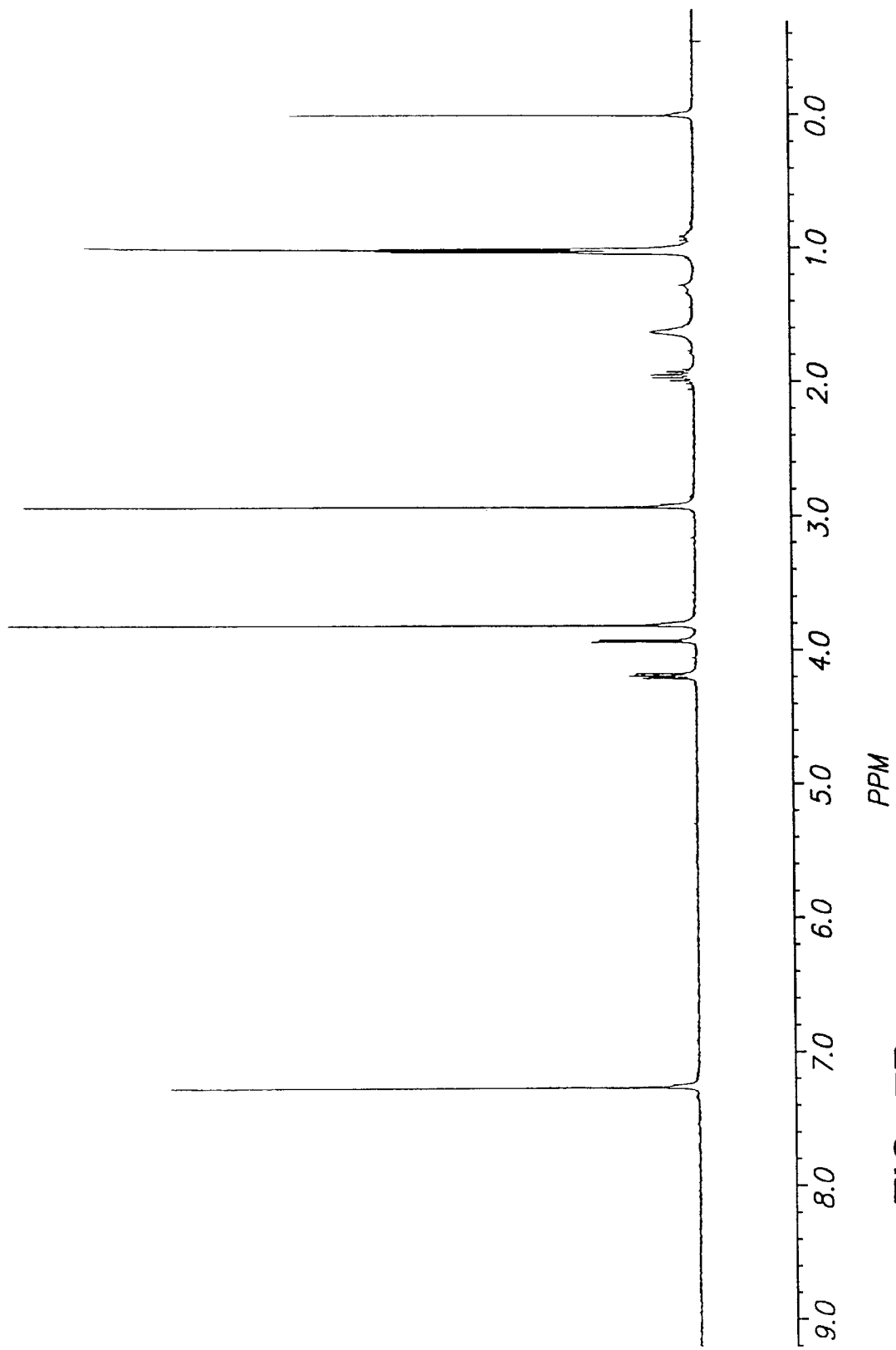
FIG. 7B depicts the $^1$H NMR spectra of the other oxazolidinone epimer.
Figure 8:
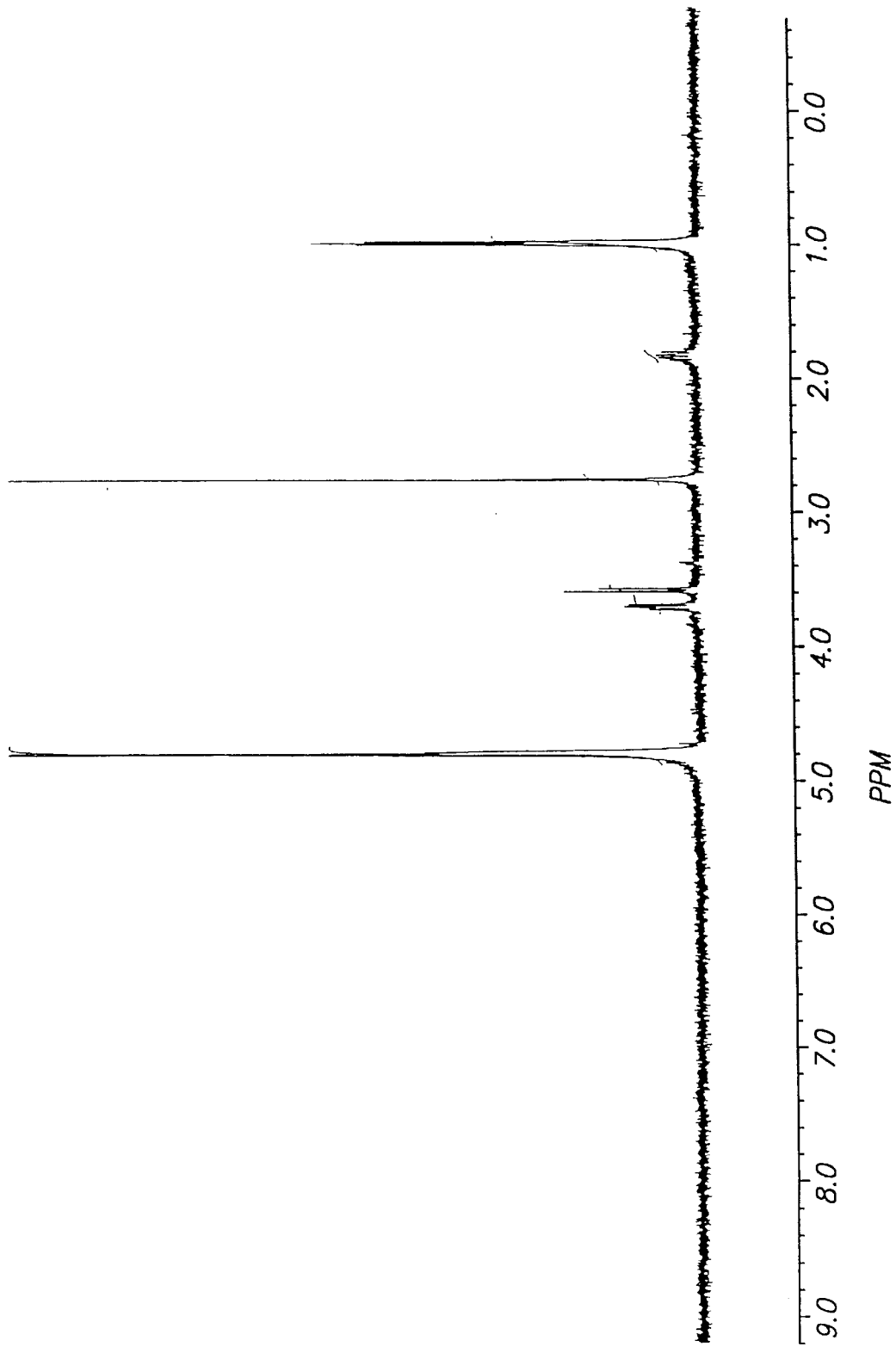
FIG. 8 depicts the $^1$H NMR spectra of β-hydroxy-N-methylleucine.

At the same time, an elegant asymmetric glycine enolate reaction was developed by Evans and Weber for the synthesis of MeBmt and other chiral amino acids. (See, Evans, D. A. and Weber, A. E., J. Am. Chem. Soc., 108:6757 [1986]). The approach was also applied to prepare MeLeu (OH) (See, FIG. 6). In the reaction sequence, the chiral glycine synthon isothiocyanate was obtained from corresponding chloroacetate and followed by azide replacement in 56% yield. The isothiocyanate chiral auxiliary was condensed with isobutyraldehyde under stannous triflate-mediated aldol reaction (−78° C. for 4 h) to give the aldol adduct in 63% yield (>90% e.e). Transesterification with a solution of magnesium methoxide in methanol at room temperature for 3 min gave the methyl ester in 78–82% yield. The yield of the bis-methylation was low, 52% as compared to 76% of Evans in MeBmt synthesis. Two epimers are usually obtained in a ratio of 1:5, which was not found by Evans for the MeBmt synthesis. The $^1$H NMR spectra of the epimers were compared as shown in Table 4 and FIG. 7. Hydrolysis of the desired trans-oxazolidinone with 2N KOH under reflux gave the pure β-hydroxy-N-methylleucine (see $^1$H NMR spectra in FIG. 8) after chromatographic purification over Sephadex LH-20.

TABLE 4

Chemical Shifts of Oxazolidinone Diastereomers

| | Chemical Shift δ (Coupling Constant J) | | | |
|---|---|---|---|---|
| Oxazolidinone | H-4 | H-5 | N—Me | O—Me |
| erythro- | 4.39 (d, J = 6.7) | 4.61 (t, J = 6.7) | 2.48 | 3.78 |
| threo- | 3.94 (d, J = 4.8) | 4.21 (dd, J = 4.8, 6.7) | 2.92 | 3.82 |

General Procedure B:
Synthesis of CsA Tetrapeptide Fragment 8-11 (SEQ ID NO:2)

A solution of the eleven-position amino acid (3.01 g, 13 mmol) in 20 mL of dioxane was reacted with 4.95 g (26 mmol) of p-toluenesulfonic acid monohydrate and heated under reflux for 40 min ($CaCO_3$ drying tube). The mixture was cooled in an ice/water bath, then transferred to a thick-walled pressure flask, and treated with 25 mL of isobutylene previously condensed at 78° C. The flask was capped and vigorously stirred at room temperature for 19 hr. chilled and uncapped, and the contents were poured into cold dilute aqueous NaOH. The mixture was adjusted to pH=10, then extracted with ether (2×25 mL). The organic layers were combined, dried and evaporated and the residue was distilled, yielding the eleven position amino acid C-protected by Boc.

A solution of the eleven position amino acid C-protected by Boc (2.28 g, 15 mmol) was reacted with 4.19 g (15.1 mmol) of N-protected ten position amino acid in 200 mL of $CH_2Cl_2$ and was cooled with stirring under inert atmosphere in an ice/water bath. The cold mixture was 'treated' with DIEA (5.75 mL, 32.3 mmol) followed by BOP-Cl (4.19 g, 16.5 mmol). The mixture was stirred for 2 hr in the cold and the concentrated in vacuo. The residue was partitioned between water and ethyl acetate and the organic layer was separated and washed with $KHSO_4$, $H_2O$, 1N $NaHCO_3$, 50% brine, and brine. After drying over $Na_2SO_4$ it was concentrated in vacuo to a yellow oil and purified by flash chromatography on 300 g of silica gel, eluting with 7.5% acetone/hexane to yield an N- and C-protected 10-11 dipeptide.

A solution of the N and C-protected 10-11 dipeptide (4.65 g, 10.4 mmol) in 40 mL of 2-propanol was flushed with $N_2$ and treated with 500 mg of 10% Pd on carbon. The mixture was placed under hydrogen atmosphere, stirred for 14 hr, then flushed with nitrogen, filtered through a pad of Celite, and concentrated in vacuo. The residue was then treated with 150 mL of 0.5N HCl, which was then washed with ether (2×) made basic with 5% ammonium hydroxide to pH=9, and again washed with ether (3×). These latter extracts were combined, washed with 50% brine and brine, and dried over $MgSO_4$. The compound was then concentrated in vacuo resulting in a C-protected 10-11 dipeptide.

A solution of the C-protected dipeptide (2.75 g, 8.75 mmol) and DIEA (3.2 mL, 18.4 mmol) in 120 mL of $CH_2Cl_2$ was cooled with stirring under inert atmosphere in an ice/water bath. The cold mixture was treated simultaneously with 2.57 g (9.2 mmol) of N-protected nine position amino acid and 2.34 g (9.2 mmol) of BOP-Cl. The mixture was stirred for 24 hr, slowly warming to 10° C. After washing with $H_2O$, 10% $KHSO_4$, 1N $NaHCO_3$, 50% brine, and brine, it was dried over $MgSO_4$ and concentrated in vacuo to a yellow oil. Purification on a column of 250 g silica gel and elution with 7.5% acetone/hexanes yielded a C- and N-protected 9-10-11 tripeptide.

Hydrogenation of the C- and N-protected 9-10-11 tripeptide was carried out as above for the C- and N-protected 10-11 dipeptide using 30 mL of 2-propanol and 300 mg of 10% Pd on Carbon. However, in this case treatment of the residue from the hydrogenation mixture with aqueous HCl resulted in the formation of the hydrochloride salt, which was treated with 5% $NH_4OH$, and the mixture was extracted with ether (3×). The organic layers were combined, washed with $H_2O$ and brine, dried over $MgSO_4$, and concentrated to yield the C-protected 9-10-11 tripeptide.

A solution of the C-protected 9-10-11 tripeptide (2.33 g, 5.44 mmol) and 1.99 mL (11.1 mmol) DIEA in 75 mL $CH_2Cl_2$ was cooled with stirring under inert atmosphere in an ice/water bath. The cold mixture was treated simultaneously, in one portion with the N-protected eight position amino acid (1.78 g, 5.72 mmol) and BOP-Cl (1.46 g, 5.74 mmol). The mixture was transferred to a 4–6° C. cold room and allowed to react for 17 hrs. The workup of the product was performed as discussed above for the C- and N-protected 9-10-11 tripeptide, and chromatography on 200 g of silica gel, eluting with 15% acetone/hexanes yielded the N- and C-protected 8-9-10-11 tetrapeptide fragment (SEQ ID NO:2).

General Procedure C:
Synthesis of CsA Hexapeptide Fragment 2-7 (SEQ ID NO:26)

A solution of the six position amino acid N-protected by a Boc group (10.31 g, 42.02 mmol) and DIEA (7.67 mL, 44.0 mmol) in 250 mL of $CH_2Cl_2$ was cooled in an ice/water bath under $N_2$ and treated with 11.21 g (44.02 mmol) of BOP-Cl, and the suspension was stirred vigorously for 2.5 hours. To this mixture was added, in one portion, a solution of the seven position amino acid C- protected by a OBzl group (7.298 g, 40.72 mmol) and DIEA (7.67 mL, 44.0 mmol) in 6 mL of $CH_2Cl_2$. The mixture was placed under a $CaSO_4$ drying tube and stirred overnight in a 5° C. cold room. The solution was then poured into ether (3× volume) and water (2× volume). The organic layer was separated, washed with 10% aqueous KHSO4, $H_2O$, 1N $NaHCO_3$, 50% brine, and brine. After drying over $MgSO_4$ it was concentrated in vacuo and purified by chromatography on 400 g of silica gel, eluting with 10% acetone/hexanes to yield an N- and C-protected 6-7 dipeptide.

Next, 8.946 g (22 mmol) of the N- and C-protected 6-7 dipeptide was deprotected with 50% TFA in methylene chloride to afford, after neutralization, extraction into methylene chloride, and evaporation, a quantitative yield of the C-protected 6-7 dipeptide.

Thereafter 1.9 g (6.2 mmol) of the C-protected 6-7 dipeptide and 2.21 g (8.68 mmol) of BOP-Cl were added to 30 mL of methylene chloride. The suspension was cooled to 0° C. under inert atmosphere and a mixture of N-protected five position amino acid (2.44 g, 8.68 mmol) and DIEA (3.0 mL, 17 mmol) in 30 mL of methylene chloride was added dropwise over 6 hr, to the rapidly stirred suspension. The reaction was stirred for an additional 14 hr at 5° C. and then concentrated to a thick oily residue, which was applied directly to 180 g of silica gel, and eluted with 20–30% EtOAc/hexanes to give an N- and C-protected 5-6-7 tripeptide.

Then 5.7 g (10 mmol) of the N- and C-protected 5-6-7 tripeptide was added to 1.52 mL (14 mmol) anisole and 7.8 mL of dioxane and cooled to 0° C. under inert atmosphere and treated with a precooled 0° C. solution of 5.8 M HCl-dioxane (17.2 mL, 100 mmol of HCl). After being stirred for 2 hr at 0° C. and an additional 12 hr at 5° C., the mixture was rotovaped under reduced pressure. After additional vacuum drying the C-protected 5-6-7 tripeptide was isolated and used directly for the next step.

The four position amino acid, N-protected by an Fmoc group, (4.41 g, 12 mmol) in 120 mL of methylene chloride was chilled to 0° C. under inert atmosphere. To this solution was added oxalyl chloride (2.3 mL, 26.4 mmol) in one portion followed, after several minutes by a catalytic amount of DMF (120 μL). After 2 hr the mixture was concentrated on a rotary evaporator as described in the previous paragraph and was used in the next coupling procedure.

A solution of the C-protected 5-6-7 tripeptide (10.0 mmol) in 30 mL of methylene chloride was cooled to 0° C. under inert atmosphere and treated with the entire yield of the Fmoc-four position amino acid (12.0 mmol) as a solution in 30 mL of methylene chloride. The stirred solution was treated dropwise over 1 hr with DIEA (4.2 mL, 24 mmol) in 30 mL of methylene chloride. After three hours at 0° C. the reaction was diluted with 90 mL methylene chloride and washed with 1M $KHSO_4$ and 50% brine. The organic layer was concentrated, diluted with diethyl ether/ethyl acetate mixture, and washed with saturated $NaHCO_3$, 50% brine, brine. After drying over $MgSO_4$ and concentrating in vacuo, the resulting C- and N-protected 4-5-6-7 tetrapeptide (SEQ ID NO:23) was chromatographed on 700 g silica gel.

A solution of the C- and N-protected 4-5-6-7 tetrapeptide (SEQ ID NO:23) (3.2 g 6 mmol) in 30 mL $CH_3CN$ was treated with an equal volume of DIEA while cooling on ice under inert atmosphere. After being stirred for 3 hr at 0° C., the solution was concentrated in vacuo, and the residue was treated with 20 mL of $CH_3CN$ and again concentrated. This was treated with 60 mL of methylene chloride and 2.31 mL (13.2 mmol) of DIEA and then chilled to 0° C. under inert atmosphere. The 2-3 dipeptide was added (1.81 g, 6.6 mmol) along with BOP-CL (1.83 g, 7.2 mmol) to the ice cold stirred solution. After 5 hr at 0° C. the reaction mixture was concentrated in vacuo and the residue was dissolved in diethyl ether/ethyl acetate mixture. The organic layer was separated, washed with 10% aqueous $KHSO_4$, $H_2O$, 1N $NaHCO_3$, 50% brine, and brine. After drying over $MgSO_4$ it was concentrated in vacuo and purified by chromatography on 400 g of silica gel, eluting with 30% acetone/hexanes to yield an N- and C-protected 2-3-4-5-6-7 hexapeptide (SEQ ID NO:26).

The N and C-protected 2-3-4-5-6-7 hexapeptide (SEQ ID NO:26) was N-deprotected by reaction of 868 mg (1.1 mmol) of the hexapeptide with 5.5 mL of TFA in 1.5 mL of methylene chloride for 14 hr at −15° C. to yield after workup, a C-protected 2-3-4-5-6-7 hexapeptide (SEQ ID NO:26).

General Procedure D:
Synthesis of CsA Heptapeptide Fragment 1-7

A suspension of MeBmt or MeLeu(3-OH)(0.2 mmol, 1 equiv) in freshly distilled acetone (60 mL) was heated to reflux under $N_2$ for 24 h until an almost clear solution appeared. The acetonide of MeBmt or MeLeu(3-OH) solution was concentrated in vacuo to 1.5 mL, which was directly used for the next coupling reaction without further purification.

To a solution of freshly prepared acetonide-protected amino acid (0.2 mmol, 1 equiv) in acetone (1.5 mL) was added 3 mL of THF, N-methylmorpholine (0.22 mmol, 1.1 equiv), 1-hydroxybenzotriazole (0.44 mmol, 2.2 equiv), and hexapeptide amine (0.22 mmol, 1.1 equiv). The resultant mixture was cooled to 0° C. and DCC (0.22 mmol, 1.1 equiv) was added. The mixture was allowed to warm up to room temperature and stirred under $N_2$ for 20 h, after which time the precipitated dicyclohexylurea (DCU) was removed by filtration and washed with small portion of $CH_2Cl_2$. The combined filtrate was washed with saturated $NaHCO_3$ solution and dried over $MgSO_4$. Concentration in vacuo and dissolution of the residue in EtOAc yielded more DCU. The residue remaining after a second filtration and concentration in vacuo was purified by chromatography with 10–40% acetone in freshly distilled n-hexane to give the N,O-Isopropylidene-protected heptapeptide 1-7 (SEQ ID NO:10).

A solution of N,O-isopropylidene heptapeptide (0.156 mmol) in 3 mL of MeOH was stirred with 1N HCl aqueous solution (0.6 mmol, 4 equiv) at room temperature for 15 hours. The reaction mixture was treated with $NaHCO_3$ (2 mmol) and concentrated in vacuo to a white solid. The residue was taken up in 2% MeOH in $CH_2Cl_2$ and flash-chromatographed with 2–4% MeOH in $CH_2Cl_2$ to give the 1-7 heptapeptide.

General Procedure E:
Synthesis of Linear Uncyclized CsA Analog

A solution of N-protected heptapeptide (residue 1-7) (SEQ ID NO:10) (0.1 mmol) and tetrapeptide amine (residue 8-11) (SEQ ID NO:2) (0.15 mmol, 1.5 equiv) in $CH_2Cl_2$ (2 mL) was treated sequentially with N-methylmorpholine (0.2 mmol) and BOP-Cl reagent. The reaction mixture was sealed tightly and stirred at room temperature under $N_2$ for 3 days. The mixture was then diluted with $CH_2Cl_2$ (15 mL) and water (10 mL). The aqueous layer was extracted with additional $CH_2Cl_2$ (3×10 mL) and the combined organic layers were dried over $MgSO_4$ and concentrated in vacuo. The resultant residue was purified by flash chromatography on silica gel with 10–40% acetone in freshly distilled n-hexane to give a pure, fully-protected undecapeptide (SEQ ID NO:27). Some impurities with higher $R_f$, possibly another undecapeptide epimer or unreacted substrates, were usually isolated during the chromatographic process.

General Procedure F:
Synthesis of Cyclized CsA Analog

A solution of the protected undecapeptide (0.05 mmol) in EtOH (2 mL) was flushed with $N_2$ and cooled to 0° C. The mixture was treated with 0.2N NaOH solution (0.5 mL) and stirred for 1.5 h; an additional portion of 0.2N NaOH solution (0.25 mL) was added and stirring was continued at 0° C. for 3.5–12 hours. The reaction mixture was then neutralized to pH 6 with 0.2N HCl solution (0.75 mL) and washed with brine (10 mL) and $CH_2Cl_2$ (20 mL). The aqueous layer was then extracted with additional $CH_2Cl_2$ (4×10 mL). The combined organic layers were dried over $MgSO_4$ and concentrated in vacuo to dryness to give a clear oil which was used directly for further reaction.

The oily residue (0.05 mmol) was dissolved in $CH_2Cl_2$ (200 mL) and treated sequentially with DMAP (0.25 mmol) and propyl phosphonic anhydride (a 50% w/v solution in $CH_2Cl_2$ from Fluka). The reaction mixture was stirred at room temperature under $N_2$ for 2 days, concentrated to 1–2 mL, and applied directly to a silica gel column. Flash chromatography with 10–40% acetone in freshly distilled n-hexane gave a pure cyclic undecapeptide compound.

EXAMPLE 3

Specific Experimental Synthetic Procedure for Preferred CsA Analog [Me(3-OH)Leu[(1)],MeAla[(4)], MeAla[(6)]]CsA Specific Experimental Procedure A:
Synthesis of β-Hydroxy-N methylleucine (MeLeu(3-OH))

Isobutyraldehyde (0.3 mL, 3.2 mmol) and isothiocyanate chiral auxiliary (1.3 g, 4.8 mmol) were condensed to give 0.6 g (54%) of (4S)-3-((4'S,5'R)-5'-isopropyl-2'-thioxo-4'-oxazolidinylcarbonyl)-4-(phenylmethyl)-2-oxazolidinone as a foamy solid.

The aldol adduct (550 mg, 1.58 mmol) was hydrolyzed to afford Methyl (4S,5R)-5-isopropyl-2-thioxo-oxazolidine-4-carboxylate (240 mg (75%)) as a clear oil.

The carboxylate (700 mg, 3.45 mmol) was treated with Meerwein reagent (trimethoxonium tetrafluoroborate) to give 246 mg (35%) of Methyl (4S,5R)-5-isopropyl-3-methyl-2-oxazolidinone-4-carboxylate as a clear oil. The (4R)-Epimer was obtained as a foamy solid (104 mg, 14%).

The methyl ester (150 mg, 0.75 mmol) was hydrolyzed with 0.2N KOH to give, after purification with Sephadex® LH-20, 90 mg (75%) of (2S,3R)-3-Hydroxy-N-methylleucine as a white solid.

Specific Experimental Procedure B:
Synthesis of CsA Tetrapeptide Fragment 8-11, (D)-Ala-MeLeu-MeLeu-MeVal (SEQ ID NO:2) [[(9-Fluorenylmethyl)oxy]carbonyl]-D-Alanyl-N-Methyl-L-leucyl-N-Methyl-L-leucyl-N-Methyl-L-Valine t-Butoxy Ester (Fmoc-D-Ala-MeLeu-MeLeu-MeVal-Boc) was synthesized according to the general procedure B (See, Example 2, above) in 85% yield and obtained as a foamy solid.

Specific Experimental Procedure C:
Synthesis of CsA Hexapeptide Fragment 2-7, Abu-Sar-MeAla-Val-MeAla-Ala (SEQ ID NO:26)

L-2-Aminobutyryl-Sarcosyl-N-Methyl-L-alanyl-L-Valyl-N-Methyl-L-alanyl-L-Alanine Benzyl Ester HLeu-Abu-Sar-MeAla-Val-MeAla-Ala-OBzl) was synthesized according to the general procedure C (See, Example 2, above) in 65% yield and obtained as a foamy solid.

Specific Experimental Procedure D:
Synthesis of CsA Heptapeptide Fragment 1-7, MeLeu(3-OH)-Abu-Sar-MeAla-Val-MeAla-Ala (SEQ ID NO:5)

(4S,5R)-2,2,3-Trimethyl-5-isopropyl-4-(oxazolidinyl)-carbonyl]-L-2-Aminobutyryl-Sarcosyl-N-Methyl-L-alanyl-L-Valyl-N-Methyl-L-alanyl-L-Alanine Benzyl Ester (N,O-Isopropylidene-Me(3-OH)Leu-Abu-Sar-MeAla-Val-MeAla-Ala-OBzl) was synthesized according to the general procedure D (See, Example 2, above) in 55% yield and obtained as a foamy solid.

(2S,3R)-3-Hydroxy-N-methyl-leucyl-L-2-Aminobutyryl-Sarcosyl-N-Methyl-Lalanyl-L-Valyl-N-Methyl-L-alanyl-L-Alanine Benzyl Ester (H-Me(3-OH)Leu-Abu-Sar-MeAla-Val-MeAla-Ala-OBzl) was synthesized according to the general procedure D in 62% yield and obtained as a foamy glass.

Specific Experimental Procedure E:
Synthesis of Linear Uncyclized CsA Analog (SEQ ID NO:6)

[[(9-Fluorenylmethyl)oxy]carbonyl]-D-Alanyl-N-Methyl-L-leucyl-N-Methyl-L-leucyl-N-Methyl-L-Valyl-[(2S,3R)-3-hydroxy-N-methyl-leucyl]-L-2-Aminobutyryl-Sarcosyl-N-Methyl-L-alanyl-L-Valyl-N-Methyl-L-alanyl-L-Alanine Benzyl Ester (Fmoc-D-Ala-MeLeu-MeLeu-MeVal-Me(3-OH)Leu-Abu-Sar-MeAla-Val-MeAla-Ala-OBzl) was synthesized according to the general procedure E (See, Example 2, above) in 34% yield and obtained as a foamy solid.

EXAMPLE 4

Immunostimulatory Properties of CsA Analogs

The novel immunostimulatory properties of the present claimed CsA analogs were determined by the following procedure:

First, PBMC's from a healthy donor were isolated by density centrifugation over histopaque (Sigma). The PBMC's were activated with PHA at 1 µg/mL and plated at $1 \times 10^5$ cells/well in the presence of both serially diluted CsA or a CsA analog. The cells were incubated for 3 days before being pulsed with $^3$H-thymidine and harvested the next day. The amount of radioactivity was determined by scintillation counting. The results are shown in Table 5.

TABLE 5

Immunostimulatory Data

| Compound | Concentration (µg/mL) | Counts Per Minute + Std Dev |
| --- | --- | --- |
| CsA | 10 | 1806 ± 834 |
|  | 1 | 2815 ± 774 |
|  | 0.1 | 3171 ± 332 |
|  | 0.01 | 13339 ± 3283 |
|  | 0.001 | 15248 ± 3898 |
| [L—MeLeu (3-OH)$^1$, MeAla$^{4,6}$]—CsA | 10 | 69959 ± 5978 |
|  | 1 | 42779 ± 3396 |
|  | 0.1 | 26646 ± 4236 |
|  | 0.01 | 23615 ± 6484 |
|  | 0.001 | 25773 ± 9147 |
| Media Control |  | 40222 ± 7183 |
| Diluent Control |  | 32279 ± 9205 |
| Unstimulated |  | 1032 ± 453 |

The study was then wxpanded to examine the immunostimulatory properties of the CsA analogs of the present invention by performing the aforementioned procedure on PBMC's obtained from eight additional human donors. The results illustrate a small degree of immunostimulatory variability between individuals, but the tangible nature of the immunostimulatory effect remains constant. The data are shown in Table 6.

TABLE 6

Immunostimulatory Data

| Subject | Concentration (µg/mL) | Counts Per Minute + Std Dev |
| --- | --- | --- |
| Donor 1 | 20 | 75500 ± 3425 |
|  | 10 | 69000 ± 1230 |
|  | 5 | 53300 ± 8723 |
|  | 2.5 | 60800 ± 3170 |
|  | 1.25 | 58200 ± 1881 |
|  | Media Control | 51230 ± 4176 |
|  | Diluent Control | 74000 ± 982 |
| Donor 2 | 20 | 62910 ± 9833 |
|  | 10 | 36420 ± 6615 |
|  | 5 | 30400 ± 7417 |
|  | 2.5 | 25150 ± 902 |
|  | 1.25 | 27300 ± 6925 |
|  | Media Control | 24550 ± 15196 |
|  | Diluent Control | 33287 ± 2610 |
| Donor 3 | 20 | 61500 ± 7037 |
|  | 10 | 47670 ± 10127 |
|  | 5 | 56172 ± 4973 |
|  | 2.5 | 50300 ± 9449 |
|  | 1.25 | 50510 ± 3276 |
|  | Media Control | 49051 ± 13000 |
|  | Diluent Control | 63042 ± 9720 |
| Donor 4 | 20 | 39062 ± 5324 |
|  | 10 | 35200 ± 2543 |
|  | 5 | 43060 ± 7950 |
|  | 2.5 | 36507 ± 16397 |
|  | 1.25 | 33800 ± 716 |
|  | Media Control | 23340 ± 7127 |
|  | Diluent Control | 38200 ± 6969 |

TABLE 6-continued

Immunostimulatory Data

| Subject | Concentration (μg/mL) | Counts Per Minute + Std Dev |
|---|---|---|
| Donor 5 | 20 | 32000 ± 5324 |
| | 10 | 16700 ± 881 |
| | 5 | 24500 ± 4180 |
| | 2.5 | 16400 ± 1720 |
| | 1.25 | 13600 ± 994 |
| | Media Control | 13528 ± 3727 |
| | Diluent Control | 10642 ± 1820 |
| Donor 6 | 20 | 47160 ± 11635 |
| | 10 | 44900 ± 6950 |
| | 5 | 41523 ± 10595 |
| | 2.5 | 40784 ± 1059 |
| | 1.25 | 35870 ± 9692 |
| | Media Control | 38000 ± 13433 |
| | Diluent Control | 37000 ± 8921 |
| Donor 7 | 20 | 37100 ± 15202 |
| | 10 | 34550 ± 329 |
| | 5 | 24550 ± 3045 |
| | 2.5 | 22130 ± 982 |
| | 1.25 | 46162 ± 386 |
| | Media Control | 15500 ± 3830 |
| | Diluent Control | 28050 ± 2706 |
| Donor 8 | 20 | 62713 ± 2247 |
| | 10 | 45500 ± 10570 |
| | 5 | 46670 ± 728 |
| | 2.5 | 61846 ± 21866 |
| | 1.25 | 46162 ± 386 |
| | Media Control | 40168 ± 7319 |
| | Diluent Control | 46130 ± 10145 |

EXAMPLE 5

Solid Phase Synthesis of CsA Analogs

The structure-activity relationships for other biological activities of CsA outside of immunosuppression are not definitively known. The current literature shows that only a small fraction of the possible CsA derivatives have been synthesized to date. In addition, since some CsA substitutions act synergistically, one cannot predict the activities of multiply-substituted CsA derivatives from the existing database which is made up mostly of single amino-acid substitutions. The only logical procedure for deducing the structure-function relationship for CsA derivatives is to synthesize large numbers of derivatives and subsequently screen them for biological activity. This procedure requires a new method of synthesizing CsA derivatives, in particular by solid-phase techniques.

During the course of synthesizing the novel CsA analogs, methods were discovered of synthesizing precursors of the CsA analogs by solid phase methods. Although efficient methods for the total synthesis of CsA and analogs in solution have been available for several years, the synthesis of CsA by solid phase synthetic methods has not yet been achieved, in part because conventional coupling procedures with sterically hindered or N-methyl amino acids often result in incomplete couplings under solid phase synthesis conditions, leading to deletion sequences.

Figure 14:
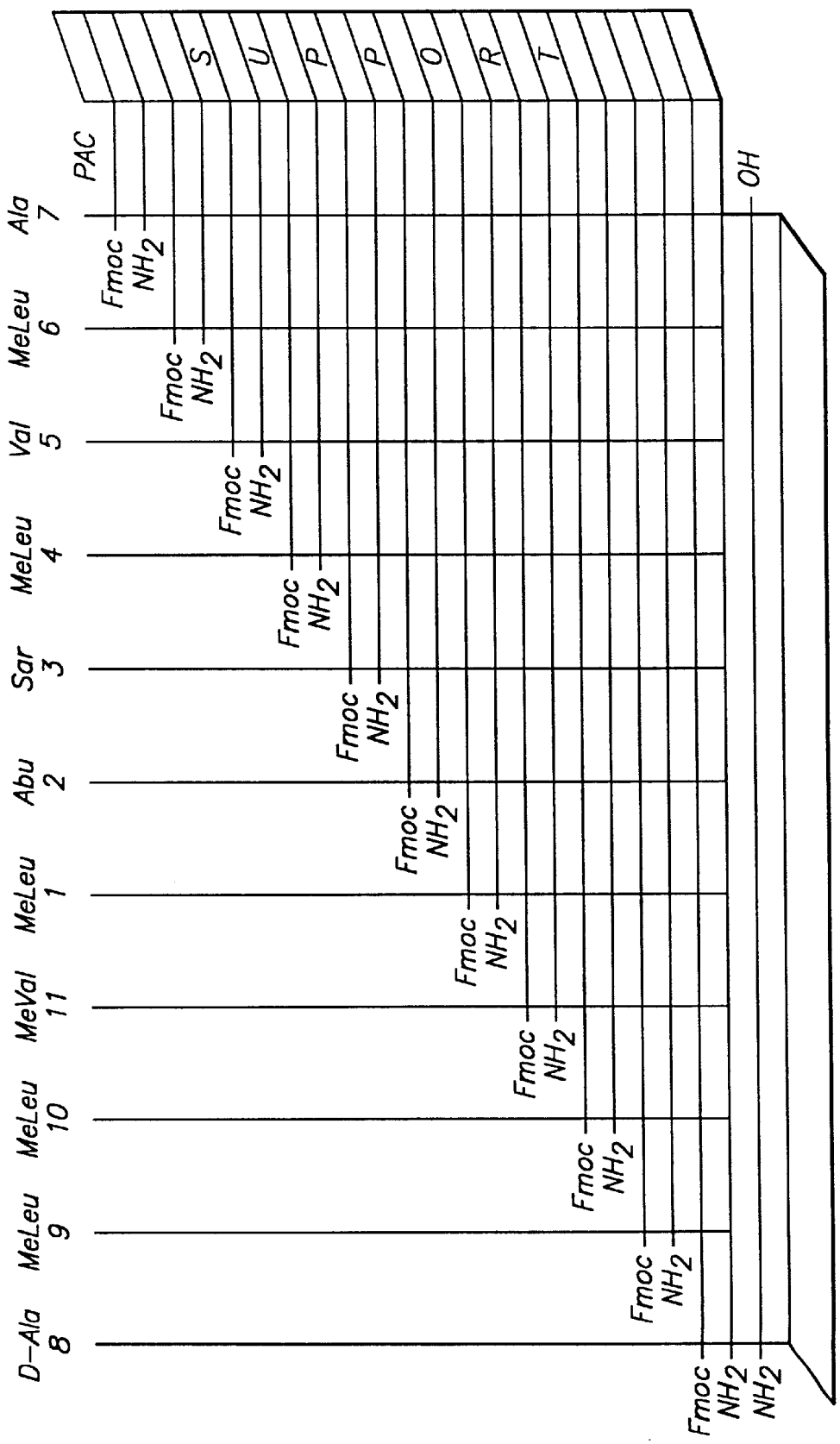
FIG. 14 depicts a solid phase synthesis method for generating (MeLeu$^1$)CsA (SEQ ID NOS:12–20).

Subsequently, an entire cyclic CsA derivative was synthesized using the following solid-phase synthetic procedure, which is outlined in FIG. 14 (SEQ ID NOS:12–20):

1) The cyclosporin analog was synthesized utilizing a PAC (p-alkoxybenzyl alcohol) group to link the growing peptide chain to the MBHA (methylbenzhydrylamine) polystyrene resin.
2) DMF (N,N-dimethylformamide) was used to swell and wash the resin.
3) The first amino acid linked to the support was an Fmoc-amino-protected amino acid in three fold excess which was linked to the resin by reaction with DIPCDI (diisopropylcarbodiimide) in three-fold excess over 90 minutes.
4) The Fmoc group was removed from the first amino acid by reaction with piperidine/DMF (v:v 3:7).
5) The second amino acid linked to the peptide was an Fmoc-amino-protected amino acid in three fold excess which was linked to the resin by reaction with BOP/DIEA in three fold excess over 3 hours.
6) The Fmoc group was removed from the terminal amino acid by reaction with piperidine/DMF (v:v 3:7) in three fold excess.
7) The third amino acid linked to the peptide was an Fmoc-amino-protected amino acid in three-fold excess which was linked to the resin by reaction with HATU [O-(7-azabenzotriazol-1-yl)-1,1,2,2,-tetramethyluronium hexafluorophosphate]/DIEA in three-fold excess using a double-coupling protocol of two (3hr) couplings.
8) The Fmoc group was removed from the terminal amino acid by reaction with piperidine/DMF (v:v 3:7).
9) Steps 7 and 8 were sequentially repeated until the peptide was eleven amino acids long.
10) The deprotected undecapeptide was cleaved from the resin using TFA $H_2O$ (v:v 95:5) for 4 hours, washed with ether, dried, and purified by reverse-phase high performance liquid chromatography.
11) The undecapeptide was cyclized by reaction with $(PrPO_2)_3$ and DMAP in $CH_2Cl_2$ solution under highly dilute conditions.
12) The cyclized peptide was obtained in 10–15% yield and purified by column chromatography and characterized by NMR and FABMS.

Figure 15:
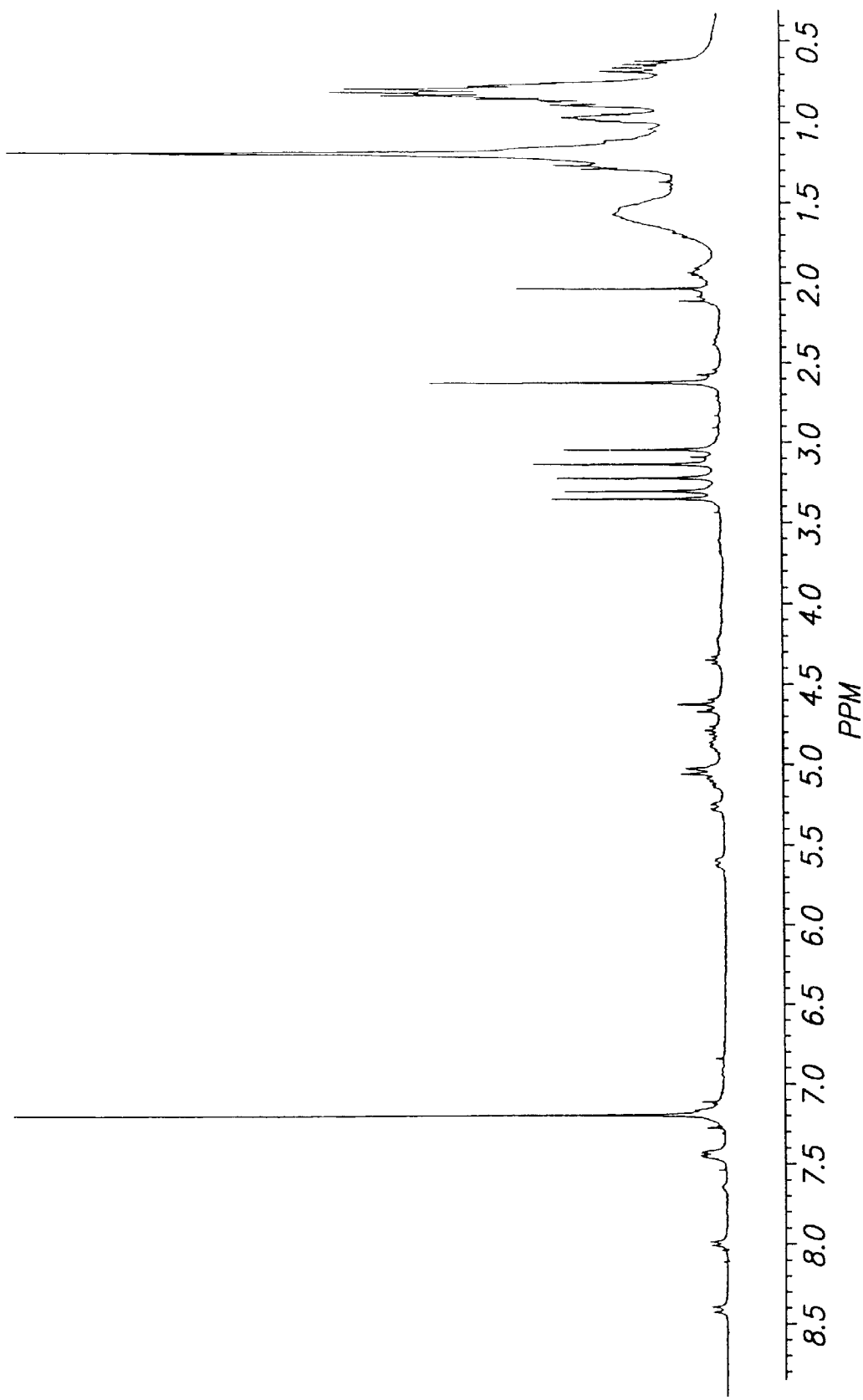
FIG. 15 depicts the NMR spectrum of (MeLeu$^1$)CsA synthesized by solid phase methods.
Figure 16:
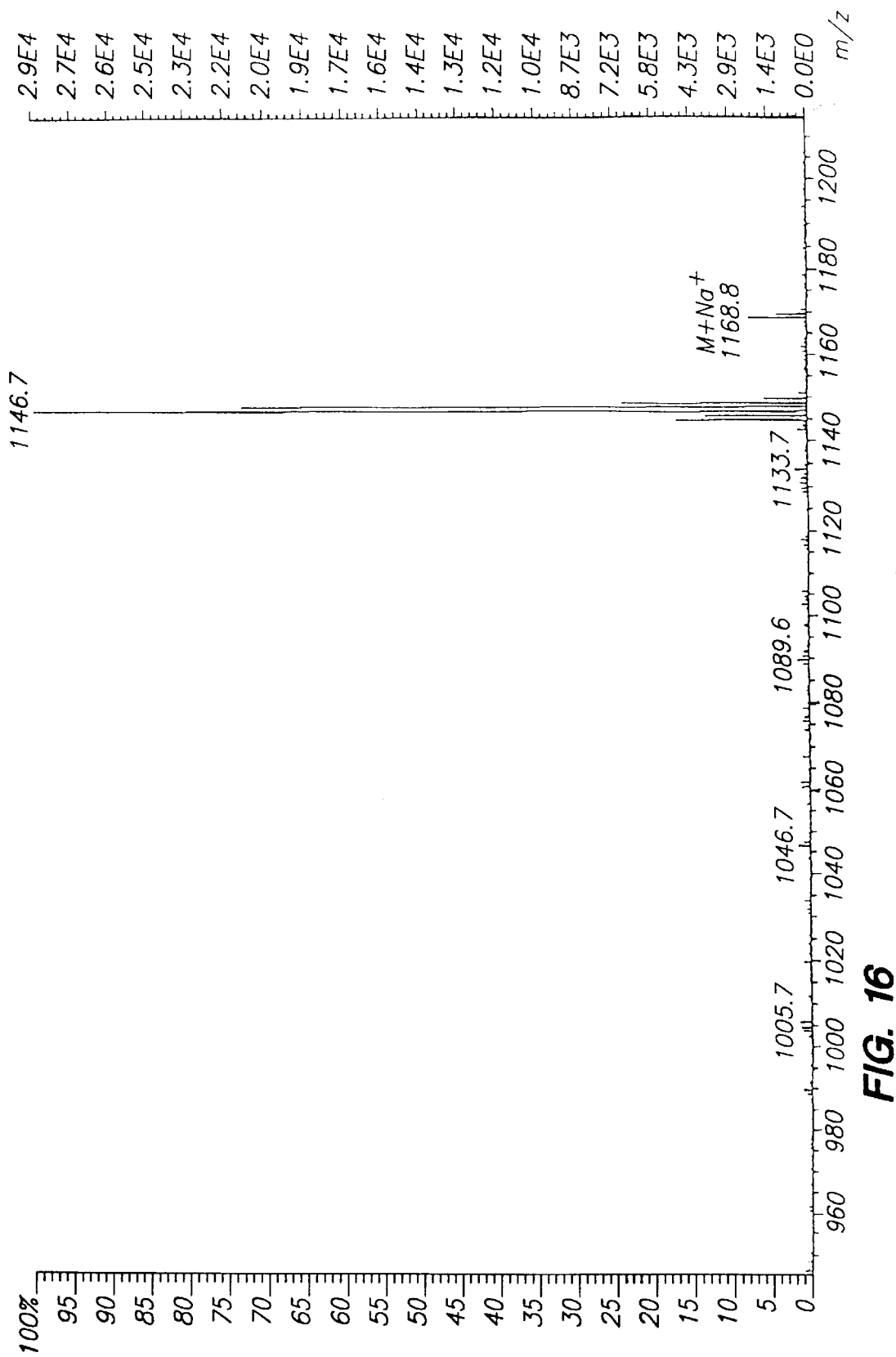
FIG. 16 depicts the FABMS spectrum of (MeLeu$^1$)CsA synthesized by solid phase methods.
Figure 17:
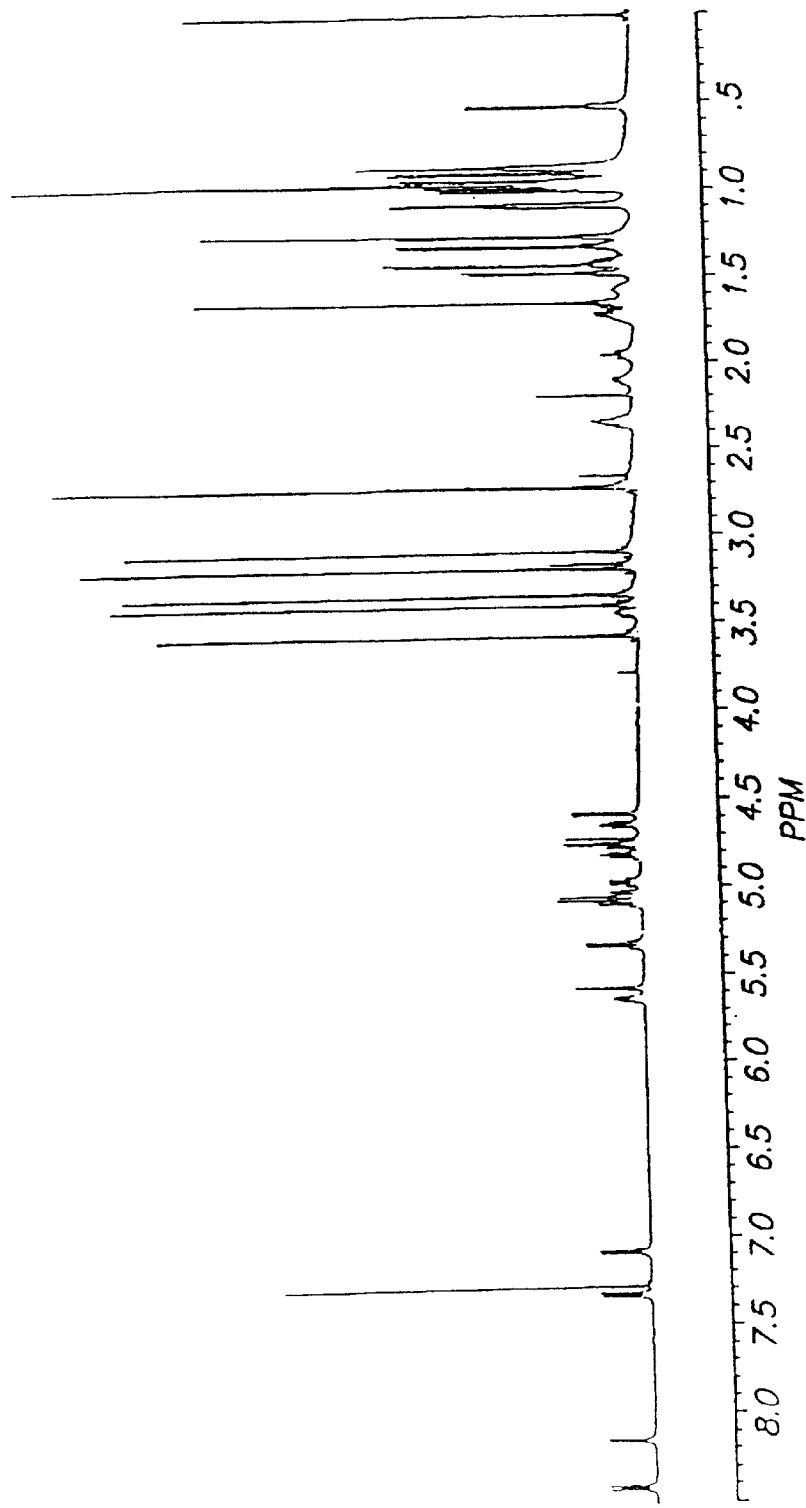
FIG. 17 depicts the NMR spectrum of the preferred CsA analog, (MeLeu[3-OH]$^1$,MeAla$^{4,6}$)CsA.

Using this procedure the CsA analog [MeLeu$^1$]-CsA was synthesized. The NMR and FABMS spectra are attached at FIGS. 15 and 16 respectively. Using the solid-phase techniques discussed here it is possible to create libraries of CsA analogs using combinatorial methods discussed in the literature. (See Gallop, M. A. et al., J. Med. Chem. 37:1233 (1994); and Gordon, E. M. et al., J. Med. Chem. 37:1385 (1994)).

EXAMPLE 6

Screening CsA Derivatives For Biological Activity

As previously noted, the preferred CsA derivative is both non-immunosuppressive as well as anti-HIV. The following section outlines a procedure whereby a novel CsA derivative can be screened for potentially useful biological activity.

The Screening Modes consist of the following biological assays:

Mode I: Determine whether the CsA analog of interest inhibits calcineurin and is therefore immunosuppressive.
Mode II: Determine whether the non-immunosuppressive CsA analog of interest inhibits cyclophilin as well as cyclophilin-mediated HIV replication.
Mode III: Determine whether the CsA analog of interest inhibits Heat Shock Protein (hsp70) and evaluate such inhibitors for effects on viral assembly.
Mode IV: Determine whether the CsA analog of interest inhibits HIV protease as well as other proteases.

A new CsA analog ("X") can be evaluated for biological activity using the procedure outlined in Table 7.

TABLE 7

Evaluation of Biological Activities of Novel CsA Analogs

| Mode | Result | Interpretation/Next Step |
| --- | --- | --- |
| I | +inhib | Compound is immunosuppressive. |
| I | −inhib | Compound is not immunosuppressive/Evaluate in Modes II, III, and IV. |
| II | +inhib | Compound is a cyclophilin inhibitor and may also inhibit HIV replication/Evaluate directly for HIV inhibition as well as in Modes III and IV for additional utility. |
| II | −inhib | Compound is not a cyclophilin inhibitor and will not inhibit HIV replication/Evaluate in Modes III and IV for additional utility. |
| III | +inhib | Compound is an hsp70 inhibitor and may also inhibit other viral infections such as rabies and hepatitis B/Evaluate directly for viral inhibition as well as in Mode IV for additional utility. |
| III | −inhib | Compound is not an hsp inhibitor and will not inhibit rabies and hepatitis B infections/Evaluate in Mode IV for additional utility. |
| IV | +inhib | Compound is a protease inhibitor (HIVP inhibitor). |
| IV | −inhib | Compound is not a protease inhibitor (HIVP inhibitor). |

Key:
+inhib = process inhibited;
−inhib = process not inhibited.

Several binding assays are required for assessing the potential of cyclosporin analogs for cyclophilin binding, potential immunosuppression, and possible HIV-protease inhibition of hsp70 binding. Sensitive and robust assays are necessary to process the large numbers of CsA analogs created by the solid-phase synthesis described in Example 5. The binding assays described below are used for the screening of the CsA analog libraries. The assays are adapted from the technology developed for ELISA systems and histochemistry over the past twenty years. Such systems are inherently heterogeneous and therefore ideally suited for screening analogs bound to beads. The best candidates from the initial screening are further tested by using more specific assays to probe biological effects. For example, those compounds found not to be immunosuppressive in Mode I can be tested as potential immunostimulatory analogs of CsA in mitogen assays as described in Example 5 above. The screening of the analogs can be accomplished either with the analog attached to the bead on which it was synthesized or in solution, depending on the requirements of the assay.

Sources of Proteins Used in Assays

Cyclophilin (CyP) has been expressed and purified by one of the present inventors to a level of 80 mg purified cyclophilin per liter of culture. HIV protease was obtained in an available recombinant form. Hsp70 was obtained in a pET expression system (the pET expression system is commercially available from Novagen) and was purified. Both the commercially available bovine calcineurin and the human calcineurin subunit A may be used in these studies.

Cyclophilin-Cyclosporin Binary Complex Assays

One method of determining the level of binding between the CsA analog and cyclophilin involves coupling of fluoroscein isothiocyanate to purified cyclophilin using standard conditions. The fluorescent cyclophilin is bound to the cyclosporin linked to the solid phase synthesis beads enabling excess cyclophilin to be removed by a series of washes and the fluorescence detected with a fluorescent plate reader or microscope. The second assay is based on the ELISA method. The assay begins with biotinylating cyclophilin to form the [Biot-CyP] derivative. The binding of resin-CsA to [Biot-CyP] is detected by using alkaline phosphatase and peroxidase coupled to streptavidin which allows the cyclophilin-CsA complex to be measured quantitatively. A variation of this method uses an antibody to cyclophilin to bind the resin-bound cyclosporin analog. The antibody is detected by IgG antibody conjugated with alkaline phosphatase or peroxidase.

The binding of the CsA analogs can be modulated by titrating the complexes with CsA. Increasing CsA concentrations will displace weaker binding CsA analogs. Soluble CsA analogs that bind less tightly to CyP are used to compete off the less active resin-bound CsA derivatives. By controlling the concentration and potency of CsA competitors, it is possible to determine the best inhibitors in each synthetic preparation.

Cyclophilin-Cyclosporin-Calcineurin Ternary Complex Assays

One method of determining the degree of formation of cyclophilin-CsA-calcineurin binding is based on the fact that calcineurin binds only to the cyclophilin-CsA complex. Thus, addition of calcineurin and cyclophilin to the combinatorial library forms a ternary complex only with CsA analogs that bind to both proteins, a property usually associated with immunosuppressive CsA analogs. Ternary complexes are separated from the excess reagents and quantitated by either fluoroscein-labelled calcineurin or by an antibody to calcineurin.

The second assay is based on Amersham's Scintillation Proximity Assay system. In this assay, scintillant is covalently linked to a solid phase bead. The radioisotope must be adjacent to the bead in order for light production to take place. Using the biotinylated cyclophilin and streptavidin-SPA beads, the addition of the CsA analog in solution along with $I^{125}$-calcineurin causes scintillation. This method has been shown to be as sensitive as radioimmunoassays. This method can be limited to soluble CsA analogs due to the steric interactions of binding to solid phase beads, but does not require the separation of excess reagents.

HIV Protease and Hsp70 CsA Binary Complexes

The systems described earlier are also used to determine the level of binding to HIV-protease and hsp70 of the CsA analog using the appropriate antibodies, fluoroscein-labelled protein, or biotinylated HIV-protease or biotinylated hsp70 as necessary in place of cyclophilin.

EXAMPLE 7

General Method for the Solid Phase Synthesis and On-Resin Cyclization of CsA Analogs The experiments of this example illustrate the general procedure for the complete synthesis of a CsA analog using the solid-phase methods contemplated by the present invention. Although this example is directed at the generation of [MeLeu$^1$, Asp$^7$]CsA (SEQ ID NO:28), the general procedure outlined below is applicable, with appropriate modification, to the production of other analogs of CsA as well as other compounds.

Resin Linkage

Initially, the procedure requires linking to the resin via a suitably functionalized amino acid side-chain. Because Ala$^7$ can be replaced by other amino acids (e.g., aspartic acid) without eliminating either binding to cyclophilin or immunosuppressive activity (M.-K Hu et al., J. Med. Chem., 38:4164 [1995]), Ala$^7$ was replaced by Fmoc/O-allyl-protected aspartic acid to provide a point for attachment of the CsA derivative to the resin (See e.g., S. A. Kates et al., Tetrahedron Lett., 34:1549 [1993]; S. A. Kates et al., Anal. Biochem., 212:303 [1993]).

Fmoc-Asp-OAllyl was attached via the side-chain to Linker H-Peg-PS resin (PerSeptive Biosystems) (See, R. C. Sheppard et al., Int. J. Peptide Protein Res. 29:451 [1982]) using DIPCDI/DMAP for symmetrical anhydride esterification.

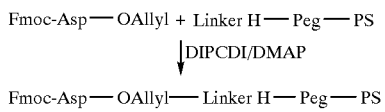

Sequential Deprotection And Coupling

After removal of the Fmoc protecting group with 2% DBU in DMF, the peptide was extended in the C-to-N direction using Fmoc-protected amino acids, using Millipore 9050 Plus synthesizer. Four-fold excess DIPCDI/HOAt in DMF was used for all couplings prior to Fmoc-MeVal[11].

Cyclization And Cleavage

Cyclization of the linear precursor to [MeLeu[1], Asp[7]]CsA (SEQ ID NO:28) was initially attempted using the standard protocol for cyclization of CsA analogs in solution, i.e., propyl phosphonic anhydride [$(PrPO_2)_3$, 1.5 eq]/DMAP (5 eq) for 72 hours. (See, R. M. Wenger, Helv. Chim. Acta 67:502 [1984]; and W. J. Colucci et al., J. Org. Chem. 55:2895 [1990]). As that protocol did not prove successful for on-resin cyclization of [MeLeu[1], Asp[7]]CsA (SEQ ID NO:28), the present inventors developed new methods for the on-resin cyclization reaction. Specifically, cyclization of the linear precursor to [MeLeu[1], Asp[7]]CsA (SEQ ID NO:28) was achieved by first removing the allylester with $Pd(PPh_3)_4$ (3 eq) in $CHCl_3$:AcOH:NMM (99.25:0.5:0.25), followed by Fmoc cleavage with DBU:piperidine:DMF(1:1:48). Several washes, encompassing separate solutions of 0.5% DIEA in $CH_2Cl_2$ and 0.5% sodium diethyldithiocarbamate in DMF,

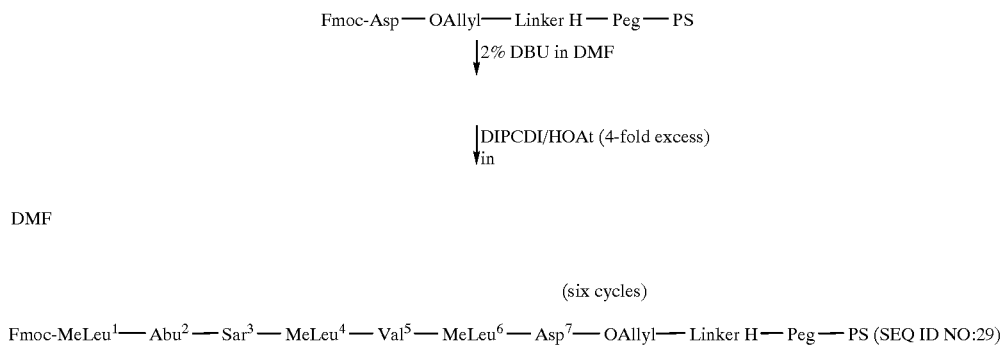

For the addition of amino acids in sequence 8-11, following removal of the Fmoc protecting group with 2% DBU in DMF, the peptide was extended using N-methyl pyrrolidinone (NMP) in excess as the solvent for all couplings. The use of NMP afforded more consistent results for the addition of those amino acids.

were used to eliminate the $Pd(PPh_3)_4$. On-resin cyclization was effected with BOP (5 eq)/HOBt (5 eq)/DIEA (10 eq) in DMF for 72 hours, as indicated by a negative Kaiser test. The analog was cleaved from the resin with TFA/$H_2O$/$CH_2Cl_2$ (10:89:1) at −20° C. for approximately 4 hours.

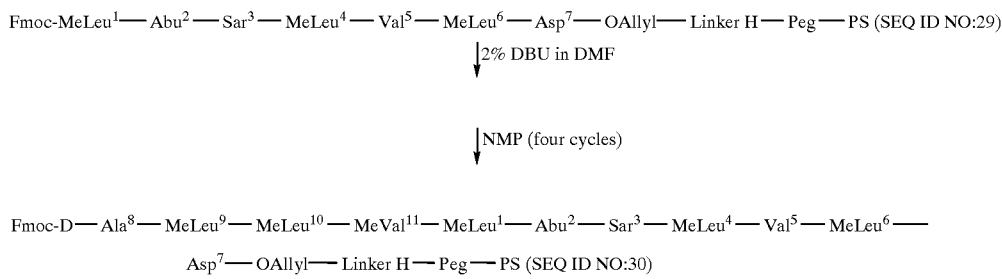

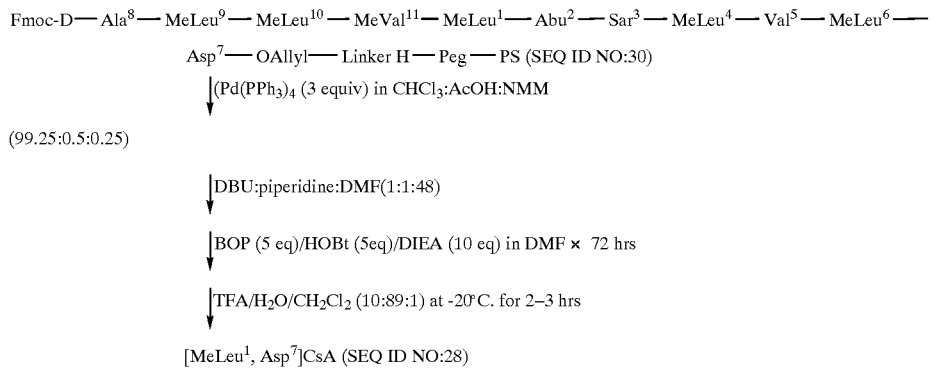

Figure 20:
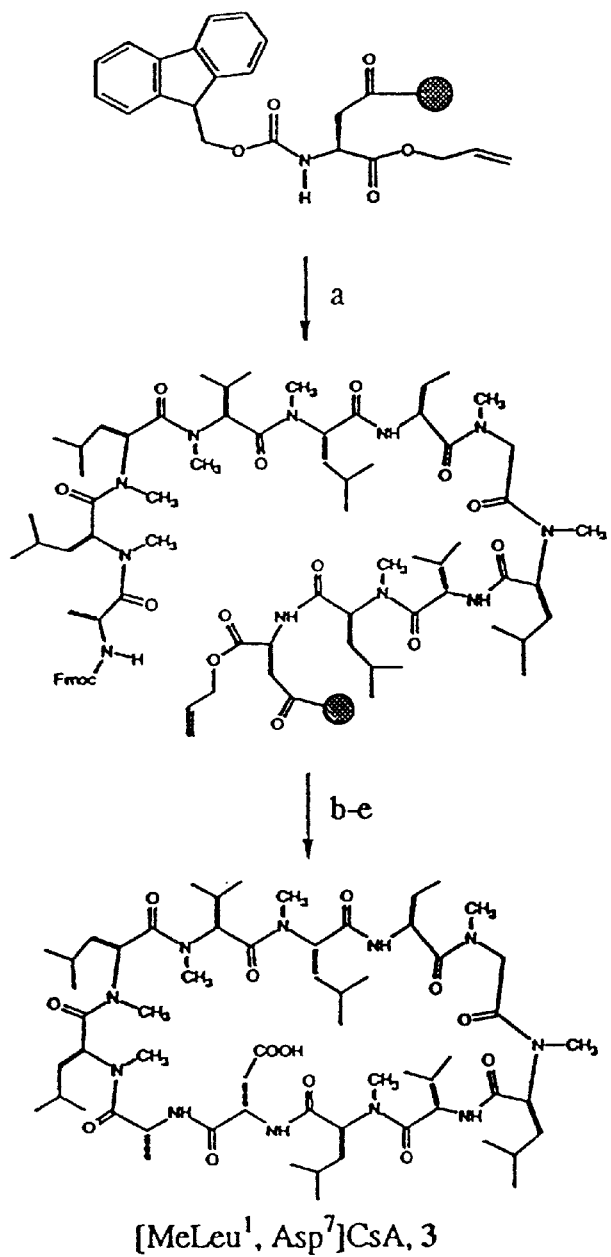
FIG. 20 diagrammatically depicts the complete solid phase synthesis of (MeLeu$^1$, Asp$^7$)CsA (SEQ ID NO:28).

The analog was obtained in an overall yield of 35–39%. FIG. 20 diagrammatically depicts the complete solid phase synthesis of [MeLeu¹, Asp⁷]CsA (SEQ ID NO:28).

Confirmation

The structure of [MeLeu¹, Asp⁷]CsA (SEQ ID NO:28) was established by LSIMS mass spectrometry of the acid, followed by NMR after conversion to the benzyl ester, [MeLeu¹, Asp(OBn)⁷]CsA (SEQ ID NO:3 1; see FIG. 19)(i.e., MeLeu¹-Abu²-Sar³-MeLeu⁴-Val⁵-MeLeu⁶-Asp(OBn)⁷-D-Ala⁸-MeLeu⁹-MeLeu¹⁰-MeVal¹¹, wherein "MeLeu" is methylleucine, and "Asp(OBn)" is aspartic acid benzyl ester), Because cyclosporins are known to adopt multiple conformations in the presence of DMSO, methanol, and water, and the free carboxylic acid group of Asp⁷ also leads to formation of multiple peptide ring system conformations, the 7-position aspartic acid carboxyl group was derivatized to simplify the NMR spectrum in CDCl₃.

For comparison purposes, the present inventors independently synthesized the same analog, [MeLeu¹, Asp(OBn)⁷] CsA (SEQ ID NO:31), via a method entailing cyclization in solution. More specifically, the analog was synthesized by linking Fmoc-Asp(OBn)-OH to PAC-PEG-PS (the structure of PAC is depicted in FIG. 18) (See e.g., R. C. Sheppard et al., Int. J. Peptide Res., 20:451 [1982]), assembling the linear undecapeptide, cleaving the linear undecapeptide from the resin, and cyclizing in solution. The sample obtained using this procedure was identical (via NMR) to that generated from on-resin cyclization.

EXAMPLE 8

Solid Phase Synthesis Of [MeSer¹]CsA (SEQ ID NO:32) and [MeThr¹]CsA (SEQ ID NO:33)

As previously indicated, the methods of the present invention may be utilized in the generation of, among other cyclic compounds, CsA analogs containing amino acid substitutions. In this example, the solid phase synthesis procedures of the present invention were used to generate CsA analogs with the oxygen functionality in the β-position that is found in MeBmt. More specifically, the methods were utilized to generate [MeSer¹]CsA (SEQ ID NO:32)(i.e., MeSer¹-Abu²-Sar³-MeLeu⁴-Val⁵-MeLeu⁶Ala⁷-D-Ala⁸-MeLeu⁹-Meleu¹⁰-MeVal¹¹, wherein "MeSer" is methylserine), and [MeThr¹] CsA (SEQ ID NO:33)(ie., -MeThr¹-Abu²-Sar³-MeLeu⁴-Val⁵-MeLeu⁶-Ala⁷-D-Ala⁸-MeLeu⁹-MeLue¹⁰-MeVal¹¹; wherein "MeThr" is methylthreonine), which serve as models for the synthesis of CsA analogs with the oxygen functionality in the β-position.

Resin Linkage

To avoid degradation of the N-alkylated peptides during resin cleavage by high concentrations of TFA, the mild acid labile linkers, Linker H and HAL, and the photolabile linker were used (See, FIG. 18). The labile linker and Linker H are commercially available (e.g., Calbiochem-Novabiochem). Linker H and HAL were synthesized for this experiment. The linkers were attached to PEG-PS resin (PerSeptive Biosystems). All of these linkers were used in different experiments, with the same general protocol; the only differences were related to the conditions required for cleavage from the resin.

Sequential Deprotection And Coupling

Fmoc-Ala⁷-OH was then attached via the carboxy terminus to the linkers and the CsA 2-7 hexapeptide was synthesized on PEG-PS resin (S. Zalipsky et al., in C. M Deber et al., (eds.) Peptides, Structure and Function Pierce Chemical Co.; Rockford, Ill., pp. 257–260 [1985]). A Millipore® 9050 Plus Synthesizer was used, and the deprotection and coupling protocols described in the preceding example were utilized. Coupling of Fmoc-MeSer¹(OBn)-OH and Fmoc-MeThr¹(OBn)-OH with the hexapeptide proceeded in nearly quantitative yield.

As was the situation with the synthesis of [MeLeu¹Asp⁷] CsA (SEQ ID NO:28) (see Example 8), the coupling of Fmoc-MeVal¹¹-OH onto the β-substituted 1-position residue of the heptapeptide led to less quantitative yields. Specifically, the double coupling protocol with DIPCDI/HOAt/DMF gave 70% coupling yield for the MeSer¹(OBn)-heptapeptide resin and 50% for the MeThr¹(OBn)-heptapeptide resin. These same yields were obtained whether manual batch synthesis or automated continuous-flow synthesis were used.

As previously indicated, difficult couplings on a solid support are sequence-dependent and have been attributed to interchain interactions and/or poor solvation that lead to limited accessibility to the amino group of the growing peptide chains. Different reaction conditions were evaluated regarding Fmoc-MeVal¹¹-OH coupling onto the MeSer¹ (OBn)-heptapeptide resin and MeThr¹(OBn)-heptapeptide resin to determine if some combination of reaction conditions would give nearly quantitative yields for this step. Different combinations of the solvents DMSO, THF, toluene and NMP did not improve the yield of the coupling. However, the coupling of Fmoc-MeVa¹¹-OH to the MeSer¹ (OBn)-heptapeptide resin went in quantitative yield when the solvent was switched to NMP and the temperature was raised to 60° C. By comparison, when the same conditions were applied to the coupling of Fmoc-MeVa$^{11}$-OH with the MeThr$^1$(OBn)-heptapeptide resin, the yield increased to 70%, but never reached completion despite increasing the coupling time. Finally, use of hydrogen bonding solvents such as TFE and HFIP in combination with NMP had little or no effect on the coupling yields (data not shown).

While use of the chaotropic agent KSCN did not improve the yield, use of that agent did enable complete capping of unreacted amine with N-acetyl imidazole, thus avoiding the formation of the decapeptide deletion peptide (i.e., the peptide lacking the MeVal$^{11}$ residue). Under the preferred conditions set forth above, the linear undecapeptide precursors for [MeSer(OBn)$^1$]CsA (SEQ ID NO:34)(ie., MeSer(OBn)$^1$-Abu$^2$-Sar$^3$-MeLeu$^4$-Val$^5$-MeLeu$^6$-Ala$^7$-D-Ala$^8$-MeLeu$^9$-MeLue$^{10}$-MeVal$^{11}$, wherein "MeSer" is methylserine benzyl ester) and [MeThr(OBn)$^1$]CsA (SEQ ID NO:35) (i.e., MeThr(OBn)$^1$-Abu$^2$-Sar$^3$-MeLeu$^4$-Val$^5$-MeLeu$^6$-Ala$^7$-D-Ala$^8$-MeLeu$^9$-MeLeu$^{10}$-MeVal$^{11}$, wherein "MeThr(OBn)" is methylthreonine benzyl ester) were synthesized smoothly using NMP at 60° C. for the coupling of the last four amino acid residues beginning with MeVal$^{11}$.

The undecapeptide precursors were Fmoc-deprotected (2% DBU in NMP), cleaved from the resin and cyclized in solution (PrPO$_2$)$_3$, DMAP, CH$_2$Cl$_2$) in an analogous manner to the [MeLeu$^1$]CsA (SEQ ID NO:36)(i.e., MeLeu$^1$-Abu$^2$-Sar$^3$-MeLeu$^4$-Val$^5$-MeLeu$^6$-Ala7-D-Ala$^8$-Meleu$^9$-MeLeu$^{10}$-MeVal$^{11}$, wherein "MeLeu" is methylleucine) undecapeptide precursor (described above). This led to the successful synthesis of [MeSer(OBn)$^1$]CsA (SEQ ID NO:34) and [MeThr(OBn)$^1$]CsA (SEQ ID NO:35) in excellent overall yields (5–16%). Cleavage of the benzyl ethers using Pearlman's catalyst (Aldrich) (Pd(OH)$_2$/C) proceeded smoothly to afford the target analogs [MeSer$^1$]CsA (SEQ ID NO:32) and [MeThr$^1$]CsA (SEQ ID NO:33), which were characterized by $^1$H NMR, LSIMS Mass Spectrometry, RP-HPLC, and TLC.

The mass spectral and TLC data for the synthesized analogs were as follows: [MeLeu$^1$,Asp$^7$]J-CsA (SEQ ID NO:28): M+H$^+$=1190.7; [MeLeu$^1$,Asp$^7$(OBn)]-CsA (SEQ ID NO:31): M+H$^+$=1281.1; [MeSer(OBn)$^1$]-CsA (SEQ ID NO:34): M+H$^+$1210.7, R$_f$=0.45 (40% acteone/hexanes); [MeSer$^1$]-CsA (SEQ ID NO:32): N+Na$^+$=1142.8, R$_f$=0.30 (40% acetone/hexanes); [MeThr(OBn)$^1$]-CsA (SEQ ID NO:35): M+H$^+$=1224.8, R$_f$=0.54 (40% acetone/hexanes); and [MeThr$^1$]-CsA (SEQ ID NO:33): M+H$^+$=1156.7, R$_f$=0.25 (40% acetone/hexanes).

11-Position Linkage to Resin

In this experiment, [MeThr(Obn)$^1$-CsA (SEQ ID NO:35) was synthesized by attaching the 11-position MeVal to the resin, synthesis of the linear undecapeptide on the solid support, followed by cleavage and cyclization in solution. Fmoc-MeVal-OH (3 equiv.) was loaded on to HMPB-PEG-PS, using DIPCDI (diisopropylcarbodiimide) (3 equiv)/HOBt (1-hydroxybenzotriazole)(3 equiv)/DMAP (dimethylaminopyridine)(0.3 equiv) in DMF (dimethylformamide), for 6 hours (See, Fields et al., J. Biol. Chem., 268:14153 [1993] for a description of this method). In most previous experiments, the amino acid (i.e., Fmoc-MeVal-OH) was attached to the resin by formation of the anhydride, followed by treatment of the resin-bound linker with this anhydride to form the ester linkage between the linker and the resin. In this method, the ester linkage between the linker and the first amino acid was directly formed using DIPCDI/HOBt and DMAP as the catalyst. Linear undecapeptide was assembled using a Millipore 9050 Plus Synthesizer with NMP (N-methyl pyrrolidinone) at 60° C. for all couplings.

All couplings proceeded smoothly, and no sluggish deprotection was observed. Cleavage from the resin was accomplished using TFA (trifluoroacetic acid)/H$_2$O/CH$_2$Cl$_2$ (dichloromethane) (5:0.5:94.5) at 20° C. Cyclization was affected using PyAOP (5.0 eqiv) and 2,6 lutidine (5.0 eqiv) in 2 mM CH$_2$Cl$_2$. Flash chromatography using a 10–40% gradient of acetone in hexanes was used to purify the CsA analog as described above. A mixture of diastereomers (4:1 ration) due to racemization at the 11-position MeVal was isolated in 14% overall yield.

From the above it should be apparent that the present invention provides immunostimulatory analogs of cyclosporin that may be useful in the study of immune cells. Specifically, they have been herein demonstrated to act as co-stimulators. It is clear that such analogs provide simpler costimulators that can be synthesized chemically.

---

We claim:

1. A method of synthesizing cyclic polypeptides containing three or more adjacent N-alkyl amino acid residues on a solid support, comprising:
   a) covalently bonding a side chain of a selected amino acid to be incorporated into the cyclic polypeptide to a solid support via a mild-acid labile or photo-labile linker to yield a support-bound residue having an N-terminus and a C-terminus;
   b) protecting the C-terminus of the support-bound residue; and then
   c) sequentially coupling C-termini of adjacent amino acids to be incorporated into the cyclic polypeptide to the N-terminus of the support-bound residue to yield a support-bound linear peptide having an N-terminus, wherein at least three adjacent amino acids are N-alkyl amino acids;
   d) repeating step c) to yield a linear analog of the cyclic polypeptide, and wherein
      when the three or more N-alkyl amino acids are coupled adjacent to one another the coupling is accomplished using a solvent comprising N-methyl pyrrolidinone in excess at a temperature ranging from about 40° C. to the boiling point of the solvent at atmospheric pressure; and then
   e) deprotecting the C-terminus of the support-bound residue and cyclizing the linear analog by treating it with a reaction solution comprising benzotriazolyl-N-oxytris(dimethylamino)phosphonium hexafluorophosphate to yield a support-bound cyclic polypeptide containing adjacent N-alkyl amino acid residues.

2. The method of claim 1, wherein a support-bound cyclic polypeptide containing eleven amino acid residues is synthesized.

3. The method of claim 1, wherein support-bound cyclosporin or a cyclosporin analog is synthesized.

4. The method of claim 1, wherein a support-bound cyclosporin analog is synthesized.

5. The method of claim 1, wherein in step e), the C-terminus of the support-bound residue is deprotected by treating with Pd(PPh$_3$)$_4$.

6. The method of claim 1, wherein in step e) the linear analog is cyclized by treating it with a reaction solution further comprising 1-hydroxybenzotriazole and diisopropylethylamine.

7. The method of claim 6, wherein the 1-hydroxybenzotriazole and diisopropylethylamine are in an equivalent ratio of approximately 1:2.

8. The method of claim 1, wherein the solid support comprises polystyrene.

9. The method of claim 1, wherein in step a) the side chain of the selected amino acid is modified by adding an allyl group thereto and the selected amino acid is bound to the linker through the allyl group.

10. The method of claim 1, wherein the linker is a mild-acid labile linker.

11. The method of claim 1, wherein the linker is a photolabile linker.

12. A method of synthesizing and cyclizing cyclosporin or cyclosporin analogs on a solid support, comprising:
   a) covalently bonding a side chain of an amino acid corresponding to position-3 or position-7 of the cyclosporin or cyclosporin analog to be synthesized to a solid support via a mild-acid labile or photo-labile linker to yield a support-bound residue having an N-terminus and a C-terminus;
   b) protecting the C-terminus of the support-bound residue; and then
   c) sequentially coupling C-termini of adjacent amino acids to be incorporated into the cyclosporin or cyclosporin analog to the N-terminus of the support-bound residue to yield a support-bound linear peptide having an N-terminus;
   d) repeating step c) to yield a linear analog of the cyclosporin or cyclosporin analog, and wherein
      when amino acids corresponding to position-11 through position-8 of the cyclosporin or cyclosporin analog are coupled the coupling is accomplished using a solvent comprising N-methyl pyrrolidinone in excess at a temperature ranging from about 40° C. to the boiling point of the solvent at atmospheric pressure; and then
   e) deprotecting the C-terminus of the support-bound residue and cyclizing the linear analog by treating it with a reaction solution comprising benzotriazolyl-N-oxy-tris(dimethylamino)phosphonium hexafluorophosphate to yield a support-bound cyclosporin or cyclosporin analog.

13. The method of claim 12, wherein in step e), the C-terminus of the support-bound residue is deprotected by treating with $Pd(PPh_3)_4$.

14. The method of claim 12, wherein in step e) the linear analog is cyclized by treating it with a reaction solution further comprising 1-hydroxybenzotriazole and diisopropylethylamine.

15. The method of claim 14, wherein the 1-hydroxybenzotriazole and diisopropylethylamine are in an equivalent ratio of approximately 1:2.

16. The method of claim 12, wherein the solid support comprises polystyrene.

17. The method of claim 12, wherein the linker is a mild-acid labile linker.

18. The method of claim 12, wherein the linker is a photolabile linker.

19. The method of claim 1, wherein in step c) at least three N-methyl amino acids are sequentially coupled.

20. The method of claim 1, wherein a cyclic polypeptide comprising -MeLeu-MeVal-MeBmt- is synthesized.

21. The method of claim 1, wherein a cyclic polypeptide comprising -MeLeu-MeVal-MeLeu- is synthesized.

22. The method of claim 1, further comprising:
   f) cleaving the support-bound cyclic peptide from the solid support.

23. The method of claim 12, wherein a cyclosporin analog selected from the group consisting of {MeLeu(3-OH)$^1$, MeAla$^{4,6}$}CsA, {MeLeu$^1$, Asp$^7$}CsA, {MeLeu(3-OH)$^1$, D-MeVal$^{11}$}CsA, {MeSer$^1$}CsA, and {MetThr$^1$}CsA is synthesized.

24. The method of claim 12, further comprising:
   f) cleaving the support-bound cyclosporin or cyclosporin analog from the solid support.

25. A method of synthesizing cyclic polypeptides comprising three or more adjacent N-alkyl amino acid residues, the method comprising:
   a) covalently bonding a selected amino acid to be incorporated into the cyclic polypeptide to a solid support via a mild-acid labile or photo-labile linker to yield a support-bound residue having an N-terminus and a C-terminus;
   b) protecting the C-terminus of the support-bound residue; and then
   c) sequentially coupling C-termini of adjacent amino acids to be incorporated into the cyclic polypeptide to the N-terminus of the support-bound residue to yield a support-bound linear peptide having an N-terminus, wherein at least three adjacent amino acids are N-alkyl amino acids;
   d) repeating step c) to yield a linear analog of the cyclic polypeptide, and wherein
      when the three or more N-alkyl amino acids are coupled adjacent to one another the coupling is accomplished using a solvent comprising N-methyl pyrrolidinone in excess at a temperature ranging from about 40° C. to the boiling point of the solvent at atmospheric pressure; and then
   e) cleaving the linear analog of the cyclic polypeptide from the solid support by treating it with acid or radiation to yield a solution-phase linear analog; and then
   f) cyclizing the solution-phase linear analog.

26. The method of claim 25, wherein cyclosporin or a cyclosporin analog is synthesized.

27. The method of claim 25, wherein a cyclic polypeptide containing N-methyl amino acid residues is synthesized.

28. The method of claim 25, wherein in step a) the selected amino acid is covalently bonded to the linker through a side chain on the selected amino acid.

29. The method of claim 25, wherein in step a) the selected amino acid is covalently bonded to the linker via an amide bond involving a C-terminus of the selected amino acid.

30. The method of claim 25, wherein in step d) each coupling is accomplished by performing the coupling twice for each added N-alkyl amino acid residue.

31. The method of claim 25, wherein in step f) the solution-phase linear analog is cyclized by treating it with 4-dimethylaminopyridine and propyl-phosphonic anhydride.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: unknown
      (D) TOPOLOGY: circular (ii) MOLECULE TYPE: peptide (ix) FEATURE:
      (A) NAME/KEY: Modified-site
      (B) LOCATION: 1
      (D) OTHER INFORMATION: /note= "MeBmt:(4R)-N-methyl-4
          -butenyl-4-methyl-L-threonine."

(ix) FEATURE:

(A) NAME/KEY: Modified-site
              (B) LOCATION: 2
              (D) OTHER INFORMATION: /note= "Abu:  alpha-aminobutyric
                  acid."

(ix) FEATURE:
              (A) NAME/KEY: Modified-site
              (B) LOCATION: 3
              (D) OTHER INFORMATION: /note= "Sar:  sarcosine."

(ix) FEATURE:
              (A) NAME/KEY: Modified-site
              (B) LOCATION: 4
              (D) OTHER INFORMATION: /note= "MeLeu:  N-methylleucine."

(ix) FEATURE:
              (A) NAME/KEY: Modified-site
              (B) LOCATION: 6
              (D) OTHER INFORMATION: /note= "MeLeu:  N-methylleucine."

(ix) FEATURE:
              (A) NAME/KEY: Modified-site
              (B) LOCATION: 8
              (D) OTHER INFORMATION: /note= "D-Ala:  D-alanine."

(ix) FEATURE:
              (A) NAME/KEY: Modified-site
              (B) LOCATION: 9..10
              (D) OTHER INFORMATION: /note= "MeLeu:  N-methylleucine."

(ix) FEATURE:
              (A) NAME/KEY: Modified-site
              (B) LOCATION: 11
              (D) OTHER INFORMATION: /note= "MeVal:  N-methylvaline."

(xi) SEQUENCE DESCRIPTION: SEQ ID NO:1:

Xaa Xaa Xaa Xaa Val Xaa Ala Xaa Xaa Xaa Xaa
1               5                   10

(2) INFORMATION FOR SEQ ID NO:2:

(i) SEQUENCE CHARACTERISTICS:
              (A) LENGTH: 4 amino acids
              (B) TYPE: amino acid
              (C) STRANDEDNESS: unknown
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "D-Ala:  D-alanine."

(ix) FEATURE:
              (A) NAME/KEY: Modified-site
              (B) LOCATION: 2..3
              (D) OTHER INFORMATION: /note= "MeLeu:  N-methylleucine."

(ix) FEATURE:
              (A) NAME/KEY: Modified-site
              (B) LOCATION: 4
              (D) OTHER INFORMATION: /note= "MeVal:  N-methylvaline."

(xi) SEQUENCE DESCRIPTION: SEQ ID NO:2:

Xaa Xaa Xaa Xaa
1

(2) INFORMATION FOR SEQ ID NO:3:

(i) SEQUENCE CHARACTERISTICS:
              (A) LENGTH: 4 amino acids
              (B) TYPE: amino acid
              (C) STRANDEDNESS: unknown
              (D) TOPOLOGY: linear

```
      (ii) MOLECULE TYPE: peptide (ix) FEATURE:
           (A) NAME/KEY: Modified-site
           (B) LOCATION: 1
           (D) OTHER INFORMATION: /note= "MeAla:  N-methylalanine."

(ix) FEATURE:
           (A) NAME/KEY: Modified-site
           (B) LOCATION: 3
           (D) OTHER INFORMATION: /note= "MeAla:  N-methylalanine."

(xi) SEQUENCE DESCRIPTION: SEQ ID NO:3:

Xaa Val Xaa Ala
1

(2) INFORMATION FOR SEQ ID NO:4:

(i) SEQUENCE CHARACTERISTICS:
           (A) LENGTH: 6 amino acids
           (B) TYPE: amino acid
           (C) STRANDEDNESS: unknown
           (D) TOPOLOGY: linear (ii) MOLECULE TYPE: peptide (ix) FEATURE:
           (A) NAME/KEY: Modified-site
           (B) LOCATION: 1
           (D) OTHER INFORMATION: /note= "Abu:  alpha-aminobutyric
                acid."

(ix) FEATURE:
           (A) NAME/KEY: Modified-site
           (B) LOCATION: 2
           (D) OTHER INFORMATION: /note= "Sar:  sarcosine."

(ix) FEATURE:
           (A) NAME/KEY: Modified-site
           (B) LOCATION: 3
           (D) OTHER INFORMATION: /note= "MeAla:  N-methylalanine."

(ix) FEATURE:
           (A) NAME/KEY: Modified-site
           (B) LOCATION: 5
           (D) OTHER INFORMATION: /note= "MeAla:  N-methylalanine."

(xi) SEQUENCE DESCRIPTION: SEQ ID NO:4:

Xaa Xaa Xaa Val Xaa Ala
1               5

(2) INFORMATION FOR SEQ ID NO:5:

(i) SEQUENCE CHARACTERISTICS:
           (A) LENGTH: 7 amino acids
           (B) TYPE: amino acid
           (C) STRANDEDNESS: unknown
           (D) TOPOLOGY: linear (ii) MOLECULE TYPE: peptide (ix) FEATURE:
           (A) NAME/KEY: Modified-site
           (B) LOCATION: 1
           (D) OTHER INFORMATION: /note= "MeLeu(3-OH):
                3-hydroxy-N-methylleucine."

(ix) FEATURE:
           (A) NAME/KEY: Modified-site
           (B) LOCATION: 2
           (D) OTHER INFORMATION: /note= "Abu:  alpha-aminobutyric
                acid."

(ix) FEATURE:
           (A) NAME/KEY: Modified-site
           (B) LOCATION: 3
```

```
        (D) OTHER INFORMATION: /note= "Sar:  sarcosine."

(ix) FEATURE:
        (A) NAME/KEY: Modified-site
        (B) LOCATION: 4
        (D) OTHER INFORMATION: /note= "MeAla:  N-methylalanine."

(ix) FEATURE:
        (A) NAME/KEY: Modified-site
        (B) LOCATION: 6
        (D) OTHER INFORMATION: /note= "MeAla:  N-methylalanine."

(xi) SEQUENCE DESCRIPTION: SEQ ID NO:5:

Xaa Xaa Xaa Xaa Val Xaa Ala
1               5

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "D-Ala:  D-alanine."

(ix) FEATURE:
        (A) NAME/KEY: Modified-site
        (B) LOCATION: 2..3
        (D) OTHER INFORMATION: /note= "MeLeu:  N-methylleucine."

(ix) FEATURE:
        (A) NAME/KEY: Modified-site
        (B) LOCATION: 4
        (D) OTHER INFORMATION: /note= "MeVal:  N-methylvaline."

(ix) FEATURE:
        (A) NAME/KEY: Modified-site
        (B) LOCATION: 5
        (D) OTHER INFORMATION: /note= "MeLeu(3-OH):
            3-hydroxy-N-methylleucine."

(ix) FEATURE:
        (A) NAME/KEY: Modified-site
        (B) LOCATION: 6
        (D) OTHER INFORMATION: /note= "Abu:  alpha-aminobutyric
            acid."

(ix) FEATURE:
        (A) NAME/KEY: Modified-site
        (B) LOCATION: 7
        (D) OTHER INFORMATION: /note= "Sar:  sarcosine."

(ix) FEATURE:
        (A) NAME/KEY: Modified-site
        (B) LOCATION: 8
        (D) OTHER INFORMATION: /note= "MeAla:  N-methylalanine."

(ix) FEATURE:
        (A) NAME/KEY: Modified-site
        (B) LOCATION: 10
        (D) OTHER INFORMATION: /note= "MeAla:  N-methylalanine."

(xi) SEQUENCE DESCRIPTION: SEQ ID NO:6:

Xaa Xaa Xaa Xaa Xaa Xaa Xaa Xaa Val Xaa Ala
1               5                   10

(2) INFORMATION FOR SEQ ID NO:7:

(i) SEQUENCE CHARACTERISTICS:
        (A) LENGTH: 11 amino acids
```

```
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "D-Ala:  D-alanine."

(ix) FEATURE:
        (A) NAME/KEY: Modified-site
        (B) LOCATION: 2..3
        (D) OTHER INFORMATION: /note= "MeLeu:  N-methylleucine."

(ix) FEATURE:
        (A) NAME/KEY: Modified-site
        (B) LOCATION: 4
        (D) OTHER INFORMATION: /note= "MeVal:  N-methylvaline."

(ix) FEATURE:
        (A) NAME/KEY: Modified-site
        (B) LOCATION: 5
        (D) OTHER INFORMATION: /note= "MeLeu(3-OH):
            3-hydroxy-N-methylleucine."

(ix) FEATURE:
        (A) NAME/KEY: Modified-site
        (B) LOCATION: 6
        (D) OTHER INFORMATION: /note= "Abu:  alpha-aminobutyric
            acid."

(ix) FEATURE:
        (A) NAME/KEY: Modified-site
        (B) LOCATION: 7
        (D) OTHER INFORMATION: /note= "Sar:  sarcosine."

(ix) FEATURE:
        (A) NAME/KEY: Modified-site
        (B) LOCATION: 8
        (D) OTHER INFORMATION: /note= "MeAla:  N-methylalanine."

(ix) FEATURE:
        (A) NAME/KEY: Modified-site
        (B) LOCATION: 10
        (D) OTHER INFORMATION: /note= "MeAla:  N-methylalanine."

(xi) SEQUENCE DESCRIPTION: SEQ ID NO:7:

Xaa Xaa Xaa Xaa Xaa Xaa Xaa Xaa Val Xaa Ala
1               5                   10

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "MeLeu(3-OH):
            3-hydroxy-N-methylleucine."

(ix) FEATURE:
        (A) NAME/KEY: Modified-site
        (B) LOCATION: 2
        (D) OTHER INFORMATION: /note= "Abu:  alpha-aminobutyric
            acid."

(ix) FEATURE:
        (A) NAME/KEY: Modified-site
        (B) LOCATION: 3
        (D) OTHER INFORMATION: /note= "Sar:  sarcosine."
```

(ix) FEATURE:
              (A) NAME/KEY: Modified-site
              (B) LOCATION: 4
              (D) OTHER INFORMATION: /note= "MeLeu:  N-methylleucine."

(ix) FEATURE:
              (A) NAME/KEY: Modified-site
              (B) LOCATION: 6
              (D) OTHER INFORMATION: /note= "MeLeu:  N-methylleucine."

(xi) SEQUENCE DESCRIPTION: SEQ ID NO:8:

Xaa Xaa Xaa Xaa Val Xaa Ala
1               5

(2) INFORMATION FOR SEQ ID NO:9:

(i) SEQUENCE CHARACTERISTICS:
              (A) LENGTH: 11 amino acids
              (B) TYPE: amino acid
              (C) STRANDEDNESS: unknown
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "D-Ala:  D-alanine."

(ix) FEATURE:
              (A) NAME/KEY: Modified-site
              (B) LOCATION: 2..3
              (D) OTHER INFORMATION: /note= "MeLeu:  N-methylleucine."

(ix) FEATURE:
              (A) NAME/KEY: Modified-site
              (B) LOCATION: 4
              (D) OTHER INFORMATION: /note= "D-MeVal:
                  D-N-methylvaline."

(ix) FEATURE:
              (A) NAME/KEY: Modified-site
              (B) LOCATION: 5
              (D) OTHER INFORMATION: /note= "MeLeu(OH):
                  hydroxy-N-methylleucine."

(ix) FEATURE:
              (A) NAME/KEY: Modified-site
              (B) LOCATION: 6
              (D) OTHER INFORMATION: /note= "Abu:  alpha-aminobutyric
                  acid."

(ix) FEATURE:
              (A) NAME/KEY: Modified-site
              (B) LOCATION: 7
              (D) OTHER INFORMATION: /note= "Sar:  sarcosine."

(ix) FEATURE:
              (A) NAME/KEY: Modified-site
              (B) LOCATION: 8
              (D) OTHER INFORMATION: /note= "MeLeu:  N-methylleucine."

(ix) FEATURE:
              (A) NAME/KEY: Modified-site
              (B) LOCATION: 10
              (D) OTHER INFORMATION: /note= "MeLeu:  N-methylleucine."

(xi) SEQUENCE DESCRIPTION: SEQ ID NO:9:

Xaa Xaa Xaa Xaa Xaa Xaa Xaa Xaa Val Xaa Ala
1               5                   10

(2) INFORMATION FOR SEQ ID NO:10:

(i) SEQUENCE CHARACTERISTICS:
              (A) LENGTH: 7 amino acids (B) TYPE: amino acid
         (C) STRANDEDNESS: unknown
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "MeBmt:(4R)-N-methyl
             -4-butenyl-4-methyl-L-threonine."

(ix) FEATURE:
         (A) NAME/KEY: Modified-site
         (B) LOCATION: 2
         (D) OTHER INFORMATION: /note= "Abu:  alpha-aminobutyric
             acid."

(ix) FEATURE:
         (A) NAME/KEY: Modified-site
         (B) LOCATION: 3
         (D) OTHER INFORMATION: /note= "Sar:  sarcosine."

(ix) FEATURE:
         (A) NAME/KEY: Modified-site
         (B) LOCATION: 4
         (D) OTHER INFORMATION: /note= "MeLeu:  N-methylleucine."

(ix) FEATURE:
         (A) NAME/KEY: Modified-site
         (B) LOCATION: 6
         (D) OTHER INFORMATION: /note= "MeLeu:  N-methylleucine."

(xi) SEQUENCE DESCRIPTION: SEQ ID NO:10:

Xaa Xaa Xaa Xaa Val Xaa Ala
1               5

(2) INFORMATION FOR SEQ ID NO:11:

(i) SEQUENCE CHARACTERISTICS:
         (A) LENGTH: 11 amino acids
         (B) TYPE: amino acid
         (C) STRANDEDNESS: unknown
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "D-Ala:  D-alanine."

(ix) FEATURE:
         (A) NAME/KEY: Modified-site
         (B) LOCATION: 2..3
         (D) OTHER INFORMATION: /note= "MeLeu:  N-methylleucine."

(ix) FEATURE:
         (A) NAME/KEY: Modified-site
         (B) LOCATION: 4
         (D) OTHER INFORMATION: /note= "D-MeVal:
             D-N-methylvaline."

(ix) FEATURE:
         (A) NAME/KEY: Modified-site
         (B) LOCATION: 5
         (D) OTHER INFORMATION: /note= "MeBmt: (4R)-N-methyl
             -4-butenyl-4-methyl-L-threonine."

(ix) FEATURE:
         (A) NAME/KEY: Modified-site
         (B) LOCATION: 6
         (D) OTHER INFORMATION: /note= "Abu:  alpha-aminobutyric
             acid."

(ix) FEATURE:
         (A) NAME/KEY: Modified-site
         (B) LOCATION: 7

(D) OTHER INFORMATION: /note= "Sar: sarcosine."

(ix) FEATURE:
            (A) NAME/KEY: Modified-site
            (B) LOCATION: 8
            (D) OTHER INFORMATION: /note= "MeLeu: N-methylleucine."

(ix) FEATURE:
            (A) NAME/KEY: Modified-site
            (B) LOCATION: 10
            (D) OTHER INFORMATION: /note= "MeLeu: N-methylleucine."

(xi) SEQUENCE DESCRIPTION: SEQ ID NO:11:

Xaa Xaa Xaa Xaa Xaa Xaa Xaa Xaa Val Xaa Ala
1               5                   10

(2) INFORMATION FOR SEQ ID NO:12:

(i) SEQUENCE CHARACTERISTICS:
            (A) LENGTH: 11 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /note= "MeLeu: N-methylleucine."

(ix) FEATURE:
            (A) NAME/KEY: Modified-site
            (B) LOCATION: 4
            (D) OTHER INFORMATION: /note= "MeLeu: N-methylleucine."

(ix) FEATURE:
            (A) NAME/KEY: Modified-site
            (B) LOCATION: 5
            (D) OTHER INFORMATION: /note= "Sar: sarcosine."

(ix) FEATURE:
            (A) NAME/KEY: Modified-site
            (B) LOCATION: 6
            (D) OTHER INFORMATION: /note= "Abu: alpha-aminobutyric
                acid."

(ix) FEATURE:
            (A) NAME/KEY: Modified-site
            (B) LOCATION: 7
            (D) OTHER INFORMATION: /note= "MeLeu: N-methylleucine."

(ix) FEATURE:
            (A) NAME/KEY: Modified-site
            (B) LOCATION: 8
            (D) OTHER INFORMATION: /note= "MeVal: N-methylvaline."

(ix) FEATURE:
            (A) NAME/KEY: Modified-site
            (B) LOCATION: 9..10
            (D) OTHER INFORMATION: /note= "MeLeu: N-methylleucine."

(ix) FEATURE:
            (A) NAME/KEY: Modified-site
            (B) LOCATION: 11
            (D) OTHER INFORMATION: /note= "D-Ala: D-alanine."

(xi) SEQUENCE DESCRIPTION: SEQ ID NO:12:

Ala Xaa Val Xaa Xaa Xaa Xaa Xaa Xaa Xaa Xaa
1               5                   10

(2) INFORMATION FOR SEQ ID NO:13:

(i) SEQUENCE CHARACTERISTICS:
            (A) LENGTH: 4 amino acids
            (B) TYPE: amino acid

```
          (C) STRANDEDNESS: unknown
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /note= "MeLeu:  N-methylleucine."

(ix) FEATURE:
          (A) NAME/KEY: Modified-site
          (B) LOCATION: 4
          (D) OTHER INFORMATION: /note= "MeLeu:  N-methylleucine."

(xi) SEQUENCE DESCRIPTION: SEQ ID NO:13:

Ala Xaa Val Xaa
1

(2) INFORMATION FOR SEQ ID NO:14:

(i) SEQUENCE CHARACTERISTICS:
          (A) LENGTH: 5 amino acids
          (B) TYPE: amino acid
          (C) STRANDEDNESS: unknown
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /note= "MeLeu:  N-methylleucine."

(ix) FEATURE:
          (A) NAME/KEY: Modified-site
          (B) LOCATION: 4
          (D) OTHER INFORMATION: /note= "MeLeu:  N-methylleucine."

(ix) FEATURE:
          (A) NAME/KEY: Modified-site
          (B) LOCATION: 5
          (D) OTHER INFORMATION: /note= "Sar:  sarcosine."

(xi) SEQUENCE DESCRIPTION: SEQ ID NO:14:

Ala Xaa Val Xaa Xaa
1               5

(2) INFORMATION FOR SEQ ID NO:15:

(i) SEQUENCE CHARACTERISTICS:
          (A) LENGTH: 5 amino acids
          (B) TYPE: amino acid
          (C) STRANDEDNESS: unknown
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /note= "MeLeu:  N-methylleucine."

(ix) FEATURE:
          (A) NAME/KEY: Modified-site
          (B) LOCATION: 4
          (D) OTHER INFORMATION: /note= "MeLeu:  N-methylleucine."

(ix) FEATURE:
          (A) NAME/KEY: Modified-site
          (B) LOCATION: 5
          (D) OTHER INFORMATION: /note= "Abu:  alpha-aminobutyric
               acid."

(xi) SEQUENCE DESCRIPTION: SEQ ID NO:15:
```

```
Ala Xaa Val Xaa Xaa
 1           5
```

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "MeLeu:  N-methylleucine."

(ix) FEATURE:
        (A) NAME/KEY: Modified-site
        (B) LOCATION: 4
        (D) OTHER INFORMATION: /note= "MeLeu:  N-methylleucine."

(ix) FEATURE:
        (A) NAME/KEY: Modified-site
        (B) LOCATION: 5
        (D) OTHER INFORMATION: /note= "Abu:  alpha-aminobutyric
            acid."

(ix) FEATURE:
        (A) NAME/KEY: Modified-site
        (B) LOCATION: 6
        (D) OTHER INFORMATION: /note= "MeLeu:  N-methylleucine."

(xi) SEQUENCE DESCRIPTION: SEQ ID NO:16:

```
Ala Xaa Val Xaa Xaa Xaa
 1           5
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "MeLeu:  N-methylleucine."

(ix) FEATURE:
        (A) NAME/KEY: Modified-site
        (B) LOCATION: 4
        (D) OTHER INFORMATION: /note= "MeLeu:  N-methylleucine."

(ix) FEATURE:
        (A) NAME/KEY: Modified-site
        (B) LOCATION: 5
        (D) OTHER INFORMATION: /note= "Abu:  alpha-aminobutyric
            acid."

(ix) FEATURE:
        (A) NAME/KEY: Modified-site
        (B) LOCATION: 6
        (D) OTHER INFORMATION: /note= "MeLeu:  N-methylleucine."

(ix) FEATURE:
        (A) NAME/KEY: Modified-site
        (B) LOCATION: 7
        (D) OTHER INFORMATION: /note= "MeVal:  N-methylvaline."

(xi) SEQUENCE DESCRIPTION: SEQ ID NO:17:

```
Ala Xaa Val Xaa Xaa Xaa Xaa
```

1          5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "MeLeu:  N-methylleucine."

(ix) FEATURE:
        (A) NAME/KEY: Modified-site
        (B) LOCATION: 4
        (D) OTHER INFORMATION: /note= "MeLeu:  N-methylleucine."

(ix) FEATURE:
        (A) NAME/KEY: Modified-site
        (B) LOCATION: 5
        (D) OTHER INFORMATION: /note= "Abu:   alpha-aminobutyric
            acid."

(ix) FEATURE:
        (A) NAME/KEY: Modified-site
        (B) LOCATION: 6
        (D) OTHER INFORMATION: /note= "MeLeu:  N-methylleucine."

(ix) FEATURE:
        (A) NAME/KEY: Modified-site
        (B) LOCATION: 7
        (D) OTHER INFORMATION: /note= "MeVal:  N-methylvaline."

(ix) FEATURE:
        (A) NAME/KEY: Modified-site
        (B) LOCATION: 8
        (D) OTHER INFORMATION: /note= "MeLeu:  N-methylleucine."

(xi) SEQUENCE DESCRIPTION: SEQ ID NO:18:

Ala Xaa Val Xaa Xaa Xaa Xaa Xaa
1               5

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "MeLeu:  N-methylleucine."

(ix) FEATURE:
        (A) NAME/KEY: Modified-site
        (B) LOCATION: 4
        (D) OTHER INFORMATION: /note= "MeLeu:  N-methylleucine."

(ix) FEATURE:
        (A) NAME/KEY: Modified-site
        (B) LOCATION: 5
        (D) OTHER INFORMATION: /note= "Abu:   alpha-aminobutyric
            acid."

(ix) FEATURE:
        (A) NAME/KEY: Modified-site
        (B) LOCATION: 6
        (D) OTHER INFORMATION: /note= "MeLeu:  N-methylleucine."

(ix) FEATURE:
            (A) NAME/KEY: Modified-site
            (B) LOCATION: 7
            (D) OTHER INFORMATION: /note= "MeVal:  N-methylvaline."

(ix) FEATURE:
            (A) NAME/KEY: Modified-site
            (B) LOCATION: 8..9
            (D) OTHER INFORMATION: /note= "MeLeu:  N-methylleucine."

(xi) SEQUENCE DESCRIPTION: SEQ ID NO:19:

Ala Xaa Val Xaa Xaa Xaa Xaa Xaa Xaa
1               5

(2) INFORMATION FOR SEQ ID NO:20:

(i) SEQUENCE CHARACTERISTICS:
            (A) LENGTH: 10 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /note= "MeLeu:  N-methylleucine."

(ix) FEATURE:
            (A) NAME/KEY: Modified-site
            (B) LOCATION: 4
            (D) OTHER INFORMATION: /note= "MeLeu:  N-methylleucine."

(ix) FEATURE:
            (A) NAME/KEY: Modified-site
            (B) LOCATION: 5
            (D) OTHER INFORMATION: /note= "Abu:   alpha-aminobutyric
                 acid."

(ix) FEATURE:
            (A) NAME/KEY: Modified-site
            (B) LOCATION: 6
            (D) OTHER INFORMATION: /note= "MeLeu:  N-methylleucine."

(ix) FEATURE:
            (A) NAME/KEY: Modified-site
            (B) LOCATION: 7
            (D) OTHER INFORMATION: /note= "MeVal:  N-methylvaline."

(ix) FEATURE:
            (A) NAME/KEY: Modified-site
            (B) LOCATION: 8..9
            (D) OTHER INFORMATION: /note= "MeLeu:  N-methylleucine."

(ix) FEATURE:
            (A) NAME/KEY: Modified-site
            (B) LOCATION: 10
            (D) OTHER INFORMATION: /note= "D-Ala:  D-alanine."

(xi) SEQUENCE DESCRIPTION: SEQ ID NO:20:

Ala Xaa Val Xaa Xaa Xaa Xaa Xaa Xaa Xaa
1               5                   10

(2) INFORMATION FOR SEQ ID NO:21:

(i) SEQUENCE CHARACTERISTICS:
            (A) LENGTH: 11 amino acids
            (B) TYPE: amino acid
            (C) STRANDEDNESS: unknown
            (D) TOPOLOGY: circular (ii) MOLECULE TYPE: peptide (ix) FEATURE:

(A) NAME/KEY: Modified-site
            (B) LOCATION: 1
            (D) OTHER INFORMATION: /note= "MeLeu(3-OH):
                3-hydroxy-N-methylleucine."

(ix) FEATURE:
            (A) NAME/KEY: Modified-site
            (B) LOCATION: 2
            (D) OTHER INFORMATION: /note= "Abu:  alpha-aminobutyric
                acid."

(ix) FEATURE:
            (A) NAME/KEY: Modified-site
            (B) LOCATION: 3
            (D) OTHER INFORMATION: /note= "Sar:  sarcosine."

(ix) FEATURE:
            (A) NAME/KEY: Modified-site
            (B) LOCATION: 4
            (D) OTHER INFORMATION: /note= "MeAla:  N-methylalanine."

(ix) FEATURE:
            (A) NAME/KEY: Modified-site
            (B) LOCATION: 6
            (D) OTHER INFORMATION: /note= "MeAla:  N-methylalanine."

(ix) FEATURE:
            (A) NAME/KEY: Modified-site
            (B) LOCATION: 8
            (D) OTHER INFORMATION: /note= "D-Ala:  D-alanine."

(ix) FEATURE:
            (A) NAME/KEY: Modified-site
            (B) LOCATION: 9..10
            (D) OTHER INFORMATION: /note= "MeLeu:  N-methylleucine."

(ix) FEATURE:
            (A) NAME/KEY: Modified-site
            (B) LOCATION: 11
            (D) OTHER INFORMATION: /note= "MeVal:  N-methylvaline."

(xi) SEQUENCE DESCRIPTION: SEQ ID NO:21:

Xaa Xaa Xaa Xaa Val Xaa Ala Xaa Xaa Xaa Xaa
1               5                   10

(2) INFORMATION FOR SEQ ID NO:22:

(i) SEQUENCE CHARACTERISTICS:
            (A) LENGTH: 4 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "MeLeu:  N-methylleucine."

(ix) FEATURE:
            (A) NAME/KEY: Modified-site
            (B) LOCATION: 3
            (D) OTHER INFORMATION: /note= "MeLeu:  N-methylleucine."

(xi) SEQUENCE DESCRIPTION: SEQ ID NO:22:

Xaa Val Xaa Ala
1

(2) INFORMATION FOR SEQ ID NO:23:

(i) SEQUENCE CHARACTERISTICS:
            (A) LENGTH: 4 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "MeLeu: N-methylleucine."

(ix) FEATURE:
            (A) NAME/KEY: Modified-site
            (B) LOCATION: 3
            (D) OTHER INFORMATION: /note= "MeAla: N-methylalanine."

(xi) SEQUENCE DESCRIPTION: SEQ ID NO:23:

Xaa Val Xaa Ala
1

(2) INFORMATION FOR SEQ ID NO:24:

(i) SEQUENCE CHARACTERISTICS:
            (A) LENGTH: 6 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Abu: alpha-aminobutyric
                acid."

(ix) FEATURE:
            (A) NAME/KEY: Modified-site
            (B) LOCATION: 2
            (D) OTHER INFORMATION: /note= "Sar: sarcosine."

(ix) FEATURE:
            (A) NAME/KEY: Modified-site
            (B) LOCATION: 3
            (D) OTHER INFORMATION: /note= "MeLeu: N-methylleucine."

(ix) FEATURE:
            (A) NAME/KEY: Modified-site
            (B) LOCATION: 5
            (D) OTHER INFORMATION: /note= "MeLeu: N-methylleucine."

(xi) SEQUENCE DESCRIPTION: SEQ ID NO:24:

Xaa Xaa Xaa Val Xaa Ala
1               5

(2) INFORMATION FOR SEQ ID NO:25:

(i) SEQUENCE CHARACTERISTICS:
            (A) LENGTH: 6 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Abu: alpha-aminobutyric
                acid."

(ix) FEATURE:
            (A) NAME/KEY: Modified-site
            (B) LOCATION: 2
            (D) OTHER INFORMATION: /note= "Sar: sarcosine."

(ix) FEATURE:
            (A) NAME/KEY: Modified-site
            (B) LOCATION: 3

(D) OTHER INFORMATION: /note= "MeLeu:  N-methylleucine."

(ix) FEATURE:
                (A) NAME/KEY: Modified-site
                (B) LOCATION: 5
                (D) OTHER INFORMATION: /note= "MeAla:  N-methylalanine."

(xi) SEQUENCE DESCRIPTION: SEQ ID NO:25:

Xaa Xaa Xaa Val Xaa Ala
1               5

(2) INFORMATION FOR SEQ ID NO:26:

(i) SEQUENCE CHARACTERISTICS:
                (A) LENGTH: 6 amino acids
                (B) TYPE: amino acid
                (C) STRANDEDNESS: unknown
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note= "Abu:  alpha-aminobutyric
                    acid."

(ix) FEATURE:
                (A) NAME/KEY: Modified-site
                (B) LOCATION: 2
                (D) OTHER INFORMATION: /note= "Sar:  sarcosine."

(ix) FEATURE:
                (A) NAME/KEY: Modified-site
                (B) LOCATION: 3
                (D) OTHER INFORMATION: /note= "MeAla:  N-methylalanine."

(ix) FEATURE:
                (A) NAME/KEY: Modified-site
                (B) LOCATION: 5
                (D) OTHER INFORMATION: /note= "MeAla:  N-methylalanine."

(xi) SEQUENCE DESCRIPTION: SEQ ID NO:26:

Xaa Xaa Xaa Val Xaa Ala
1               5

(2) INFORMATION FOR SEQ ID NO:27:

(i) SEQUENCE CHARACTERISTICS:
                (A) LENGTH: 11 amino acids
                (B) TYPE: amino acid
                (C) STRANDEDNESS: unknown
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note= "D-Ala:  D-alanine."

(ix) FEATURE:
                (A) NAME/KEY: Modified-site
                (B) LOCATION: 2..3
                (D) OTHER INFORMATION: /note= "MeLeu:  N-methylleucine."

(ix) FEATURE:
                (A) NAME/KEY: Modified-site
                (B) LOCATION: 4
                (D) OTHER INFORMATION: /note= "D-MeVal: D-N-methylvaline."

(ix) FEATURE:
                (A) NAME/KEY: Modified-site
                (B) LOCATION: 5
                (D) OTHER INFORMATION: /note= "MeBmt: (4R)
                    -N-methyl-4-butenyl-4-methyl-L-threonine."

(ix) FEATURE:
    (A) NAME/KEY: Modified-site
    (B) LOCATION: 6
    (D) OTHER INFORMATION: /note= "Abu:  alpha-aminobutyric
        acid."

(ix) FEATURE:
    (A) NAME/KEY: Modified-site
    (B) LOCATION: 7
    (D) OTHER INFORMATION: /note= "Sar:  sarcosine."

(ix) FEATURE:
    (A) NAME/KEY: Modified-site
    (B) LOCATION: 8
    (D) OTHER INFORMATION: /note= "MeLeu:  N-methylleucine."

(ix) FEATURE:
    (A) NAME/KEY: Modified-site
    (B) LOCATION: 10
    (D) OTHER INFORMATION: /note= "MeLeu:  N-methylleucine."

(xi) SEQUENCE DESCRIPTION: SEQ ID NO:27:

Xaa Xaa Xaa Xaa Xaa Xaa Xaa Xaa Val Xaa Ala
1               5                   10

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "MeLeu: N-methylleucine."

(ix) FEATURE:
        (A) NAME/KEY: Modified-site
        (B) LOCATION: 2
        (D) OTHER INFORMATION: /note= "Abu:  alpha-aminobutyric
            acid."

(ix) FEATURE:
        (A) NAME/KEY: Modified-site
        (B) LOCATION: 3
        (D) OTHER INFORMATION: /note= "Sar:  sarcosine."

(ix) FEATURE:
        (A) NAME/KEY: Modified-site
        (B) LOCATION: 4
        (D) OTHER INFORMATION: /note= "MeLeu:  N-methylleucine."

(ix) FEATURE:
        (A) NAME/KEY: Modified-site
        (B) LOCATION: 6
        (D) OTHER INFORMATION: /note= "MeLeu:  N-methylleucine."

(ix) FEATURE:
        (A) NAME/KEY: Modified-site
        (B) LOCATION: 8
        (D) OTHER INFORMATION: /note= "D-Ala:  D-alanine."

(ix) FEATURE:
        (A) NAME/KEY: Modified-site
        (B) LOCATION: 9..10
        (D) OTHER INFORMATION: /note= "MeLeu:  N-methylleucine."

(ix) FEATURE:
        (A) NAME/KEY: Modified-site
        (B) LOCATION: 11
        (D) OTHER INFORMATION: /note= "MeVal:  N-methylvaline."

(xi) SEQUENCE DESCRIPTION: SEQ ID NO:28:

```
Xaa Xaa Xaa Xaa Val Xaa Asp Xaa Xaa Xaa Xaa
1               5               10
```

(2) INFORMATION FOR SEQ ID NO:29:

(i) SEQUENCE CHARACTERISTICS:
        (A) LENGTH: 7 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "MeLeu: N-methylleucine."

(ix) FEATURE:
        (A) NAME/KEY: Modified-site
        (B) LOCATION: 2
        (D) OTHER INFORMATION: /note= "Abu: alpha-aminobutyric acid."

(ix) FEATURE:
        (A) NAME/KEY: Modified-site
        (B) LOCATION: 3
        (D) OTHER INFORMATION: /note= "Sar: sarcosine."

(ix) FEATURE:
        (A) NAME/KEY: Modified-site
        (B) LOCATION: 4
        (D) OTHER INFORMATION: /note= "MeLeu: N-methylleucine."

(ix) FEATURE:
        (A) NAME/KEY: Modified-site
        (B) LOCATION: 6
        (D) OTHER INFORMATION: /note= "MeLeu: N-methylleucine."

(xi) SEQUENCE DESCRIPTION: SEQ ID NO:29:

```
Xaa Xaa Xaa Xaa Val Xaa Asp
1               5
```

(2) INFORMATION FOR SEQ ID NO:30:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "D-Ala: D-alanine."

(ix) FEATURE:
        (A) NAME/KEY: Modified-site
        (B) LOCATION: 2..3
        (D) OTHER INFORMATION: /note= "MeLeu: N-methylleucine."

(ix) FEATURE:
        (A) NAME/KEY: Modified-site
        (B) LOCATION: 4
        (D) OTHER INFORMATION: /note= "MeVal: N-methylvaline."

(ix) FEATURE:
        (A) NAME/KEY: Modified-site
        (B) LOCATION: 5
        (D) OTHER INFORMATION: /note= "MeLeu: N-methylleucine."

(ix) FEATURE:
        (A) NAME/KEY: Modified-site
        (B) LOCATION: 6

(D) OTHER INFORMATION: /note= "Abu:  alpha-aminobutyric
                acid."

(ix) FEATURE:
            (A) NAME/KEY: Modified-site
            (B) LOCATION: 7
            (D) OTHER INFORMATION: /note= "Sar:  sarcosine."

(ix) FEATURE:
            (A) NAME/KEY: Modified-site
            (B) LOCATION: 8
            (D) OTHER INFORMATION: /note= "MeLeu: N-methylleucine."

(ix) FEATURE:
            (A) NAME/KEY: Modified-site
            (B) LOCATION: 10
            (D) OTHER INFORMATION: /note= "MeLeu: N-methylleucine."

(xi) SEQUENCE DESCRIPTION: SEQ ID NO:30:

Xaa Xaa Xaa Xaa Xaa Xaa Xaa Xaa Val Xaa Asp
1               5                   10

(2) INFORMATION FOR SEQ ID NO:31:

(i) SEQUENCE CHARACTERISTICS:
            (A) LENGTH: 11 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Modified-site
            (B) LOCATION: 1
            (D) OTHER INFORMATION: /note= "MeLeu: N-methylleucine."

(ix) FEATURE:
            (A) NAME/KEY: Modified-site
            (B) LOCATION: 2
            (D) OTHER INFORMATION: /note= "Abu:  alpha-aminobutyric
                acid."

(ix) FEATURE:
            (A) NAME/KEY: Modified-site
            (B) LOCATION: 3
            (D) OTHER INFORMATION: /note= "Sar:  sarcosine."

(ix) FEATURE:
            (A) NAME/KEY: Modified-site
            (B) LOCATION: 4
            (D) OTHER INFORMATION: /note= "MeLeu:  N-methylleucine."

(ix) FEATURE:
            (A) NAME/KEY: Modified-site
            (B) LOCATION: 6
            (D) OTHER INFORMATION: /note= "MeLeu:  N-methylleucine."

(ix) FEATURE:
            (A) NAME/KEY: Modified-site
            (B) LOCATION: 8
            (D) OTHER INFORMATION: /note= "D-Ala:  D-alanine."

(ix) FEATURE:
            (A) NAME/KEY: Modified-site
            (B) LOCATION: 9..10
            (D) OTHER INFORMATION: /note= "MeLeu:  N-methylleucine."

(ix) FEATURE:
            (A) NAME/KEY: Modified-site
            (B) LOCATION: 11
            (D) OTHER INFORMATION: /note= "MeVal:  N-methylvaline."

(xi) SEQUENCE DESCRIPTION: SEQ ID NO:31:

Xaa Xaa Xaa Xaa Val Xaa Asp Xaa Xaa Xaa Xaa
1               5                   10

(2) INFORMATION FOR SEQ ID NO:32:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "MeSer: N-methylserine."

(ix) FEATURE:
        (A) NAME/KEY: Modified-site
        (B) LOCATION: 2
        (D) OTHER INFORMATION: /note= "Abu: alpha-aminobutyric
            acid."

(ix) FEATURE:
        (A) NAME/KEY: Modified-site
        (B) LOCATION: 3
        (D) OTHER INFORMATION: /note= "Sar: sarcosine."

(ix) FEATURE:
        (A) NAME/KEY: Modified-site
        (B) LOCATION: 4
        (D) OTHER INFORMATION: /note= "MeLeu: N-methylleucine."

(ix) FEATURE:
        (A) NAME/KEY: Modified-site
        (B) LOCATION: 6
        (D) OTHER INFORMATION: /note= "MeLeu: N-methylleucine."

(ix) FEATURE:
        (A) NAME/KEY: Modified-site
        (B) LOCATION: 8
        (D) OTHER INFORMATION: /note= "D-Ala: D-alanine."

(ix) FEATURE:
        (A) NAME/KEY: Modified-site
        (B) LOCATION: 9..10
        (D) OTHER INFORMATION: /note= "MeLeu: N-methylleucine."

(ix) FEATURE:
        (A) NAME/KEY: Modified-site
        (B) LOCATION: 11
        (D) OTHER INFORMATION: /note= "MeVal: N-methylvaline."

(xi) SEQUENCE DESCRIPTION: SEQ ID NO:32:

Xaa Xaa Xaa Xaa Val Xaa Ala Xaa Xaa Xaa Xaa
1               5                  10

(2) INFORMATION FOR SEQ ID NO:33:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "MeThr: N-methylthreonine."

(ix) FEATURE:
        (A) NAME/KEY: Modified-site
        (B) LOCATION: 2
        (D) OTHER INFORMATION: /note= "Abu: alpha-aminobutyric
            acid."

(ix) FEATURE:

```
        (A) NAME/KEY: Modified-site
        (B) LOCATION: 3
        (D) OTHER INFORMATION: /note= "Sar:  sarcosine."

(ix) FEATURE:
        (A) NAME/KEY: Modified-site
        (B) LOCATION: 4
        (D) OTHER INFORMATION: /note= "MeLeu:  N-methylleucine."

(ix) FEATURE:
        (A) NAME/KEY: Modified-site
        (B) LOCATION: 6
        (D) OTHER INFORMATION: /note= "MeLeu:  N-methylleucine."

(ix) FEATURE:
        (A) NAME/KEY: Modified-site
        (B) LOCATION: 8
        (D) OTHER INFORMATION: /note= "D-Ala:  D-alanine."

(ix) FEATURE:
        (A) NAME/KEY: Modified-site
        (B) LOCATION: 9..10
        (D) OTHER INFORMATION: /note= "MeLeu:  N-methylleucine."

(ix) FEATURE:
        (A) NAME/KEY: Modified-site
        (B) LOCATION: 11
        (D) OTHER INFORMATION: /note= "MeVal:  N-methylvaline."

(xi) SEQUENCE DESCRIPTION: SEQ ID NO:33:

Xaa Xaa Xaa Xaa Val Xaa Ala Xaa Xaa Xaa Xaa
1               5                   10

(2) INFORMATION FOR SEQ ID NO:34:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "MeSer: N-methylserine benzyl
            ester."

(ix) FEATURE:
        (A) NAME/KEY: Modified-site
        (B) LOCATION: 2
        (D) OTHER INFORMATION: /note= "Abu:  alpha-aminobutyric
            acid."

(ix) FEATURE:
        (A) NAME/KEY: Modified-site
        (B) LOCATION: 3
        (D) OTHER INFORMATION: /note= "Sar:  sarcosine."

(ix) FEATURE:
        (A) NAME/KEY: Modified-site
        (B) LOCATION: 4
        (D) OTHER INFORMATION: /note= "MeLeu:  N-methylleucine."

(ix) FEATURE:
        (A) NAME/KEY: Modified-site
        (B) LOCATION: 6
        (D) OTHER INFORMATION: /note= "MeLeu:  N-methylleucine."

(ix) FEATURE:
        (A) NAME/KEY: Modified-site
        (B) LOCATION: 8
        (D) OTHER INFORMATION: /note= "D-Ala:  D-alanine."

(ix) FEATURE:
        (A) NAME/KEY: Modified-site
        (B) LOCATION: 9..10
```

(D) OTHER INFORMATION: /note= "MeLeu:  N-methylleucine."

(ix) FEATURE:
         (A) NAME/KEY: Modified-site
         (B) LOCATION: 11
         (D) OTHER INFORMATION: /note= "MeVal:  N-methylvaline."

(xi) SEQUENCE DESCRIPTION: SEQ ID NO:34:

Xaa Xaa Xaa Xaa Val Xaa Ala Xaa Xaa Xaa Xaa
1               5                   10

(2) INFORMATION FOR SEQ ID NO:35:

(i) SEQUENCE CHARACTERISTICS:
         (A) LENGTH: 11 amino acids
         (B) TYPE: amino acid
         (C) STRANDEDNESS: unknown
         (D) TOPOLOGY: circular (ii) MOLECULE TYPE: peptide (ix) FEATURE:
         (A) NAME/KEY: Modified-site
         (B) LOCATION: 1
         (D) OTHER INFORMATION: /note= "MeThr: N-methylthreonine benzyl
              ester."

(ix) FEATURE:
         (A) NAME/KEY: Modified-site
         (B) LOCATION: 2
         (D) OTHER INFORMATION: /note= "Abu:   alpha-aminobutyric
              acid."

(ix) FEATURE:
         (A) NAME/KEY: Modified-site
         (B) LOCATION: 3
         (D) OTHER INFORMATION: /note= "Sar:   sarcosine."

(ix) FEATURE:
         (A) NAME/KEY: Modified-site
         (B) LOCATION: 4
         (D) OTHER INFORMATION: /note= "MeLeu:  N-methylleucine."

(ix) FEATURE:
         (A) NAME/KEY: Modified-site
         (B) LOCATION: 6
         (D) OTHER INFORMATION: /note= "MeLeu:  N-methylleucine."

(ix) FEATURE:
         (A) NAME/KEY: Modified-site
         (B) LOCATION: 8
         (D) OTHER INFORMATION: /note= "D-Ala:  D-alanine."

(ix) FEATURE:
         (A) NAME/KEY: Modified-site
         (B) LOCATION: 9..10
         (D) OTHER INFORMATION: /note= "MeLeu:  N-methylleucine."

(ix) FEATURE:
         (A) NAME/KEY: Modified-site
         (B) LOCATION: 11
         (D) OTHER INFORMATION: /note= "MeVal:  N-methylvaline."

(xi) SEQUENCE DESCRIPTION: SEQ ID NO:35:

Xaa Xaa Xaa Xaa Val Xaa Ala Xaa Xaa Xaa Xaa
1               5                   10

(2) INFORMATION FOR SEQ ID NO:36:

(i) SEQUENCE CHARACTERISTICS:
         (A) LENGTH: 11 amino acids
         (B) TYPE: amino acid
         (C) STRANDEDNESS: unknown
         (D) TOPOLOGY: circular (ii) MOLECULE TYPE: peptide (ix) FEATURE:
            (A) NAME/KEY: Modified-site
            (B) LOCATION: 1
            (D) OTHER INFORMATION: /note= "MeLeu: N-methylleucine."

(ix) FEATURE:
            (A) NAME/KEY: Modified-site
            (B) LOCATION: 2
            (D) OTHER INFORMATION: /note= "Abu:  alpha-aminobutyric
                acid."

(ix) FEATURE:
            (A) NAME/KEY: Modified-site
            (B) LOCATION: 3
            (D) OTHER INFORMATION: /note= "Sar:  sarcosine."

(ix) FEATURE:
            (A) NAME/KEY: Modified-site
            (B) LOCATION: 4
            (D) OTHER INFORMATION: /note= "MeLeu:  N-methylleucine."

(ix) FEATURE:
            (A) NAME/KEY: Modified-site
            (B) LOCATION: 6
            (D) OTHER INFORMATION: /note= "MeLeu:  N-methylleucine."

(ix) FEATURE:
            (A) NAME/KEY: Modified-site
            (B) LOCATION: 8
            (D) OTHER INFORMATION: /note= "D-Ala:  D-alanine."

(ix) FEATURE:
            (A) NAME/KEY: Modified-site
            (B) LOCATION: 9..10
            (D) OTHER INFORMATION: /note= "MeLeu:  N-methylleucine."

(ix) FEATURE:
            (A) NAME/KEY: Modified-site
            (B) LOCATION: 11
            (D) OTHER INFORMATION: /note= "MeVal:  N-methylvaline."

(xi) SEQUENCE DESCRIPTION: SEQ ID NO:36:

Xaa Xaa Xaa Xaa Val Xaa Ala Xaa Xaa Xaa Xaa
1               5                   10